US008658377B2

(12) United States Patent
Lillard et al.

(10) Patent No.: US 8,658,377 B2

(45) Date of Patent: *Feb. 25, 2014

(54) DETECTING CANCER WITH ANTI-CCL25 AND ANTI-CCR9 ANTIBODIES

(75) Inventors: James W. Lillard, Smyrna, GA (US); Rajesh Singh, Atlanta, GA (US); Shailesh Singh, Powder Springs, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/324,669

(22) Filed: Dec. 13, 2011

(65) Prior Publication Data

US 2012/0100554 A1 Apr. 26, 2012

Related U.S. Application Data

(63) Continuation-in-part of application No. 13/313,705, filed on Dec. 7, 2011, which is a continuation-in-part of application No. 13/248,904, filed on Sep. 29, 2011, now Pat. No. 8,512,701, which is a continuation-in-part of application No. 13/233,769, filed on Sep. 15, 2011, which is a continuation-in-part of application No. 12/967,273, filed on Dec. 14, 2010, now Pat. No. 8,097,250, which is a continuation of application No. 10/712,398, filed on Nov. 14, 2003, now Pat. No. 7,919,083, application No. 13/324,669, which is a continuation-in-part of application No. 13/312,343, filed on Dec. 6, 2011, which is a continuation-in-part of application No. 13/233,769, filed on Sep. 15, 2011, which is a continuation-in-part of application No. 12/967,273, filed on Dec. 14, 2010, now Pat. No. 8,097,250, which is a continuation of application No. 10/712,398, filed on Nov. 14, 2003, now Pat. No. 7,919,083.

(60) Provisional application No. 60/426,347, filed on Nov. 15, 2002.

(51) Int. Cl.
*G01N 33/53* (2006.01)

(52) U.S. Cl.
USPC .......................................................... 435/7.1

(58) Field of Classification Search
CPC ..................................................... G01N 33/53
See application file for complete search history.

(56) References Cited

U.S. PATENT DOCUMENTS

| | | | |
|---|---|---|---|
| 4,676,980 | A | 6/1987 | Segal et al. |
| 4,816,567 | A | 3/1989 | Cabilly et al. |
| 4,818,542 | A | 4/1989 | DeLuca et al. |
| 4,868,116 | A | 9/1989 | Morgan et al. |
| 4,980,286 | A | 12/1990 | Morgan et al. |
| 5,135,917 | A | 8/1992 | Burch |
| 5,168,053 | A | 12/1992 | Altman et al. |
| 5,176,996 | A | 1/1993 | Hogan et al. |
| 5,334,711 | A | 8/1994 | Sproat et al. |
| 5,476,766 | A | 12/1995 | Gold et al. |
| 5,530,101 | A | 6/1996 | Queen et al. |
| 5,543,293 | A | 8/1996 | Gold et al. |
| 5,580,967 | A | 12/1996 | Joyce |
| 5,595,873 | A | 1/1997 | Joyce |
| 5,624,824 | A | 4/1997 | Yuan et al. |
| 5,631,115 | A | 5/1997 | Ohtsuka et al. |
| 5,646,042 | A | 7/1997 | Stinchcomb et al. |
| 5,652,107 | A | 7/1997 | Lizardi et al. |
| 5,683,873 | A | 11/1997 | George et al. |
| 5,683,874 | A | 11/1997 | Kool |
| 5,728,521 | A | 3/1998 | Yuan et al. |
| 5,861,254 | A | 1/1999 | Schneider et al. |
| 5,861,288 | A | 1/1999 | Usman et al. |
| 5,869,248 | A | 2/1999 | Yuan et al. |
| 5,869,253 | A | 2/1999 | Draper |
| 5,874,566 | A | 2/1999 | Veerapanane et al. |
| 5,877,162 | A | 3/1999 | Werner et al. |
| 5,910,408 | A | 6/1999 | Szostak et al. |
| 5,962,426 | A | 10/1999 | Glazer |
| 5,989,906 | A | 11/1999 | Thompson |
| 5,994,320 | A | 11/1999 | Low et al. |
| 6,017,756 | A | 1/2000 | Draper |
| 6,022,962 | A | 2/2000 | Chowrira et al. |
| 6,030,776 | A | 2/2000 | Eaton et al. |
| 6,046,319 | A | 4/2000 | Power et al. |

(Continued)

FOREIGN PATENT DOCUMENTS

| | | |
|---|---|---|
| WO | 89/07136 | 8/1989 |
| WO | 90/02806 | 3/1990 |

(Continued)

OTHER PUBLICATIONS

Singh et al (Int J Oncol, 2011, 39(2): Abstract).*
Tockman et al (Cancer Res., 1992, 52:2711s-2718s).*
Fusi et al (Journal of Translational Medicine, 2012, 10(52): 1-7).*
Lichtinghagen et al (European Urology, 2002, 42:398-406).*
Seidl et al (Human Pathology, 2007, 38: 768-780).*
International Serarch Report (Application No. PCT/US2003/036557 filed Nov. 14, 20003.
Arenberg, D., et al., "Inhibition of Interleukin-8 Reduces Tumorigenesis of Human Non-Small Cell Lung Cancer in SCID Mice", J Clin Invest, vol. 97, pp. 2792-2802 (1996).
Morrison, et al., Proc. Natl. Acad. Sci. USA 81:6851-6855 (1984).
Mulligan, Science 260:926-932 (1993). Sun, et al., Nature genetics 8:33-41 (1994).
Cotter, et al., Curr Opin Mol Ther 5:633-644 (1999).

(Continued)

*Primary Examiner* — Sean Aeder

(74) *Attorney, Agent, or Firm* — Ping Wang; Andrews Kurth LLP

(57) ABSTRACT

Methods for detecting cancer in a subject are disclosed. The method includes detecting the level of expression of one or more cancer markers in a biological sample obtained from the subject; and comparing the level of expression of the one or more cancer markers in the biological sample to a normal level of expression of the one or more cancer markers. The one or more cancer markers comprise CCL25 or CCR9 or both CCL25 and CCR9.

5 Claims, 25 Drawing Sheets

(56) References Cited

U.S. PATENT DOCUMENTS

| | | | |
|---|---|---|---|
| 6,051,698 | A | 4/2000 | Janjic et al. |
| 6,057,437 | A | 5/2000 | Kamiya et al. |
| 6,261,834 | B1 | 7/2001 | Srivastava |
| 6,936,248 | B1 | 8/2005 | Andrew et al. |

FOREIGN PATENT DOCUMENTS

| | | |
|---|---|---|
| WO | 92/03566 | 3/1992 |
| WO | 93/22434 | 11/1993 |
| WO | 95/24489 | 9/1995 |
| WO | 97/18312 | 5/1997 |
| WO | 98/58058 | 12/1998 |
| WO | 99/50461 | 10/1999 |
| WO | 00/53635 | 9/2000 |

OTHER PUBLICATIONS

Scharf, et al., Results probl Cell Differ 20:125-162 (1994).

Bitter, et al., Methods in Enzymol 153:516-544 (1987).

Hammond, et al., Nature Rev Gen 2:110-119 (2001).

Sharp, Genes Dev 15:485-490 (2001).

Waterhouse, et al., Proc. Natl. Acad. Sci. USA 95(23):13959-13964 (1996).

Marro, et al., Biochem biophys Res Commun. Oct. 13, 2006; 349:270-276.

Forster, et al., Science 238:407-409 (1990).

Yuan, et al., Proc. Natl. Acad. Sci. USA 89:8006-8010 (1992).

Yuan, et al., EMBO J 14:159-168 (1995).

Carrara, et al., Proc. Natl. Acad. Sci. USA 92:2627-2631 (1995).

A.H. Kibbe Handbook of Pharmaceutical Excipients, 3rd ed. Pharmaceutical Press, London, UK (2000).

* cited by examiner

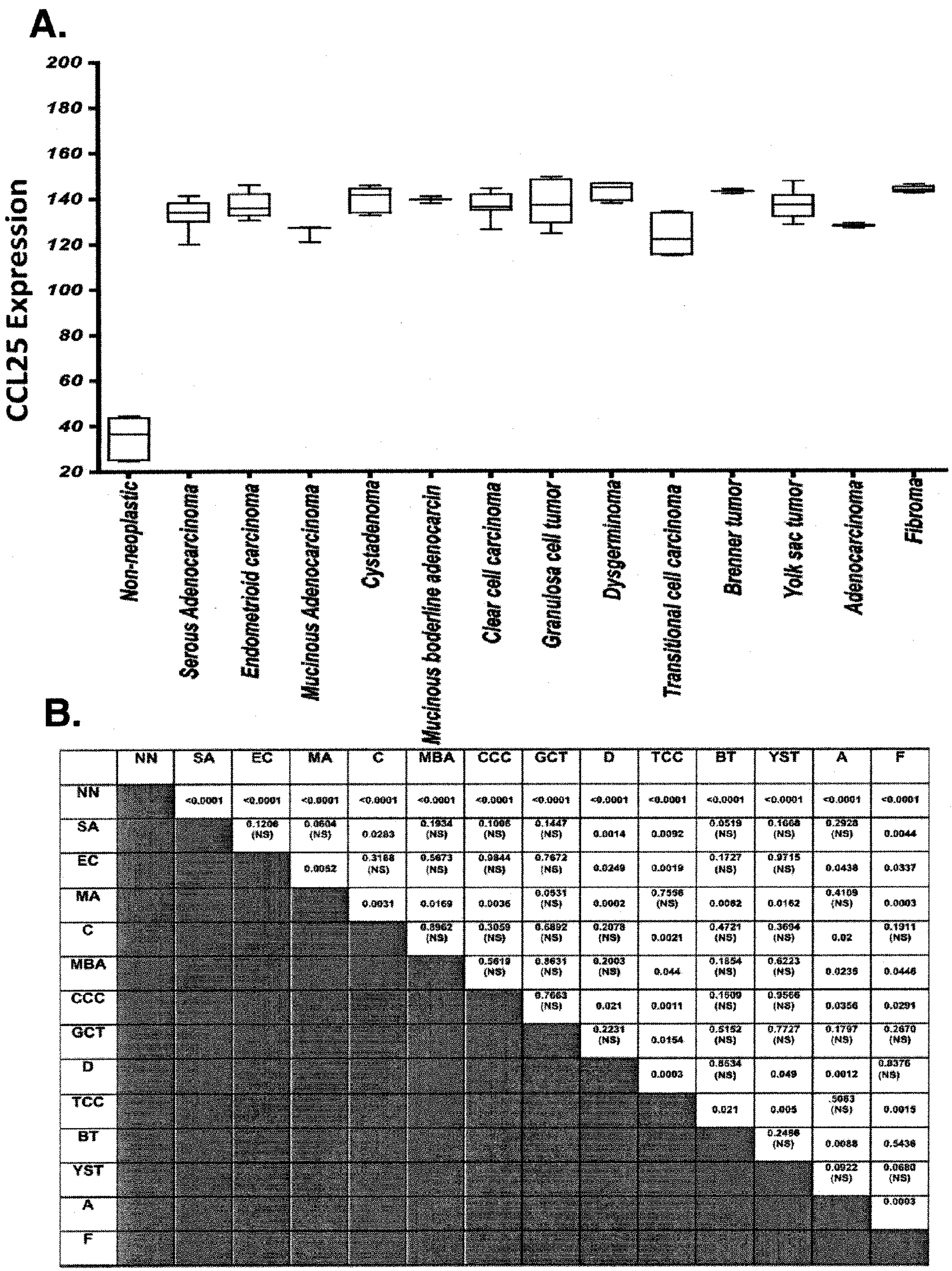

| | NN | SA | EC | MA | C | MBA | CCC | GCT | D | TCC | BT | YST | A | F |
|---|---|---|---|---|---|---|---|---|---|---|---|---|---|---|
| NN | | <0.0001 | <0.0001 | <0.0001 | <0.0001 | <0.0001 | <0.0001 | <0.0001 | <0.0001 | <0.0001 | <0.0001 | <0.0001 | <0.0001 | <0.0001 |
| SA | | | 0.1206 (NS) | 0.0604 (NS) | 0.0283 | 0.1934 (NS) | 0.1086 (NS) | 0.1447 (NS) | 0.0014 | 0.0092 | 0.0519 (NS) | 0.1668 (NS) | 0.2928 (NS) | 0.0044 |
| EC | | | | 0.0052 | 0.3188 (NS) | 0.5673 (NS) | 0.9844 (NS) | 0.7672 (NS) | 0.0249 | 0.0019 | 0.1727 (NS) | 0.9715 (NS) | 0.0438 | 0.0337 |
| MA | | | | | 0.0031 | 0.0169 | 0.0036 | 0.0531 (NS) | 0.0002 | 0.7556 (NS) | 0.0082 | 0.0162 | 0.4109 (NS) | 0.0003 |
| C | | | | | | 0.8962 (NS) | 0.3059 (NS) | 0.6892 (NS) | 0.2078 (NS) | 0.0021 | 0.4721 (NS) | 0.3694 (NS) | 0.02 | 0.1911 (NS) |
| MBA | | | | | | | 0.5619 (NS) | 0.8631 (NS) | 0.2003 (NS) | 0.044 | 0.1854 (NS) | 0.6223 (NS) | 0.0236 | 0.0446 |
| CCC | | | | | | | | 0.7663 (NS) | 0.021 | 0.0011 | 0.1609 (NS) | 0.9566 (NS) | 0.0356 | 0.0291 |
| GCT | | | | | | | | | 0.2231 (NS) | 0.0154 | 0.5152 (NS) | 0.7727 (NS) | 0.1797 (NS) | 0.2670 (NS) |
| D | | | | | | | | | | 0.0003 | 0.8634 (NS) | 0.049 | 0.0012 | 0.8376 (NS) |
| TCC | | | | | | | | | | | 0.021 | 0.005 | .5083 (NS) | 0.0015 |
| BT | | | | | | | | | | | | 0.2486 (NS) | 0.0088 | 0.5436 |
| YST | | | | | | | | | | | | | 0.0922 (NS) | 0.0680 (NS) |
| A | | | | | | | | | | | | | | 0.0003 |
| F | | | | | | | | | | | | | | |

NN: Non-neoplastic; SA: Serous adenocarcinoma; EC: Endometroid carcinoma; MA: Mucinous adenocarcinoma; C: Cystadenoma; MBA: Mucinous boderline adenocarcinoma; CCC: Clear cell carcinoma; GCT: Granulosa cell tumor;D: Dysgerminosa; TCC: Transitional cell carcinoma; BT: Brenner tumor; YST: Yolk sac tumor; A: Adenocarcinoma; F: Fibroma

FIG. 7

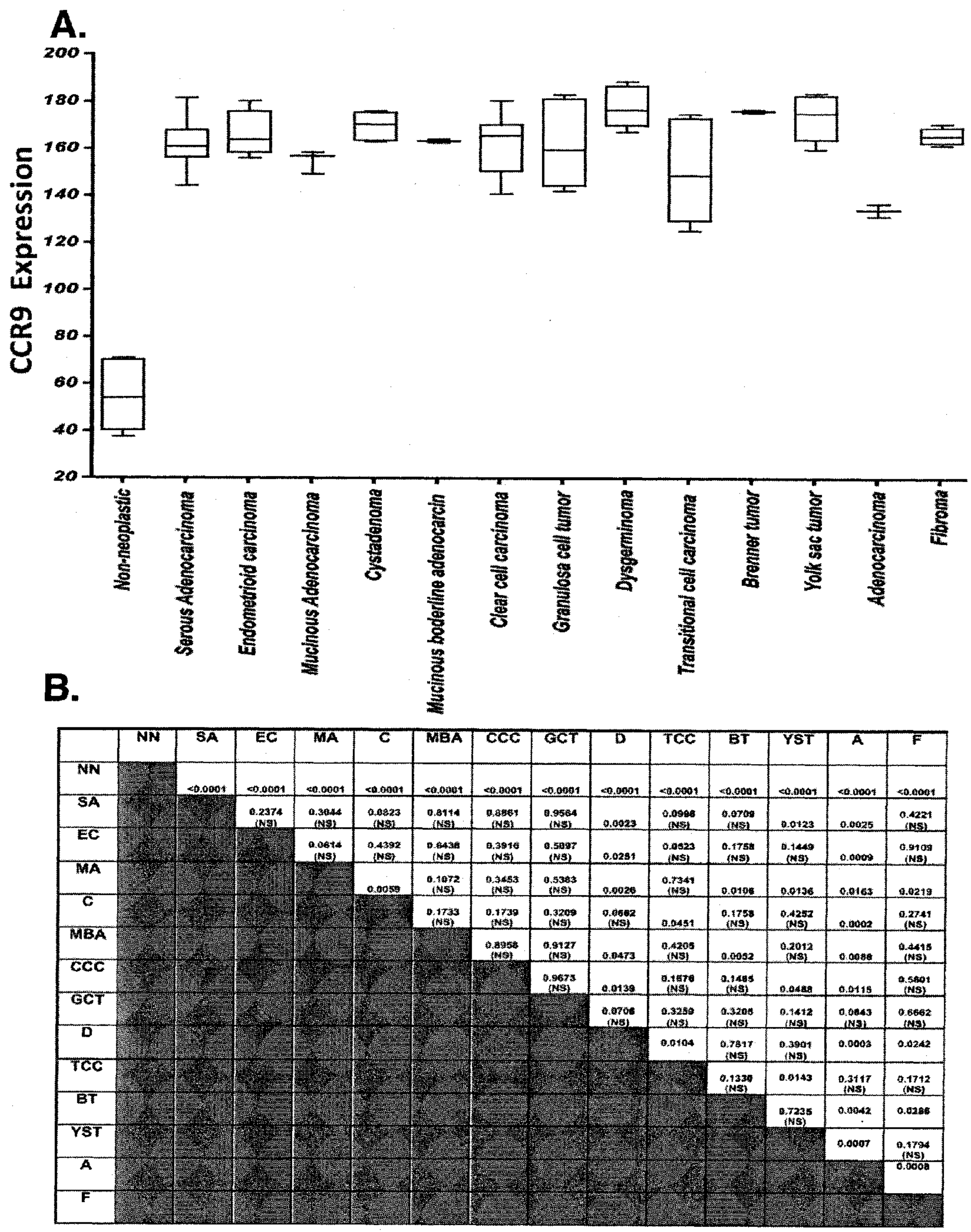

B.

| | NN | SA | EC | MA | C | MBA | CCC | GCT | D | TCC | BT | YST | A | F |
|---|---|---|---|---|---|---|---|---|---|---|---|---|---|---|
| NN | | <0.0001 | <0.0001 | <0.0001 | <0.0001 | <0.0001 | <0.0001 | <0.0001 | <0.0001 | <0.0001 | <0.0001 | <0.0001 | <0.0001 | <0.0001 |
| SA | | | 0.2374 (NS) | 0.3044 (NS) | 0.0823 (NS) | 0.8114 (NS) | 0.8861 (NS) | 0.9564 (NS) | 0.0023 | 0.0998 (NS) | 0.0709 (NS) | 0.0123 | 0.0025 | 0.4221 (NS) |
| EC | | | | 0.0614 (NS) | 0.4392 (NS) | 0.6436 (NS) | 0.3916 (NS) | 0.5897 (NS) | 0.0251 | 0.0623 (NS) | 0.1758 (NS) | 0.1449 (NS) | 0.0009 | 0.9109 (NS) |
| MA | | | | | 0.0059 | 0.1072 (NS) | 0.3453 (NS) | 0.5383 (NS) | 0.0026 | 0.7341 (NS) | 0.0106 | 0.0136 | 0.0163 | 0.0219 |
| C | | | | | | 0.1733 (NS) | 0.1739 (NS) | 0.3209 (NS) | 0.0682 (NS) | 0.0451 | 0.1758 (NS) | 0.4252 (NS) | 0.0002 | 0.2741 (NS) |
| MBA | | | | | | | 0.8958 (NS) | 0.9127 (NS) | 0.0473 | 0.4205 (NS) | 0.0052 | 0.2012 (NS) | 0.0088 | 0.4415 (NS) |
| CCC | | | | | | | | 0.9673 (NS) | 0.0139 | 0.1576 (NS) | 0.1485 (NS) | 0.0488 | 0.0115 | 0.5601 (NS) |
| GCT | | | | | | | | | 0.0706 (NS) | 0.3259 (NS) | 0.3206 (NS) | 0.1412 (NS) | 0.0843 (NS) | 0.6662 (NS) |
| D | | | | | | | | | | 0.0104 | 0.7817 (NS) | 0.3901 (NS) | 0.0003 | 0.0242 |
| TCC | | | | | | | | | | | 0.1336 (NS) | 0.0143 | 0.3117 (NS) | 0.1712 (NS) |
| BT | | | | | | | | | | | | 0.7235 (NS) | 0.0042 | 0.0286 |
| YST | | | | | | | | | | | | | 0.0007 | 0.1794 (NS) |
| A | | | | | | | | | | | | | | 0.0008 |
| F | | | | | | | | | | | | | | |

NN: Non-neoplastic; SA: Serous adenocarcinoma; EC: Endometroid carcinoma; MA: Mucinous adenocarcinoma; C: Cystadenoma; MBA: Mucinous boderline adenocarcinoma; CCC: Clear cell carcinoma; GCT: Granulosa cell tumor;D: Dysgerminosa; TCC: Transitional cell carcinoma; BT: Brenner tumor; YST: Yolk sac tumor; A: Adenocarcinoma; F: Fibroma

FIG. 8

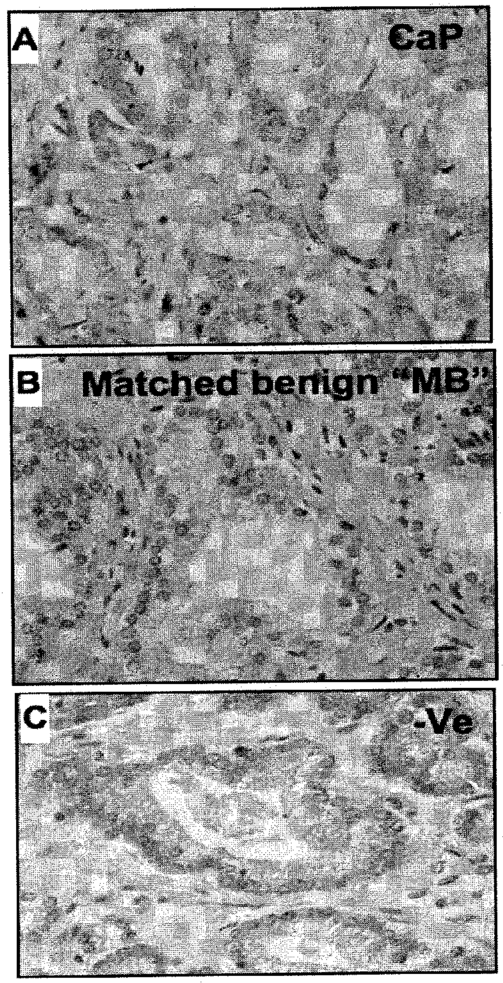
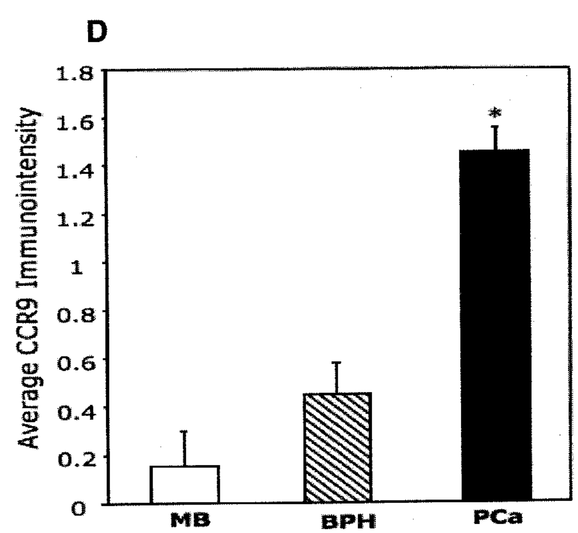
FIG. 16

DETECTING CANCER WITH ANTI-CCL25 AND ANTI-CCR9 ANTIBODIES

This application is a Continuation-In-Part of U.S. patent application Ser. No. 13/313,705, filed on Dec. 7, 2011, which is a Continuation-In-Part of U.S. patent application Ser. No. 13/248,904, filed on Sep. 29, 2011, which is a Continuation-In-Part of U.S. patent application Ser. No. 13/233,769, filed on Sep. 15, 2011, which is a Continuation-In-Part of U.S. patent application Ser. No. 12/967,273, filed Dec. 14, 2010, which is a continuation of U.S. patent application Ser. No. 10/712,398, filed on Nov. 14, 2003, now U.S. Pat. No. 7,919, 083, which claims priority of U.S. Provisional Patent Application No. 60/426,347, filed Nov. 15, 2002. This application is also a Continuation-In-Part of U.S. patent application Ser. No. 13/312,343, filed on Dec. 6, 2011, which is a Continuation-In-Part of U.S. patent application Ser. No. 13/233,769, filed Sep. 15, 2011, which is a Continuation-In-Part of U.S. patent application Ser. No. 12/967,273, filed Dec. 14, 2010, which is a Continuation of U.S. patent application Ser. No. 10/712,398, filed on Nov. 14, 2003, now U.S. Pat. No. 7,919, 083, which claims priority of U.S. Provisional Patent Application No. 60/426,347, filed Nov. 15, 2002. The entirety of all of the aforementioned applications is incorporated herein by reference.

FIELD

This application generally relates to detection of cancer. In particular, the application relates to a method for detecting cancer using anti-chemokine and/or anti-chemokine receptor antibodies.

BACKGROUND

Cancer is one of the leading cause of death in the United States. Most cancer starts in just a single neoplastic cell. The neoplastic cell proliferate to form a local "tumor." A tumor simply means a swelling; it is not necessarily cancerous. A tumor which only grows in its place or origin, and cannot spread distantly, is a benign tumor and is not cancer. However, a tumor which has the capacity to spread (whether it actually does or not) is called a malignant tumor or cancer. A cancer may spread via the blood or lymphatic system to regional lymph nodes and to distant sites via a process called metastasis. A metastasized cancer is more difficult to treat because it now spreads into many different tissues and organs. It has been demonstrated that early treatment increase survival in many types of cancers, such as breast cancer, colon cancer, ovarian cancer and prostate cancer.

Chemokines are a superfamily of small, cytokine-like proteins that are resistant to hydrolysis, promote neovascularization or endothelial cell growth inhibition, induce cytoskeletal rearrangement, activate or inactivate lymphocytes, and mediate chemotaxis through interactions with G-protein coupled receptors. Chemokines can mediate the growth and migration of host cells that express their receptors.

Chemokine (C-C motif) ligand 25 (CCL25), also known as Thymus-Expressed Chemokine (TECK), is a small cytokine belonging to the CC chemokine family. CCL25 is chemotactic for thymocytes, macrophages, and dendritic cells. CCL25 elicits its effects by binding the chemokine receptors CCR9 and is believed to play a role in the development of T-cells. Human CCL25 is produced as a protein precursor containing 151 amino acids. The gene for CCL25 (scya25) is located on human chromosome 19.

Chemokine (C-C motif) receptor 9 (CCR9), also known as GPR 9-6, is very highly expressed in thymus (on both immature and mature T-cells) while low in lymph nodes and spleen. CCR9 is also abundant in the gut, with its expression associated with T cells of the intestine. To note, the chemokine binding protein D6 had previously been referred to as CCR9, but this molecule is a scavenger receptor not a true (signaling) chemokine receptor.

SUMMARY

One aspect of the present application relates to a method for detecting cancer in a subject. The method comprises detecting the level of expression of one or more cancer markers in a biological sample obtained from the subject; and comparing the level of expression of the one or more cancer markers in the biological sample to a normal level of expression of the one or more cancer markers, wherein a higher than normal level of expression of said one or more cancer markers in the biological sample is indicative of the presence of cancer in the subject, wherein the normal level of expression of the one or more cancer markers is a predetermined value or is obtained from a control sample of known normal non-cancerous cells of the same origin or type as the biological sample, wherein the cancer is blastoma, carcinoma, leukemia, lymphoma, melanoma, myeloma, sarcoma or germ cell tumor and wherein the one or more cancer markers comprise CCL25 or CCR9 or both CCL25 and CCR9.

Another aspect of the present application relates to a method for detecting cancer in a subject. The method comprises detecting the level of expression of one or more cancer markers in a biological sample obtained from the subject; and comparing the level of expression of the one or more cancer markers in the biological sample to a normal level of expression of the one or more cancer markers, wherein a higher than normal level of expression of said one or more cancer markers in the biological sample is indicative of the presence of cancer in the subject, wherein the normal level of expression of the one or more cancer markers is a predetermined value or is obtained from a control sample of known normal non-cancerous cells of the same origin or type as the biological sample, wherein the cancer is blastoma, carcinoma, leukemia, lymphoma, melanoma, myeloma, sarcoma or germ cell tumor and wherein the one or more cancer markers comprise: (1) one or more cancer markers selected from the group consisting of CCL25 and CCL9; and (2) one or more cancer markers selected from the group consisting of CXCL13 and CXCR5 and/or one or more cancer markers selected from the group consisting of CXCL16 and CXCR6.

Another aspect of the present application relates to a method for assessing the prognosis of a subject with a cancer. The method comprises determining the expression level of one or more cancer markers in a biological sample from the subject, and comparing the level of expression of the one or more cancer markers in the biological sample to a control level of expression of the one or more cancer markers, wherein a higher level of expression of the one or more cancer markers in the biological sample relative to the control level indicates that the prognosis of the subject is poor, and wherein a lower or similar level of expression of the one or more cancer markers in the biological sample relative to the control level indicates that the prognosis of the subject is good, wherein a poor prognosis indicates that the cancer is of an aggressive or invasive type, wherein the blastoma, carcinoma, leukemia, lymphoma, melanoma, myeloma, sarcoma or germ cell tumor and wherein the one or more cancer markers comprise CCL25 or CCR9 or both CCL25 and CCR9.

Another aspect of the present application relates to a method for assessing the prognosis of a subject with a cancer. The method comprises determining the expression level of one or more cancer markers in a biological sample from the subject, and comparing the level of expression of the one or more cancer markers in the biological sample to a control level of expression of the one or more cancer markers, wherein a higher level of expression of the one or more cancer markers in the biological sample relative to the control level indicates that the prognosis of the subject is poor, and wherein a lower or similar level of expression of the one or more cancer markers in the biological sample relative to the control level indicates that the prognosis of the subject is good, wherein a poor prognosis indicates that the cancer is of an aggressive or invasive type, wherein the cancer is blastoma, carcinoma, leukemia, lymphoma, melanoma, myeloma, sarcoma or germ cell tumor and wherein the one or more cancer markers comprise: (1) one or more cancer markers selected from the group consisting of CCL25 and CCL9; and (2) one or more cancer markers selected from the group consisting of CXCL13 and CXCR5 and/or one or more cancer markers selected from the group consisting of CXCL16 and CXCR6.

Another aspect of the present application relates to a method for monitoring the course of cancer treatment in a subject. The method comprises determining the expression levels of one or more cancer markers in one or more biological samples obtained from the subject during or after the treatment, and comparing the level of expression of the one or more cancer markers in the one or more biological samples to a control level of expression of the one or more cancer markers, wherein the control level of the one or more cancer markers is a pre-treatment level of the one or more cancer markers in the subject or a predetermined reference level, wherein the treatment is deemed efficacious if the one or more cancer markers in the one or more biological samples is similar to or lower than the control level, wherein the cancer is blastoma, carcinoma, leukemia, lymphoma, melanoma, myeloma, sarcoma or germ cell tumor and wherein the one or more cancer markers comprise CCL25 or CCR9 or both CCL25 and CCR9.

Another aspect of the present application relates to a method for monitoring the course of cancer treatment in a subject. The method comprises determining the expression levels of one or more cancer markers in one or more biological samples obtained from the subject during or after the treatment, and comparing the level of expression of the one or more cancer markers in the one or more biological samples to a control level of expression of the one or more cancer markers, wherein the control level of the one or more cancer markers is a pre-treatment level of the one or more cancer markers in the subject or a predetermined reference level, wherein the treatment is deemed efficacious if the one or more cancer markers in the one or more biological samples is similar to or lower than the control level, wherein the cancer is blastoma, carcinoma, leukemia, lymphoma, melanoma, myeloma, sarcoma or germ cell tumor and wherein the one or more cancer markers comprise: (1) one or more cancer markers selected from the group consisting of CCL25 and CCL9; and (2) one or more cancer markers selected from the group consisting of CXCL13 and CXCR5 and/or one or more cancer markers selected from the group consisting of CXCL16 and CXCR6.

Another aspect of the present application relates to a kit for detecting cancer. The kit comprises reagents for determining expression of CCL25 and/or CCR9 in a biological sample; and instructions for how to use the reagents, wherein the reagents comprise an anti-CCL25 antibody, an anti-CCR9 antibody, or both.

BRIEF DESCRIPTION OF THE DRAWINGS

FIGS. 7A-B show an analysis of CCL25 expression by ovarian cancer tissues.

FIGS. 8A-B show an analysis of CCR9 expression by ovarian cancer tissues.

FIGS. 16A-D show CCR9 expression by prostate tissue.

DETAILED DESCRIPTION

Figure 1:
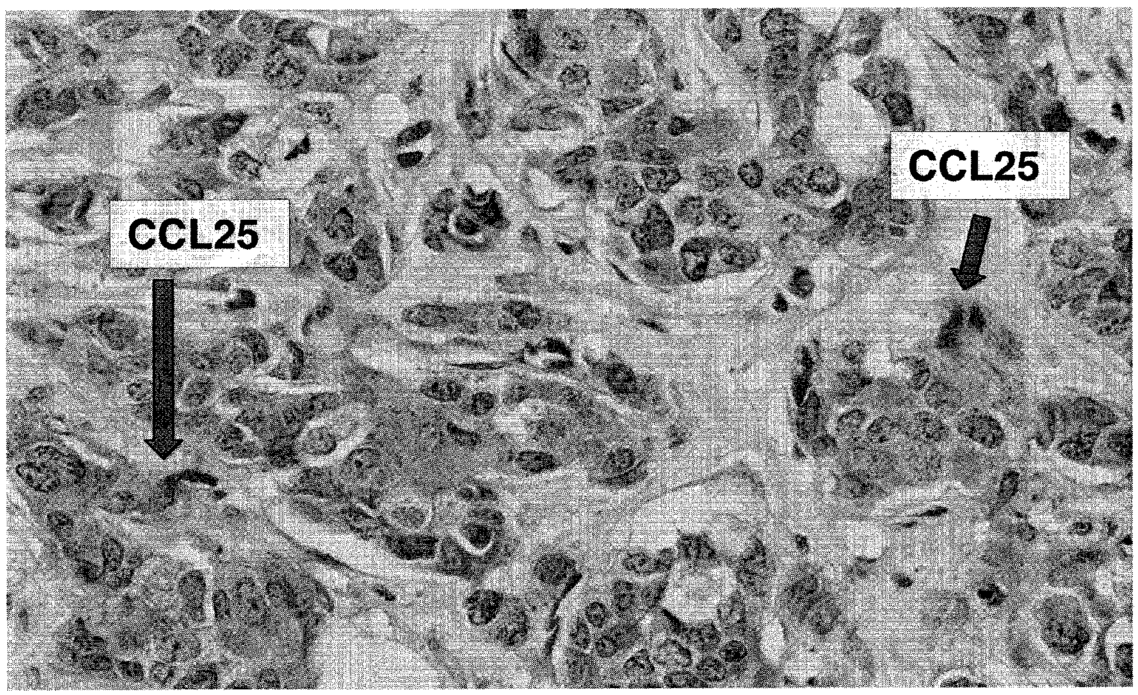
FIG. 1 shows CCL25 expression by breast cancer tissue.

The following detailed description is presented to enable any person skilled in the art to make and use the application. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

As used herein, the following terms shall have the following meanings:

As used herein, the teen "antibody" refers to immunoglobulin molecules and immunologically active portions of immunoglobulin (Ig) molecules, i.e., molecules that contain an antigen binding site that specifically binds (immunoreacts with) an antigen. The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. By "specifically bind" or "immunoreacts with" is meant that the antibody reacts with one or more antigenic determinants of the desired antigen and does not react (i.e., bind) with other polypeptides or binds at much lower affinity with other polypeptides. The term "antibody" also includes antibody fragments that comprise a portion of a full length antibody, generally the antigen binding or variable region thereof. Examples of antibody fragments include Fab, Fab', F(ab')2, and Fv fragments; diabodies; linear antibodies; single-chain antibody (scFv) molecules; and multispecific antibodies formed from antibody fragments. In certain embodiments of the application, it may be desirable to use an antibody fragment, rather than an intact antibody, to increase tumor penetration, for example. In this case, it may be desirable to use an antibody fragment that has been modified by any means known in the art in order to increase its serum half life.

The term "monoclonal antibody" as used herein refers to an antibody obtained from a population of substantially homogeneous antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. Methods for making humanized and other chimeric antibodies are known in the art.

"Bispecific antibodies" are antibodies that have binding specificities for at least two different antigens. In the present case, one of the binding specificities is for CXCL16 or CXCR6. The second binding target is any other antigen, and advantageously is a cell-surface protein or receptor or receptor subunit. Methods for making bispecific antibodies are known in the art.

The use of "heteroconjugate antibodies" is also within the scope of the present application. Heteroconjugate antibodies are composed of two covalently joined antibodies. Such antibodies have, for example, been proposed to target immune system cells to unwanted cells (U.S. Pat. No. 4,676,980). It is contemplated that the antibodies can be prepared in vitro using known methods in synthetic protein chemistry, including those involving crosslinking agents.

The teen "tumor" as used herein refers to a neoplasm or a solid lesion formed by an abnormal growth of cells. A tumor can be benign, pre-malignant or malignant.

A "primary tumor" is a tumor appearing at a first site within the subject and can be distinguished from a "metastatic tumor" which appears in the body of the subject at a remote site from the primary tumor.

The term "cancer," as used herein, refer to or describe the physiological condition in mammals that is typically characterized by unregulated cell growth. Exemplary cancers include: carcinoma, melanoma, sarcoma, lymphoma, leukemia, germ cell tumor, and blastoma. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The term "carcinoma" as used herein refers to an invasive malignant tumor consisting of transformed epithelial cells or transformed cells of unknown histogenesis, but which possess specific molecular or histological characteristics that are associated with epithelial cells, such as the production of cytokeratins or intercellular bridges. Exemplary carcinomas of the present application include ovarian cancer, vaginal cancer, cervical cancer, uterine cancer, prostate cancer, anal cancer, rectal cancer, colon cancer, stomach cancer, pancreatic cancer, insulinoma, adenocarcinoma, adenosquamous carcinoma, neuroendocrine tumor, breast cancer, lung cancer, esophageal cancer, oral cancer, brain cancer, medulloblastoma, neuroectodermal tumor, glioma, pituitary cancer, and bone cancer.

The term "lymphoma" as used herein is a cancer of lymphatic cells of the immune system. Lymphomas typically present as a solid tumor. Exemplary lymphomas include: small lymphocytic lymphoma, lymphoplasmacytic lymphoma, Waldenström macroglobulinemia, splenic marginal zone lymphoma, plasmacytoma, extranodal marginal zone B cell lymphoma, MALT lymphoma, nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, Burkitt lymphoma, B cell chronic lymphocytic lymphoma, classical Hodgkin lymphoma, nodular lymphocyte-predominant Hodgkin lymphoma, adult T cell lymphoma, nasal type extranodal NK/T cell lymphoma, enteropathy-type T cell lymphoma, hepatosplenic T cell lymphoma, blastic NK cell lymphoma, mycosis fungoide, Sezary syndrome, primary cutaneous CD30-positive T cell lymphoproliferative disorders, primary cutaneous anaplastic large cell lymphoma, lymphomatoid papulosis, angioimmunoblastic T cell lymphoma, unspecified peripheral T cell lymphoma, and anaplastic large cell lymphoma. Exemplary forms of classical Hodgkin lymphoma including: nodular sclerosis, mixed cellularity, lymphocyte-rich, and lymphocyte-depleted or not depleted.

The term "sarcoma" as used herein is a cancer that arises from transformed cells in one of a number of tissues that develop from embryonic mesoderm. Thus, sarcomas include tumors of bone, cartilage, fat, muscle, vascular, and hematopoietic tissues. For example, osteosarcoma arises from bone, chondrosarcoma arises from cartilage, liposarcoma arises from fat, and leiomyosarcoma arises from smooth muscle. Exemplary sarcomas include: Askin's tumor, botryodies, chondrosarcoma, Ewing's-PNET, malignant Hemangioendothelioma, malignant Schwannoma, osteosarcoma, soft tissue sarcomas. Subclases of soft tissue sarcomas include: alveolar soft part sarcoma, angiosarcoma, cystosarcoma phyllodes, dermatofibrosarcomadesmoid tumor, desmoplastic small round cell tumor, epithelioid sarcomaextraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcomal, lymphosarcoma, malignant fibrous histiocytoma, neurofibrosarcoma, rhabdomyosarcoma, and synovial sarcoma.

The term "leukemia" as used herein is a cancer of the blood or bone marrow characterized by an abnormal increase of white blood cells. Leukemia is a broad term covering a spectrum of diseases. In turn, it is part of the even broader group of diseases called hematological neoplasms. Leukemia is subdivided into a variety of large groups; the first division is between acute and chronic forms of leukemia. Acute leukemia is characterized by a rapid increase in the numbers of immature blood cells. Crowding due to such cells makes the bone marrow unable to produce healthy blood cells. Chronic leukemia is characterized by the excessive build up of relatively mature, but still abnormal, white blood cells. Typically taking months or years to progress, the cells are produced at a much higher rate than normal cells, resulting in many abnormal white blood cells in the blood. Leukemia is also subdivided by the blood cells affected. This split divides leukemias into lymphoblastic or lymphocytic leukemias and myeloid or myelogenous leukemias. In lymphoblastic or lymphocytic leukemias, the cancerous change takes place in a type of marrow cell that normally goes on to form lymphocytes. In myeloid or myelogenous leukemias, the cancerous change takes place in a type of marrow cell that normally goes on to form red blood cells, some other types of white cells, and platelets. Combining these two classifications provides a total of four main categories. Within each of these four main categories, there are typically several subcategories. There are also rare types outside of this classification scheme. Exemplary leukemias include: acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia, large granular lymphocytic leukemia, juvenile myelomonocytic leukemia, B-cell prolymphocytic leukemia, Burkitt leukemia, and adult T-cell leukemia.

The term "melanoma" as used herein is a cancer or malignant tumor of melanocytes. Melanocytes are cells that produce the dark pigment, melanin, which is responsible for the color of skin. They predominantly occur in skin, but are also found in other parts of the body, including the bowel and the eye. Melanoma is divided into the following stereotypes and subtypes: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, and uveal melanoma.

The term "germ cell tumor (GCT)" as used herein is a neoplasm derived from germ cells. Germ cell tumors can be cancerous or non-cancerous tumors. Germ cells normally occur inside the gonads (ovary and testis). Germ cell tumors that originate outside the gonads may be birth defects resulting from errors during development of the embryo. Germ cell tumors are broadly divided in two classes: germinomatous or seminomatous and nongerminomatous or nonseminomatous germ cell tumors. Exemplary germinomatous or seminomatous germ cell tumors include: germinoma, dysgerminoma, and seminoma. Exemplary nongerminomatous or nonseminomatous germ cell tumors include: Embryonal carcinoma, endodermal sinus tumor or yolk sac tumor (EST, YST), choriocarcinoma, mature teratoma, dermoid cyst, immature teratoma, teratoma with malignant transformation, polyembryoma, gonadoblastoma, and mixed GCT.

The term "metastasis" as used herein refers to the spread of a cancer or carcinoma from one organ or part to another non-adjacent organ or part.

The term "biological sample" refers to a sample of biological material obtained from a mammal subject, preferably a human subject, including a tissue, a tissue sample, a cell sample, a tumor sample, a stool sample, and a biological fluid, e.g., blood, plasma, serum, saliva, urine, cerebral or spinal fluid, lymph liquid and a nipple aspirate. A biological sample may be obtained in the form of, e.g., a tissue biopsy, such as, an aspiration biopsy, a brush biopsy, a surface biopsy, a needle biopsy, a punch biopsy, an excision biopsy, an open biopsy, an incision biopsy and an endoscopic biopsy. In one embodiment, the biological sample is a blood, serum or plasma sample. In another embodiment, the biological sample is a saliva sample. In yet another embodiment, the biological sample is a urine sample.

An "isolate" of a biological sample (e.g., an isolate of a tissue or tumor sample) refers to a material or composition (e.g., a biological material or composition) which has been separated, derived, extracted, purified or isolated from the sample and preferably is substantially free of undesirable compositions and/or impurities or contaminants associated with the biological sample.

A "tissue sample" includes a portion, piece, part, segment, or fraction of a tissue which is obtained or removed from an intact tissue of a subject, preferably a human subject.

A "tumor sample" includes to a portion, piece, part, segment, or fraction of a tumor, for example, a tumor which is obtained or removed from a subject (e.g., removed or extracted from a tissue of a subject), preferably a human subject. A tumor sample may be obtained from a primary tumor or a metastatic tumor.

A "mammal" for purposes of treatment refers to any animal classified as a mammal, including humans, non-human primates, domestic and farm animals, and zoo, sports, or pet animals, such as dogs, horses, cats, cows, etc. Preferably, the mammal is human.

The term "increased level" refers to a level that is higher than a normal or control level customarily defined or used in the relevant art. For example, an increased level of immunostaining in a tissue is a level of immunostaining that would be considered higher than the level of immunostaining in a control tissue by a person of ordinary skill in the art.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. As used herein, the term "antibody" refers to immunoglobulin molecules and immunologically active portions of immunoglobulin (Ig) molecules, i.e., molecules that contain an antigen binding site that specifically binds (immunoreacts with) an antigen.

Method for Detecting Cancer by Measuring CCL25 and/or CCR9 Expression or Activity CCL25 is a ligand for the CCR9 chemokine receptor. Both the chemokine and the receptor appear to play a role in the regulation of metastasis and invasion of cancer. Both CCL25 and CCR9 are locally up-regulated in multiple carcinoma tissue types compared to normal tissues, including ovarian, lung, breast, prostate, colon, bone and pancreatic cancers. CCL25 levels are also increased in the serum of patients with those cancers. Additionally, soluble CCL25 chemokine enhances both in vivo and in vitro proliferation and migration of cancer cells.

CCR9 is a member of the chemokine receptor family of G protein coupled receptors (GPCRs) that may have a diverse role in cancer cell survival that presumably supports protection against chemotherapeutic drugs. We show that interaction of CCR9 with CCL25 modulates matrix metalloproteinase (MMP) expression and enhances the migration and invasive potential of carcinoma cells. This suggests that CCR9-CCL25 interaction contributes to carcinoma cell migration and invasion. Accordingly, blocking this axis has the potential to inhibit carcinoma cell metastasis).

One aspect of the present application relates to a method for detecting the presence of cancer in a subject, comprising: detecting the level of expression of one or more cancer markers in a biological sample obtained from said subject; and comparing the level of expression of said one or more cancer markers in said biological sample to a normal level of expression of said one or more cancer markers, wherein a higher than normal level of expression of said one or more cancer markers in said biological sample is indicative of the presence of cancer in said subject, wherein said normal level of expression of said one or more cancer markers is a predetermined value or is obtained from a control sample of known normal non-cancerous cells of the same origin or type as said biological sample, and wherein said cancer is blastoma, carcinoma, leukemia, lymphoma, melanoma, myeloma, sarcoma or germ cell tumor and wherein said one or more cancer markers comprises CCL25 or CCR9 or both CCL25 and CCR9.

In one embodiment, said one or more cancer markers comprise (1) CCL25 or CCR9 or both CCL25 and CCR9 and (2) CXCL13 or CXCR5 or both CXCL13 and CXCR5. In another embodiment, said one or more cancer markers comprise (1) CCL25 or CCR9 or both CCL25 and CCR9 and (2) CXCL16 or CXCR6 or both CXCL16 and CXCR6.

In another embodiment, said one or more cancer markers comprise (1) CCL25 or CCR9 or both CCL25 and CCR9, (2) CXCL13 or CXCR5 or both CXCL13 and CXCR5, and (3) CXCL16 or CXCR6 or both CXCL16 and CXCR6. In another embodiment, said one or more cancer markers comprise (1) CCL25 or CCR9 or both CCL25 and CCR9, and/or (2) CXCL13 or CXCR5 or both CXCL13 and CXCR5, and/or (3) CXCL16 or CXCR6 or both CXCL16 and CXCR6' and (4) one or more other cancer markers.

In still another embodiment, said one or more other cancer markers comprise (1) CCL25 or CCR9 or both CCL25 and CCR9, and (2) one or more cancer markers selected from the group consisting of CXCL1, CXCL2, CXCL3, CXCL4, CXCL6, CXCL7, CXCL8, CXCL9, CXCL10, CXCL11, CXCL12, CXCL13, CXCL14, CXCL15, CXCL16, CXCR1, CXCR2, CXCR3, CXCR4, CXCR5, CXCR6, CXCR7, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL24, CCL25, CCL25-1, CCL25-2, CCL27, CCL28, CCR1, CCR2, CCR3, CCR4, CCR5, CCR6, CCR7, CCR8, CCR9, CCR10, CCR11, XCL1, XCL2, XCR1, CX3CR1, CX3CL1, HER2, RNA binding motif 3 ("RBM3"), carcinoembryonic Antigen (CEA), prostate specific antigen (PSA), chromgranin A (CGA), dehydroepiandrosterone (DHEA), neuron-specific enolase (NSE), prostatic acid phosphatase (PAP), prolactin, B7-H3, seprase polypeptide, anti-p53, osteopontin, ferritin, lysophosphatidyl choline, kinesin family member 4A (KIF4A), Neural pentraxin I (NPTX1) and fibroblast growth factor receptor 1 oncogene partner (FGFR1OP) protein.

In another embodiment, said cancer is breast cancer and wherein the one or more cancer markers comprise (1) CCL25 or CCR9 or both CCL25 and CCR9, and (2) one or more cancer markers selected from the group consisting of CCL1, CCL2, CCL4, CCL17, CCL19, CCL21, CCL22, CXCL12, CXCL13, CXCL16, CX3CL1, CCR2, CCR7, CCR8, CXCR4, CXCR5, CXCR6 CX3CR1, HER2, RBM3 and CEA.

In another embodiment, said carcinoma is prostate cancer and wherein the one or more cancer markers comprise (1) CCL25 or CCR9 or both CCL25 and CCR9, and (2) one or more cancer markers selected from the group consisting of CCL1, CCL2, CCL4, CCL17, CCL19, CCL21, CCL22, CXCL12, CXCL13, CXCL16, CX3CL1, CCR2, CCR7, CCR8, CXCR4, CXCR5, CXCR6, CX3CR1, PSA, CEA, CGA, DHEA, NSE, PAP, prolactin and B7-H3.

In another further embodiment, said carcinoma is colorectal cancer and wherein the one or more cancer markers comprise (1) CCL25 or CCR9 or both CCL25 and CCR9, and (2) one or more cancer markers selected from the group consisting of CCL1, CCL2, CCL4, CCL17, CCL19, CCL21, CCL22, CXCL12, CXCL13, CXCL16, CX3CL1, CCR2, CCR7, CCR8, CXCR4, CXCR5, CXCR6, CX3CR1, seprase polypeptide, anti-p53, osteopontin, and ferritin.

In another further embodiment, said carcinoma is ovarian cancer and wherein the one or more cancer markers comprise (1) CCL25 or CCR9 or both CCL25 and CCR9, and (2) one or more cancer markers selected from the group consisting of CCL1, CCL2, CCL4, CCL17, CCL19, CCL21, CCL22, CXCL12, CXCL13, CXCL16, CX3CL1, CCR2, CCR7, CCR8, CXCR4, CXCR5, CXCR6, CX3CR1, cancer antigen 125 (CA-125), HE-4, OVX-1 macrophage colony stimulating factor (M-CSF) and lysophosphatidyl choline.

In another further embodiment, said carcinoma is lung cancer and wherein the one or more cancer markers comprise (1) CCL25 or CCR9 or both CCL25 and CCR9, and (2) one or more cancer markers selected from the group consisting of CCL1, CCL2, CCL4, CCL17, CCL19, CCL21, CCL22, CCL25, CXCL12, CXCL13, CXCL16, CX3CL1, CCR2, CCR7, CCR8, CCR9, CXCR4, CXCR5, CXCR6, CX3CR1, kinesin family member 4A (KIF4A), Neural pentraxin I (NPTX1), fibroblast growth factor receptor 1 oncogene partner (FGFR1OP) protein and CEA.

In another further embodiment, said carcinoma is pancreatic cancer or gastric cancer and wherein the one or more cancer markers comprise (1) CCL25 or CCR9 or both CCL25 and CCR9, and (2) one or more cancer markers selected from the group consisting of CCL1, CCL2, CCL4, CCL17, CCL19, CCL21, CCL22, CXCL12, CXCL13, CXCL16, CX3CL1, CCR2, CCR7, CCR8, CXCR4, CXCR5, CXCR6, CX3CR1 and CEA.

In another further embodiment, the carcinoma is brain cancer, pituitary cancer or bone cancer and wherein one or more cancer markers further comprises one or more cancer markers selected from the group consisting of CCL1, CCL2, CCL4, CCL17, CCL19, CCL21, CCL22, CXCL12, CXCL13, CXCL16, CX3CL1, CCR2, CCR7, CCR8, CXCR4, CXCR5, CXCR6 and CX3CR1.

In some other embodiments, the biological sample is a plasma sample, a saliva sample or a urine sample.

In the context of the present application, the term "detecting" is intended to encompass predictions and likelihood analysis. The present method is intended to be used clinically in making decisions concerning treatment modalities, including therapeutic intervention, diagnostic criteria such as disease stages, and disease monitoring and surveillance for cancer. According to the present application, an intermediate result for examining the condition of a subject may be provided. Such intermediate result may be combined with additional information to assist a doctor, nurse, or other practitioner to diagnose that a subject suffers from the disease. Alternatively, the present application may be used to detect cancerous cells in a subject-derived tissue, and provide a doctor with useful information to diagnose that the subject suffers from the disease. The subject is preferably a human, but may also include other mammals such as non-human primate, mouse, rat, dog, cat, horse, and cow.

Method for Assessing the Prognosis of a Subject Having Cancer

The present method for detecting cancer may also be applied for assessing the prognosis of a patient with the cancer by comparing the expression level of one or more cancer markers in a patient-derived biological sample with that of a reference sample.

Therefore, another aspect of the present application relates to a method for assessing the prognosis of a subject with a cancer, comprising: determining the expression level of one or more cancer markers in a biological sample from said subject, and comparing the level of expression of said one or more cancer markers in said biological sample to a control level of expression of said one or more cancer markers, wherein a higher level of expression of said one or more cancer markers in the biological sample relative to said control level indicates that the prognosis of said subject is poor, wherein a lower or similar level of expression of said one or more cancer markers in said biological sample relative to said control level indicates that the prognosis of said subject is good, wherein a poor prognosis indicates that said cancer is of an aggressive or invasive type, wherein said cancer is blastoma, carcinoma, leukemia, lymphoma, melanoma, myeloma, sarcoma or germ cell tumor, and wherein said one or more cancer markers comprise CCL25 or CCR9 or both CCL25 and CCR9.

In one embodiment, said one or more cancer markers further comprises CXCL13 or CXCR5 or both CXCL13 and CXCR5. In another embodiment, said one or more cancer markers further comprises CXCL16 or CXCR6 or both CXCL16 and CXCR6.

In another embodiment, said one or more cancer markers further comprises (1) CXCL13 or CXCR5 or both CXCL13 and CXCR5, and (2) CXCL16 or CXCR6 or both CXCL16 and CXCR6.

In still another embodiment, said one or more cancer markers further comprises one or more cancer markers selected from the group consisting of CXCL13, CXCR5, CXCL16, CXCR6, CCL1, CCL2, CCL4, CCL17, CCL19, CCL21, CCL22, CCL27, CXCL1, CXCL2, CXCL3, CXCL5, CXCL6, CXCL7, CXCL8, CXCL12, CX3CL1, CCR2, CCR7, CCR8, CCR10, CXCR1, CXCR2, CXCR4, CXCR7 and CX3CR1.

Alternatively, the level of one or more cancer markers in the biological sample may be measured over a spectrum of disease stages to assess the prognosis of the patient. An increase in the expression level of one or more cancer markers as compared to a normal control level indicates less favorable prognosis. A similarity in the expression level of one or more cancer markers as compared to a normal control level indicates a more favorable prognosis of the patient.

In some other embodiments, the biological sample is a plasma sample, a saliva sample or a urine sample.

Method for Monitoring the Course of Cancer Treatment

In certain embodiments, the level(s) of one or more cancer markers is used to monitor the course of treatment of cancer. In this method, a test biological sample is provided from a subject undergoing treatment for cancer. Preferably, multiple test biological samples are obtained from the subject at various time points before, during or after the treatment. The expression level of the cancer marker in the post-treatment sample may then be compared with the level of the cancer marker in the pre-treatment sample or, alternatively, with a reference sample (e.g., a normal control level). For example, if the post-treatment marker level is lower than the pre-treatment marker level, one can conclude that the treatment was efficacious. Likewise, if the post-treatment marker level is similar to, or the same as, the normal control marker level, one can also conclude that the treatment was efficacious.

An "efficacious" treatment is one that leads to a reduction in the level of a cancer marker or a decrease in size, prevalence or metastatic potential of cancer in a subject. When a treatment is applied prophylactically, "efficacious" means that the treatment retards or prevents occurrence of cancer or alleviates a clinical symptom of cancer. The assessment of cancer can be made using standard clinical protocols. Furthermore, the efficaciousness of a treatment can be determined in association with any known method for diagnosing or treating cancer. For example, cancer is routinely diagnosed histopathologically or by identifying symptomatic anomalies such as weight loss and loss of appetite.

Accordingly, another aspect of the present application relates to a method for monitoring the course of cancer treatment in a subject, comprising: determining the expression levels of one or more cancer markers in one or more biological samples obtained from said subject during or after said treatment, and comparing the level of expression of said one or more cancer markers in said one or more biological samples to a control level of expression of said one or more cancer markers, wherein said control level of said one or more cancer markers is a pre-treatment level of said one or more cancer markers in said subject or a predetermined reference level, wherein said treatment is deemed efficacious if said one or more cancer markers in said one or more biological samples is similar to or lower than said control level, wherein said cancer is blastoma, carcinoma, leukemia, lymphoma, melanoma, myeloma, sarcoma or germ cell tumor, and wherein said one or more cancer markers comprise CCL25 or CCR9 or both CCL25 and CCR9.

In one embodiment, said one or more cancer markers further comprises CXCL13 or CXCR5 or both CXCL13 and CXCR5. In another embodiment, said one or more cancer markers further comprises CXCL16 or CXCR6 or both CXCL16 and CXCR6.

In another embodiment, said one or more cancer markers further comprises (1) CXCL13 or CXCR5 or both CXCL13 and CXCR5 and (2) CXCL16 or CXCR6 or both CXCL16 and CXCR6.

In still another embodiment, said one or more cancer markers further comprises one or more cancer markers selected from the group consisting of CXCL13, CXCR5, CXCL16, CXCR6, CCL1, CCL2, CCL4, CCL17, CCL19, CCL21, CCL22, CCL27, CXCL1, CXCL2, CXCL3, CXCL5, CXCL6, CXCL7, CXCL8, CXCL12, CX3CL1, CCR2, CCR7, CCR8, CCR10, CXCR1, CXCR2, CXCR4, CXCR7 and CX3CR1.

Cancer Markers

The term "cancer marker" as used herein, refers to or describes a polypeptide or a polynuceotide whose expression level, alone or in combination with other polypeptides or a polynuceotides, is correlated with cancer or prognosis of cancer. The correlation may relate to either an increased or decreased expression of the polypeptide or a polynuceotide. For example, the expression of the polypeptide or a polynuceotide may be indicative of cancer, or lack of expression of the polypeptide or a polynuceotide may be correlated with poor prognosis in a cancer patient.

The teen "expression level of a cancer marker" may be measured at the transcription level, in which case the presence and/or the amount of a polynucleotide is determined, or at the translation level, in which case the presence and/or the amount of a polypeptide is determined. Cancer marker expression may be characterized using any suitable method.

Examples of the cancer marker include CCL25, CCR9 and other chemokines and chemokine receptors such as CXCL1, CXCL2, CXCL3, CXCL4, CXCL6, CXCL7, CXCL8, CXCL9, CXCL10, CXCL11, CXCL12, CXCL 13, CXCL14, CXCL15, CXCL16, CXCR1, CXCR2, CXCR3, CXCR4, CXCR5, CXCR6, CXCR7, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL24, CCL27, CCL28, CCR1, CCR2, CCR3, CCR4, CCR5, CCR6, CCR7, CCR8, CCR10, CCR11, XCL1, XCL2, XCR1, CX3CR1, CX3CL1, RNA binding motif 3 ("RBM3"), carcinoembryonic Antigen (CEA), prostate specific antigen (PSA), chromgranin A (CGA), dehydroepiandrosterone (DHEA), neuron-specific enolase (NSE), prostatic acid phosphatase (PAP), prolactin, B7-H3, seprase polypeptide, anti-p53, osteopontin, ferritin, lysophosphatidyl choline, kinesin family member 4A (KIF4A), Neural pentraxin I (NPTX1) and fibroblast growth factor receptor 1 oncogene partner (FGFR1OP) protein.

In one embodiment, the cancer markers used in the present application are selected from a melanoma marker panel that includes CCL25, CCR9, CXCL13, CXCR5, CXCL16, CXCR6, CCL27, CXCL1, CXCL2, CXCL3, CXCL5, CXCL6, CXCL7, CXCL8, CXCL12, CX3CL1, CCR10, CXCR1, CXCR2, CXCR4, and CX3CR1. The markers in the melanoma panel may be used for detecting melanoma or predicting the prognosis of a subject having melanoma.

In one embodiment, the cancer markers described above are selected from a carcinoma marker panel that includes CCL25, CCR9, CXCL13, CXCR5, CCL1, CCL4, CCL17, CCL19, CCL21, CCL22, CXCL12, CXCL16, CCR7, CCR8, CXCR4, CXCR6 and CX3CR1. The markers in the carcinoma panel may be used for detecting carcinoma or predicting the prognosis of a subject having carcinoma.

In another embodiment, the cancer markers described above are selected from a breast cancer marker panel that includes CCL25, CCR9, CXCL13, CXCR5, CCL1, CCL4, CCL17, CCL19, CCL21, CCL22, CXCL12, CXCL16, CCR7, CCR8, CXCR4, CXCR6, CX3CR1, HER2, RNA binding motif 3 ("RBM3") and carcinoembryonic Antigen (CEA). The markers in the breast cancer panel may be used for detecting breast cancer or predicting the prognosis of a subject having breast cancer.

In another embodiment, the cancer markers described above are selected from a prostate cancer marker panel that includes CCL25, CCR9, CXCL13, CXCR5, CXCL16, CXCR6, CCL1, CCL4, CCL17, CCL19, CCL21, CCL22, CXCL12, CCR7, CCR8, CXCR4, CX3CR1, PSA, CEA, CGA, DHEA, NSE, PAP, prolactin and B7-H3. The markers in the breast cancer panel may be used for detecting prostate cancer or predicting the prognosis of a subject having prostate cancer.

In another embodiment, the one or more cancer markers described above are selected from a colonrectal cancer marker panel that includes CCL25, CCR9, CXCL13, CXCR5, CXCL16, CXCR6, CCL1, CCL4, CCL17, CCL19, CCL21, CCL22, CXCL12, CCR7, CCR8, CXCR4, CX3CR1, seprase polypeptide, anti-p53, osteopontin, and ferritin. The markers in the colonrectal cancer panel may be used for detecting colonrectal cancer or predicting the prognosis of a subject having colonrectal cancer.

In another embodiment, the cancer markers described above are selected from an ovarian cancer marker panel that includes CCL25, CCR9, CXCL13, CXCR5, CXCL16, CXCR6, CCL1, CCL4, CCL17, CCL19, CCL21, CCL22, CXCL12, CCR7, CCR8, CXCR4, CX3CR1, cancer antigen 125 (CA-125), HE-4, OVX-1 macrophage colony stimulating factor (M-CSF) and lysophosphatidyl choline. The markers in the ovarian cancer panel may be used for detecting ovarian cancer or predicting the prognosis of a subject having ovarian cancer.

In another embodiment, the cancer markers described above are selected from a lung cancer marker panel that includes CCL25, CCR9, CXCL13, CXCR5, CXCL16, CXCR6, CCL1, CCL4, CCL17, CCL19, CCL21, CCL22, CXCL12, CCR7, CCR8, CXCR4, CX3CR1, kinesin family member 4A (KIF4A), Neural pentraxin I (NPTX1), fibroblast growth factor receptor 1 oncogene partner (FGFR1OP) protein and CEA. The markers in the lung cancer panel may be used for detectsing lung cancer or predicting the prognosis of a subject having lung cancer.

In another embodiment, the one or more cancer markers described above are selected from a pancreatic cancer or gastric marker panel that includes CCL25, CCR9, CXCL13, CXCR5, CXCL16, CXCR6, CCL1, CCL4, CCL17, CCL19, CCL21, CCL22, CXCL12, CCR7, CCR8, CXCR4, CX3CR1 and CEA. The markers in the pancreatic cancer panel may be used for detecting pancreatic or gastric cancer or predicting the prognosis of a subject having pancreatic cancer.

In another embodiment, the one or more cancer markers described above are selected from a brain cancer, pituitary cancer, bone cancer, pancratic cancer or gastric marker panel that comprises one or more cancer markers selected from the group consisting of CCL1, CCL2, CCL4, CCL17, CCL19, CCL21, CCL22, CXCL12, CXCL13, CXCL16, CX3CL1, CCR2, CCR7, CCR8, CXCR4, CXCR5, CXCR6 and CX3CR1.

Detection Methods

The expression of the cancer marker(s) can be determined at the transcription level (i.e., the amount of mRNA) or the translation level (i.e., the amount of protein). In certain embodiments, expression of the cancer marker(s) is determined at the mRNA level by quantitative RT-PCR, Northern blot or other methods known to a person of ordinary skill in the art. In other embodiments, the expression of the cancer marker(s) is determined at the protein level by ELISA, Western blot or other types of immuno-detection methods using anti-cancer marker antibodies, such as anti-CCL25 and anti-CCR9 antibodies, anti-CXCL13 and anti-CXCR5 antibodies, and anti-CXCL16 and anti-CXCR6 antibodies.

In certain embodiments, the anti-CCL25 and/or anti-CCR9 antibodies include antibodies that bind specifically to a CCL25 peptide or a CCR9 peptide. Examples of the CCL25 peptides include, but are not limited to, peptides consisting of, or comprising, one or more sequences selected from the group consisting of LAYHYPIGWAVL (SEQ ID NO:116), KRHRKVCGNPKSREVQRAMKLLDARNKVFAKLHH (SEQ ID NO:117), FEDCCLAYHYPIGWAVLRRA (SEQ ID NO:118), IQEVSGSCNLPAAIFYLPKRHRKVCGN (SEQ ID NO:119), AMKLLDAR (SEQ ID NO:120), KVFAKLHHN (SEQ ID NO:121), QAGPHAVKKL (SEQ ID NO:122), FYLPKRHRKVCGNP (SEQ ID NO:123) YLPKRHRKVCGNPK (SEQ ID NO:124), LPKRHRKVCGNPKS (SEQ ID NO:125), PKRHRKVCGNPKSR (SEQ ID NO:126), CGNPKSREVQRAMK (SEQ ID NO:127), GNPKSREVQRAMKL (SEQ ID NO:128), KFSNPISSSKRNVS (SEQ ID NO:129), PKSREV (SEQ ID NO:130), LHHNTQT (SEQ ID NO:131) and SSSKRN (SEQ ID NO:132). Examples of the CCR9 peptides include, but are not limited to, peptides consisting of, or comprising, one or more sequences selected from the group consisting of QFASHFLPP (SEQ ID NO:133), AAADQWKFQ (SEQ ID NO:134), TFMCKVVNSM (SEQ ID NO:135), IAICTMVYPS (SEQ ID NO:136) and VQTIDAYAMFISNCAVSTNIDICFQ (SEQ ID NO:137).

In other embodiments, the anti-CXCL13 and/or anti-CXCR5 antibodies include antibodies that bind specifically to a CXCL13 peptide or a CXCR5 peptide. Examples of the CXCL13 peptides include, but are not limited to, peptides consisting of, or comprising, one or more sequences selected from the group consisting of RSSSTLPVPVFKRKIP (SEQ ID NO:45), PRGNGCPRKEIIVWKK (SEQ ID NO:46), LPRGNGCPRKEIIVWK (SEQ ID NO:47), QILPRGNGCPRKEIIV (SEQ ID NO:48), ILPRGNGCPRKEIIVW (SEQ ID NO:49), RIQILPRGNGCPRKEI (SEQ ID NO:50), RGNGCPRKEIIVWKKN (SEQ ID NO:51), KRSSSTLPVPVFKRKI (SEQ ID NO:52), IQILPRGNGCPRKEII (SEQ ID NO:53), DRIQILPRGNGCPRKE (SEQ ID NO:54), RKRSSSTLPVPVFKRK (SEQ ID NO:55), RCRCVQESSVFIPRRF (SEQ ID NO:56), GNGCPRKEIIVWKKNK (SEQ ID NO:57), CVQESSVFIPRRFIDR (SEQ ID NO:58), IDRIQILPRGNGCPRK (SEQ ID NO:59), LRCRCVQESSVFIPRR (SEQ ID NO:60), FIDRIQILPRGNGCPR (SEQ ID NO:61), RCVQESSVFIPRRFID (SEQ ID NO:62), CRCVQESSVFIPRRFI (SEQ ID NO:63), QESSVFIPRRFIDRIQ (SEQ ID NO:64), RFIDRIQILPRGNGCP (SEQ ID NO:65), VQESSVFIPRRFIDRI (SEQ ID NO:66), ESSVFIPRRFIDRIQI (SEQ ID NO:67), SLRCRCVQESSVFIPR (SEQ ID NO:68), NGCPRKEIIVWKKNKS (SEQ ID NO:69), PQAEWIQRMMEVLRKR (SEQ ID NO:70), RRFIDRIQILPRGNGC (SEQ ID NO:71), LRKRSSSTLPVPVFKR (SEQ ID NO:72), VQESSVFIPRR (SEQ ID NO:73, EWIQRMMEVLRKRSSSTLPVPVFKRK (SEQ ID NO:74), KKNK (SEQ ID NO:75), RKRSSS (SEQ ID NO:76), RGNGCP (SEQ ID NO:77), VYYTSLRCRCVQESSVFIPRR (SEQ ID NO:78), DRIQILP (SEQ ID NO:79), RKEIIVW (SEQ ID NO:80) and KSIVCVDPQ (SEQ ID NO:81). Examples of the CXCR5 peptides include, but are not limited to, peptides consisting of, or comprising, one or more sequences selected from the group consisting of TSLVENHLCPATE (SEQ ID NO:82), EGSVGWVLGTFLCKT (SEQ ID NO:83), LPRCTFS (SEQ ID NO:84), LARLKAVDNT (SEQ ID NO:85) and MASFKAVFVP (SEQ ID NO:86).

The anti-CXCL16 and/or anti-CXCR6 antibodies include antibodies that bind specifically to a CXCL16 peptide or a CXCR6 peptide. Examples of the CXCL16 peptides include, but are not limited to, peptides consisting of, or comprising, one or more sequences selected from the group consisting of AAGPEAGENQKQPEKN (SEQ ID NO:87), SQASEGASSDIHTPAQ (SEQ ID NO:88), STLQSTQRPTLPVGSL (SEQ ID NO:89), SWSVCGGNKDPWVQEL (SEQ ID NO:90), GPTARTSATVPVLCLL (SEQ ID NO:91), SGIVAHQKHLLPTSPP (SEQ ID NO:92), RLRKHL (SEQ ID NO:93), LQSTQRP (SEQ ID NO:94), SSDKELTRPNETT (SEQ ID NO:95), AGENQKQPEKNA (SEQ ID NO:96), NEGSVT (SEQ ID NO:97), ISSDSPPSV (SEQ ID NO:98), CGGNKDPW (SEQ ID NO:99), LLPTSPPISQASEGASSDIHT (SEQ ID NO:100), STQRPTLPVGSLSSDKELTRPNETTIHT (SEQ ID NO:101), SLAAGPEAGENQKQPEKNAGPTARTSA (SEQ ID NO:102), TGSCYCGKR (SEQ ID NO:103), DSPPSVQ (SEQ ID NO:104), RKHLRAYHRCLYYTRFQLLSWSVCGG (SEQ ID NO:105), WVQELMSCLDLKECGHAYSGIVAHQKHLLPTSPPISQ (SEQ ID NO:106), SDIHTPAQMLLSTLQ (SEQ ID NO:107), RPTLPVGSL (SEQ ID NO:108), TAGHSLAAG (SEQ ID NO:109), GKRISSDSPPSVQ (SEQ ID NO:110) and KDPWVQELMSCLDLKECGHAYSGIVAHQKH (SEQ ID NO:111). Examples of the CXCR6 peptides include, but are not limited to, peptides consisting of, or comprising, one or more sequences selected from the group consisting of HQDFLQFSKV (SEQ ID NO:112), AGIHEWVFGQVMCK (SEQ ID NO:113), PQIIYGNVFNLDKLICGYHDEAI (SEQ ID NO:114) and YYAMTSFHYTIMVTEA (SEQ ID NO:115).

In one embodiment, the antibody is conjugated to a solid support. By "solid support" is meant a non-aqueous matrix to which an antibody of the present application can adhere or attach. Examples of solid phases encompassed herein include those formed partially or entirely of glass (e.g., controlled pore glass), polysaccharides (e.g., agarose), polyacrylamides, silicones, and plastics such as polystyrene, polypropylene and polyvinyl alcohol.

Enzyme-linked Immunosorbent Assay (ELISA)

In certain embodiments, the cancer markers are detected using enzyme-linked immunosorbent assay (ELISA) which is typically carried out using antibody coated assay plate or wells. Commonly used ELISA assay employs either a sandwich immunoassay or a competitive binding immunoassay.

Briefly, a sandwich immunoassay is a method using two antibodies, which bind to different sites on the antigen or ligand. The primary antibody, which is highly specific for the antigen, is attached to a solid surface. The antigen is then added followed by addition of a second antibody referred to as the detection antibody. The detection antibody binds the antigen to a different epitope than the primary antibody. As a result the antigen is 'sandwiched' between the two antibodies. The antibody binding affinity for the antigen is usually the main determinant of immunoassay sensitivity. As the antigen concentration increases the amount of detection antibody increases leading to a higher measured response. The standard curve of a sandwich-binding assay has a positive slope. To quantify the extent of binding different reporters can be used. Typically an enzyme is attached to the secondary antibody which must be generated in a different species than primary antibodies (i.e. if the primary antibody is a rabbit antibody than the secondary antibody would be an anti-rabbit from goat, chicken, etc., but not rabbit). The substrate for the enzyme is added to the reaction that forms a colorimetric readout as the detection signal. The signal generated is proportional to the amount of target antigen present in the sample.

The antibody linked reporter used to measure the binding event determines the detection mode. A spectrophotometric plate reader may be used for colorimetric detection. Several types of reporters have been recently developed in order to increase sensitivity in an immunoassay. For example, chemiluminescent substrates have been developed which further amplify the signal and can be read on a luminescent plate reader. Also, a fluorescent readout where the enzyme step of the assay is replaced with a fluorophor tagged antibody is becoming quite popular. This readout is then measured using a fluorescent plate reader.

A competitive binding assay is based upon the competition of labeled and unlabeled ligand for a limited number of antibody binding sites. Competitive inhibition assays are often used to measure small analytes. These assays are also used when a matched pair of antibodies to the analyte does not exist. Only one antibody is used in a competitive binding ELISA. This is due to the steric hindrance that occurs if two antibodies would attempt to bind to a very small molecule. A fixed amount of labeled ligand (tracer) and a variable amount of unlabeled ligand are incubated with the antibody. According to law of mass action the amount of labeled ligand is a function of the total concentration of labeled and unlabeled ligand. As the concentration of unlabeled ligand is increased, less labeled ligand can bind to the antibody and the measured response decreases. Thus the lower the signal, the more unlabeled analyte there is in the sample. The standard curve of a competitive binding assay has a negative slope.

Microbeads

In certain other embodiments, the cancer markers are detected using antibody coated microbeads. In some embodiments, the microbeads are magnetic beads. In other embodiments, the beads are internally color-coded with fluorescent dyes and the surface of the bead is tagged with an anti-cancer marker antibody (e.g., an anti-CCL25 or anti-CCR9 antibody) that can bind a cancer marker in a test sample. The cancer marker, in turn, is either directly labeled with a fluorescent tag or indirectly labeled with an anti-marker antibody conjugated to a fluorescent tag. Hence, there are two sources of color, one from the bead and the other from the fluorescent tag. Alternatively, the beads can be internally coded by different sizes.

By using a blend of different fluorescent intensities from the two dyes, as well as beads of different sizes, the assay can measure up to hundreds of different cancer markers. During the assay, a mixture containing the color/size-coded beads, fluorescence labeled anti-marker antibodies, and the sample are combined and injected into an instrument that uses precision fluidics to align the beads. The beads then pass through a laser and, on the basis of their color or size, either get sorted or measured for color intensity, which is processed into quantitative data for each reaction.

When samples are directly labeled with fluorophores, the system can read and quantitate only fluorescence on beads without removing unbound fluorophores in solution. The assays can be multiplexed by differentiating various colored or sized beads. Real time measurement is achievable when a sample is directly required for unlabeled samples. Standard assay steps include incubation of a sample with anti-marker antibody coated beads, incubation with biotin or fluorophore-labeled secondary antibody, and detection of fluorescence signals. Fluorescent signals can be developed on bead (by adding streptavidin-fluorophore conjugates for biotinylated secondary antibody) and read out by a bead analyzer. Depending on the anti-marker immobilized on the bead surface, a bead-based immunoassay can be a sandwich type or a competitive type immunoassay.

Test Stick

In some other embodiments, the cancer markers in a liquid biosample are detected using a test stick. The test stick typically contains a fluid impermeable housing and a fluid permeable "stick" having one or more detection zones. In one embodiment, each detection zone contains a dried binding reagent that binds to a cancer marker in a biosample. In another embodiment, the dried binding reagent is a labeled binding reagent. In another embodiment, the test stick may further comprise a control zone to indicate that the assay test has been carried out satisfactorily, namely the reagents were present in the test stick and that they become mobilized during running the test and have been transported along the flow path. The control zone can also indicate that the reagents within the device are capable of immunochemical interactions, confirming the chemical integrity of the device. This is important when considering the storage and shipment of the device under desiccated conditions within a certain temperature range. The control zone is typically positioned downstream from the detection zone(s) and may, for example, comprise an immobilized binding reagent for a labeled binding reagent. The labeled binding reagent may be present in a mobilizable form upstream from the control zone and detection zone. The labeled binding reagent may be the same or different to the labeled binding reagent for the cancer marker.

In one embodiment, the test stick comprise a porous sample receiver in fluid connection with and upstream from one or more flow-paths. The porous sample receiver may be common to all assays. Thus a fluid sample applied to the common sample application region of the device is able to travel along the one or more flow-paths to the respective detection zones. The porous sample receiver may be provided within a housing or may at least partially extend out of said housing and may serve for example to collect a body fluid. The porous sample receiver may also act as a fluid reservoir. The porous sample receiving member can be made from any bibulous, porous or fibrous material capable of absorbing liquid rapidly. The porosity of the material can be unidirectional (i.e. with pores or fibers running wholly or predominantly parallel to an axis of the member) or multidirectional (omnidirectional, so that the member has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. Other suitable materials include glass-fiber.

If desired, an absorbent "sink" can be provided at the distal end of the carrier material. The absorbent sink may comprise, for example, Whatman 3MM chromatography paper, and should provide sufficient absorptive capacity to allow any unbound labeled binding reagent to wash out of the detection zone(s). As an alternative to such a sink it can be sufficient to have a length of porous solid phase material which extends beyond the detection zone(s).

Following the application of a binding reagent to a detection zone, the remainder of the porous solid phase material may be treated to block any remaining binding sites. Blocking can be achieved by treatment for example with protein (e.g. bovine serum albumin or milk protein), or with polyvinyl alcohol or ethanolamine, or combinations thereof. To assist the free mobility of the labeled binding reagent when the porous carrier is moistened with the sample, the porous carrier may further comprise a sugar such as sucrose or lactose and/or other substances, such as polyvinyl alcohol (PVA) or polyvinyl pyrrolidone (PVP). Such material may be deposited, for example, as an aqueous solution in the region to which the labeled binding reagent is to be applied. Such materials could be applied to the porous carrier as a first application followed by the application of the label; alternatively, such materials could be mixed with the label and applied to the porous carrier or combinations of both. Such material may be deposited upstream from or at the labeled binding reagent.

Alternatively, the porous carrier may not be blocked at the point of manufacture; instead the means for blocking the porous carrier are included in a material upstream from the porous carrier. On wetting the test strip, the means for blocking the porous carrier are mobilized and the blocking means flow into and through the porous carrier, blocking as the flow progresses. The blocking means include proteins such as BSA and casein as well as polymers such as PVP, PVA as well as sugars and detergents such as Triton-X100. The blocking means could be present in the macroporous carrier material.

The dried binding reagents may be provided on a porous carrier material provided upstream from a porous carrier material comprising the detection zone. The upstream porous carrier material may be macroporous. The macroporous carrier material should be low or non-protein-binding, or should be easily blockable by means of reagents such as BSA or PVA, to minimize non-specific binding and to facilitate free movement of the labeled reagent after the macroporous body has become moistened with the liquid sample. The macroporous carrier material can be pre-treated with a surface active agent or solvent, if necessary, to render it more hydrophilic and to promote rapid uptake of the liquid sample. Suitable materials for a macroporous carrier include plastic materials such as polyethylene and polypropylene, or other materials such as paper or glass-fiber. In the case that the labeled binding reagent is labeled with a detectable particle, the macroporous body may have a pore size at least ten times greater than the maximum particle size of the particle label. Larger pore sizes give better release of the labeled reagent. As an alternative to a macroporous carrier, the labeled binding reagent may be provided on a non-porous substrate provided upstream from the detection zone, said non-porous substrate forming part of the flow-path. In another embodiment, the test stick may further comprise a sample receiving member for receiving the fluid sample. The sample receiving member may extend from the housing.

The housing may be constructed of a fluid impermeable material. The housing will also desirably exclude ambient light. The housing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the assay provided within the interior space within the housing. Alternatively, the aperture may serve to allow a porous sample receiver to extend from the housing to a position external from the housing.

Microarray

In other embodiments, the cancer markers are detected by a protein microarray containing immobilized cancer marker-specific antibodies on its surface. The microarray can be used in a "sandwich" assay in which the antibody on the microarray captures a cancer marker in the test sample and the captured marker is detected by a labeled secondary antibody that specifically binds to the captured marker. In a preferred embodiment, the secondary antibody is biotinylated or enzyme-labeled. The detection is achieved by subsequent incubation with a streptavidin-fluorophore conjugate (for fluorescence detection) or an enzyme substrate (for colorimetric detection).

Typically, a microarray assay contains multiple incubation steps, including incubation with the samples and incubation with various reagents (e.g., primary antibodies, secondary antibodies, reporting reagents, etc.). Repeated washes are also needed between the incubation steps. In one embodiment, the microarray assays is performed in a fast assay mode that requires only one or two incubations. It is also conceivable that the formation of a detectable immune complex (e.g., a captured cancer marker/anti-marker antibody/label complex) may be achieved in a single incubation step by exposing the protein microarray to a mixture of the sample and all the necessary reagents. In one embodiment, the primary and secondary antibodies are the same antibody.

In another embodiment, the protein microarray provides a competitive immunoassay. Briefly, a microarray comprising immobilized anti-marker antibodies is incubated with a test sample in the presence of a labeled cancer marker standard. The labeled cancer marker competes with the unlabeled cancer marker in the test sample for the binding to the immobilized antigen-specific antibody. In such a competitive setting, an increased concentration of the specific cancer marker in the test sample would lead to a decreased binding of the labeled cancer marker standard to the immobilized antibody and hence a reduced signal intensity from the label.

The microarray can be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, the microarray can be processed with a ProteinArray Workstation (PerkinElmer Life Sciences, Boston, Mass.) or Assay 1200™. Workstation (Zyomyx, Hayward, Calif.). Scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images can be analyzed by stand-alone image analysis software or with image acquisition and analysis software package. For example, quantification of an antigen microarray can be achieved with a fluorescent PMT-based scanner—ScanArray 3000 (General Scanning, Watertown, Mass.) or colorimetric CCD-based scanner—VisionSpot (Allied Biotech, Ijamsville, Md.). Typically, the image analysis would include data acquisition and preparation of assay report with separate software packages. To speed up the whole assay process from capturing an image to generating an assay report, all the analytical steps including image capture, image analysis, and report generation, can be confined in and/or controlled by one software package. Such an unified control system would provide the image analysis and the generation of assay report in a user-friendly manner.

Implantable Biosensors

In other embodiments, the cancer markers are detected using implantable biosensors. Biosensors are electronic devices that produce electronic signals as the result of biological interactions. In one embodiment, the biosensors use antibodies, receptors, nucleic acids, or other members of a binding pair to bind with a cancer marker, which is typically the other member of the binding pair. Biosensors may be used with a blood sample to determine the presence of a cancer marker without the need for sample preparation and/or separation steps typically required for the automated immunoassay systems.

In one embodiment, the sensor is a nanoscale device. The sensor system includes a biological recognition element attached to a nanowire and a detector that is capable of determining a property associated with the nanowire. The biological recognition element is one member of a binding pair (e.g., a receptor of the cancer marker or an anti-cancer marker antibody) where the cancer marker being measured is the other member of the binding pair. Preferably, the nanowire sensor includes a semiconductor nanowire with an exterior surface formed thereon to form a gate electrode and a first end in electrical contact with a conductor to form a source electrode and a second end in contact with a conductor to form a drain electrode. In one embodiment the sensor is a field effect transistor comprising a substrate formed of an insulating material, a source electrode, a drain electrode and a semiconductor nanowire disposed there between with a biological recognition element attached on a surface of the nanowire. When a binding event occurs between the biological recognition element and its specific binding partner, a detectable change is caused in a current-voltage characteristic of the field effect transistor.

In another embodiment, the sensor system includes an array of sensors. One or more of the sensors in the array is associated with a protective member that prevents the associated sensor from interacting with the surrounding environment. At a selected time, the protective member may be disabled, thereby allowing the sensor to begin operating to interact with the surrounding fluid or tissue so that the biological recognition element can interact with the other member of its binding pair if that pair member is present.

In another embodiment, the protective member is formed of a conductive material that can oxidize, is biocompatible, bio-absorbable, and that may be dissolved in solution such as blood upon application of an electric potential. For example, a sensor may be farmed within a well of a substrate that is capped by a conductive material such as a biocompatible metal or an electrically-erodible polymer. In another embodiment, the protective member is formed using a material that dissolves over a predetermined period of time.

Mass Spectrometry

In other embodiments, the cancer markers are detected using mass spectrometry (MS) such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.).

Mass spectrometry methods are well known in the art and have been used to quantify and/or identify biomolecules, such as proteins. Further, mass spectrometric techniques have been developed that permit at least partial de novo sequencing of isolated proteins. In certain embodiments, a gas phase ion spectrophotometer is used. In other embodiments, laser-desorption/ionization mass spectrometry is used to analyze the sample. Modem laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. In SELDI, the substrate surface is modified so that it is an active participant in the desorption process. In one embodiment, the surface is derivatized with adsorbent and/or capture reagents that selectively bind the protein of interest. In another embodiment, the surface is derivatized with energy absorbing molecules that are not desorbed when struck with the laser. In another embodiment, the surface is derivatized with molecules that bind the protein of interest and that contain a photolytic bond that is broken upon application of the laser. In each of these methods, the derivatizing agent generally is localized to a specific location on the substrate surface where the sample is applied. The two methods can be combined by, for example, using a SELDI affinity surface to capture an analyte and adding matrix-containing liquid to the captured analyte to provide the energy absorbing material.

Detection of the presence of a cancer marker will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

A person skilled in the art understands that any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to be mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more cancer markers present in a first or second sample is determined, in part, by executing an algorithm with a computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the cancer marker that is present in the first and second samples. A standard containing a known amount of a cancer marker can be analyzed as the second sample to better quantify the amount of the biomolecule present in the first sample. In certain embodiments, the identity of the cancer markers in the first and second sample can also be determined.

Determination of Standard Value, Specificity and Sensitivity

In the present application, the standard expression level of a cancer marker, such as the blood concentration of CCL25, can be determined statistically. For example, the blood concentration of CCL25 in healthy individuals can be measured to determine the standard blood concentration of CCL25 statistically. When a statistically sufficient population can be gathered, a value in the range of twice or three times the standard deviation (S.D.) from the mean value is often used as the standard value. Therefore, values corresponding to the mean value+2×S.D. or mean value+3×S.D. may be used as standard values. The standard values set as described theoretically comprise 90% and 99.7% of healthy individuals, respectively.

Alternatively, standard values can also be set based on the actual expression level (e.g., blood concentration of CCL25) in cancer patients. Generally, standard values set this way minimize the percentage of false positives, and are selected from a range of values satisfying conditions that can maximize detection sensitivity. Herein, the percentage of false positives refers to a percentage, among healthy individuals, of patients whose blood concentration of CCL25 is judged to be higher than a standard value. On the contrary, the percentage, among healthy individuals, of patients whose blood concentration of CCL25 is judged to be lower than a standard value indicates specificity. That is, the sum of the false positive percentage and the specificity is always 1. The detection sensitivity refers to the percentage of patients whose blood concentration of CCL25 is judged to be higher than a standard value, among all cancer patients within a population of individuals for whom the presence of cancer has been determined.

As used herein, the term "test sensitivity" is the ability of a screening test to identify true disease, also characterized by being a test with high sensitivity has few false negatives, additionally a test independent of disease prevalence. The test sensitivity is calculated as true positive tests per total affected patients tested, expressed as a percentage.

The term "Test Specificity" is a screening test which is correctly negative in the absence of disease, has high specificity and few false positives, is independent of disease prevalence. The test specificity is calculated as true negative tests per unaffected individuals tested, expressed as a percentage.

The term "PPV" (Positive Predictive Value) is the percent of patients with positive test having disease, and thus assesses reliability of positive test. Calculation:

PPV=(True positive)/(True+False positives). 1.

The term "NPV" (Negative Predictive Value) refers to patients with negative test that do not have disease, and assesses reliability of negative test. Calculation:

NPV=(True negative)/(true and false negatives). 2.

As the relationship shown above indicates, each of the values for sensitivity, specificity, positive predictive value, and negative predictive value, which are indexes for evaluating the detection accuracy, varies depending on the standard value for judging the level of the blood concentration of CCL25.

A standard value is usually set such that the false positive ratio is low and the sensitivity is high. However, as also apparent from the relationship shown above, there is a trade-off between the false positive ratio and sensitivity. That is, if the standard value is decreased, the detection sensitivity increases. However, since the false positive ratio also increases, it is difficult to satisfy the conditions to have a "low false positive ratio". Considering this situation, for example, values that give the following predicted results may be selected as the preferable standard values in the present application: (1) standard values for which the false positive ratio is 50% or less (that is, standard values for which the specificity is not less than 50%) and (2) standard values for which the sensitivity is not less than 20%.

The standard values can be set using receiver operating characteristic (ROC) curve. An ROC curve is a graph that shows the detection sensitivity on the vertical axis and the false positive ratio (that is, "1—specificity") on the horizontal axis. A ROC curve can be obtained by plotting the changes in the sensitivity and the false positive ratio, which were obtained after continuously varying the standard value for determining the high/low degree of the blood concentration of a cancer marker, such as CCL25.

The "standard value" for obtaining the ROC curve is a value temporarily used for the statistical analyses. The "standard value" for obtaining the ROC curve can generally be continuously varied within a range that allows to cover all selectable standard values. For example, the standard value can be varied between the smallest and largest measured blood CCL25 values in an analyzed population.

Based on the obtained ROC curve, a preferable standard value to be used in the present application can be selected from a range that satisfies the above-mentioned conditions. Alternatively, a standard value can be selected based on a ROC curve produced by varying the standard values from a range that comprises most of the measured blood CCL25.

Kits for Detecting Cancer

Another aspect of the present application relates to a kit for detecting cancer, comprising: reagents for determining expression of CCL25 and/or CCR9 in a biological sample; and instructions for how to use said reagents, wherein said reagents comprise an anti-CCL25 antibody, an anti-CCR9 antibody, or both.

In a particular embodiment, said kit further comprises reagents for determining expression of CXCL13 and/or CXCR5 in a biological sample; and instructions for how to use said reagents, wherein said reagents comprise an anti-CXCL13 antibody, an anti-CXCR5 antibody, or both. In a further particular embodiment, said kit further comprises reagents for determining expression of CXCL16 and/or CXCR6 in a biological sample; and instructions for how to use said reagents, wherein said reagents comprise an anti-CXCL16 antibody, an anti-CXCR6 antibody, or both.

In another particular embodiment, said kit further comprises reagents for determining expression of CXCL16 and/or CXCR6 in a biological sample; and instructions for how to use said reagents, wherein said reagents comprise an anti-CXCL16 antibody, an anti-CXCR6 antibody, or both.

EXAMPLE 1

In Vitro Analysis of CCL25 and CCR9 Expression and Activity in Various Carcinomas As shown in FIG. 1, CCL25 is expressed by breast cancer tissue. Breast cancer tissue was stained with isotype control or anti-CCL25 antibodies. Magenta color shows CCL25 staining. An Aperio ScanScope CS system with a 40× objective captured digital images. A representative case of breast cancer indicated and immuno-intensity of CCL25.

Figure 2:
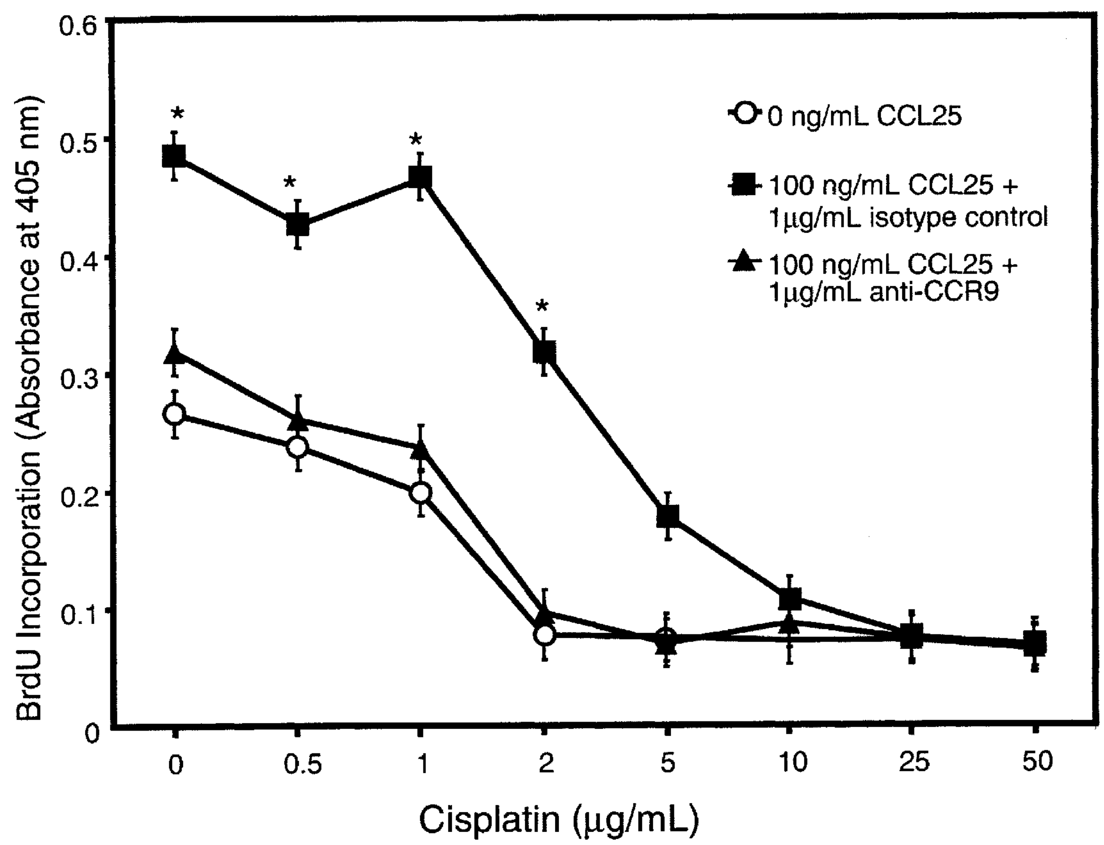
FIG. 2 shows that CCL25 inhibits cisplatin-induced reductions in breast cancer cell line growth.

FIG. 2 demonstrates CCL25 inhibition of cisplatin-induced reductions in breast cancer cell line growth is demonstrated. MDA-MB-231 cells were cultured with 0 or 100 ng/ml of CCL25 plus isotype control or anti-CCR9 Ab for 24 hours, along with increasing concentrations of cisplatin. Cell proliferation was determined by BrdU incorporation and assays were repeated 3 times and performed in triplicate. Asterisks indicate statistical significant differences ($p<0.01$) between CCL25-treated and untreated BrCa cells.

Figure 3:
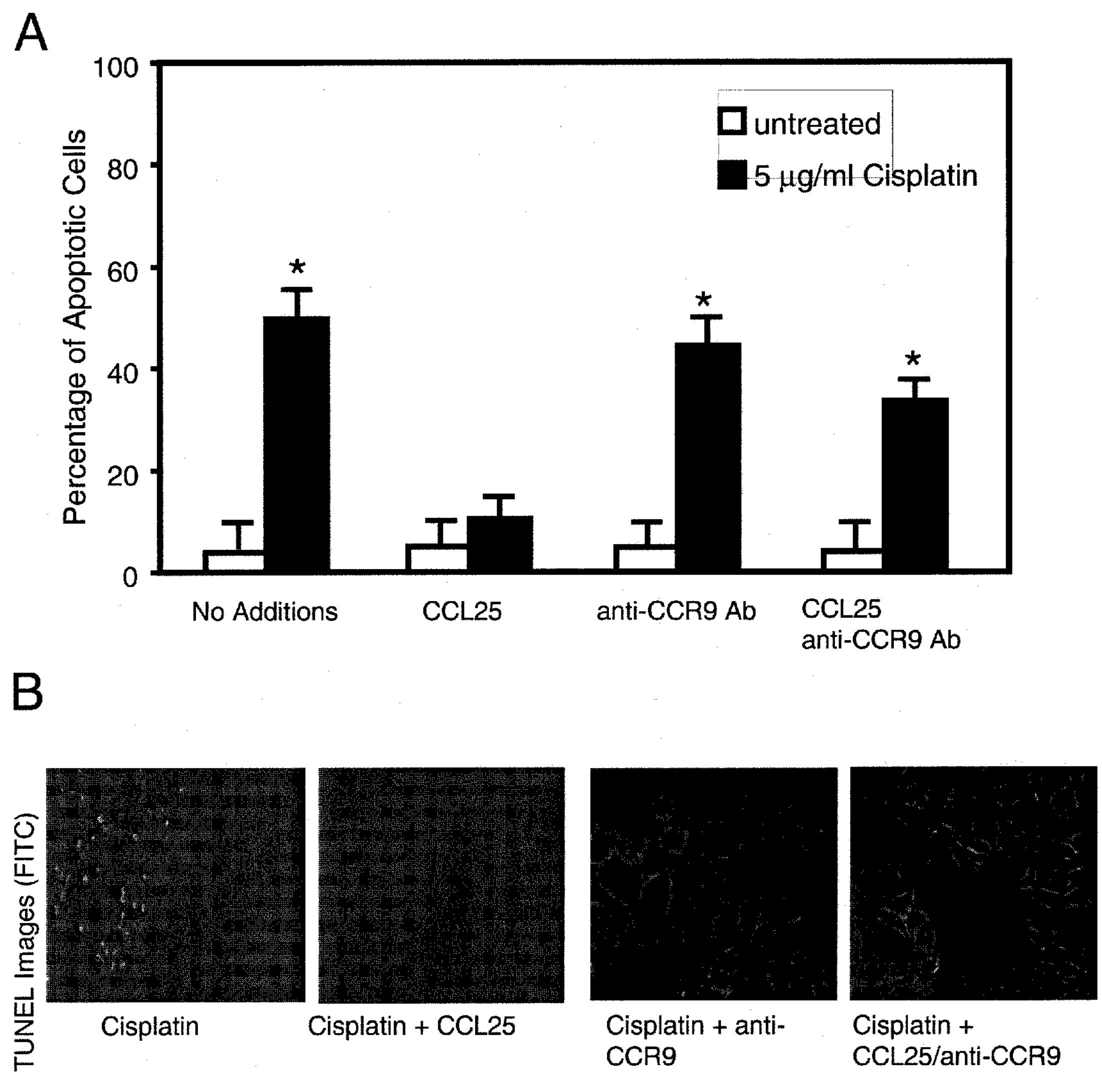
FIG. 3 shows that CCL25 protects breast cancer cells from cisplatin-induced apoptosis.

FIGS. 3A-B show that CCL25 protects breast cancer cells from cisplatin-induced apoptosis. MDA-MB-231 cells were cultured for 24 hours with 5 mg/ml of cisplatin alone or with 0 or 100 ng/ml CCL25 plus 1 mg/ml of anti-human CCR9 or isotype controls (A). Cells were harvested and stained with annexin V and propidium iodide (PI). Analysis by flow cytometry of the stained cells distinguished apoptotic (annexin V positive) cells from viable (no fluorescence) and necrotic (PI positive) cells. Asterisks indicate statistical significant differences ($p<0.01$) between CCL25-treated and untreated breast cancer cells. MDA-MB-231 cell line was cultured for 24 hours with 5 mg/ml cisplatin or with 0 or 100 ng/ml of CCL25 plus 1 mg/ml or anti-human CCR9 or isotype control Abs (B). Detection of apoptotic cells was carried out using the terminal deoxynucleotidyl transferase-mediated dUTP nick-end labeling (TUNEL) method. Apoptotic cells exhibited nuclear green fluorescence with a standard fluorescence filter set (520±20 nm). Asterisks indicate statistical significant differences ($p<0.01$) between cisplatin CCL25-treated and untreated breast cancer cell line.

Figure 4:
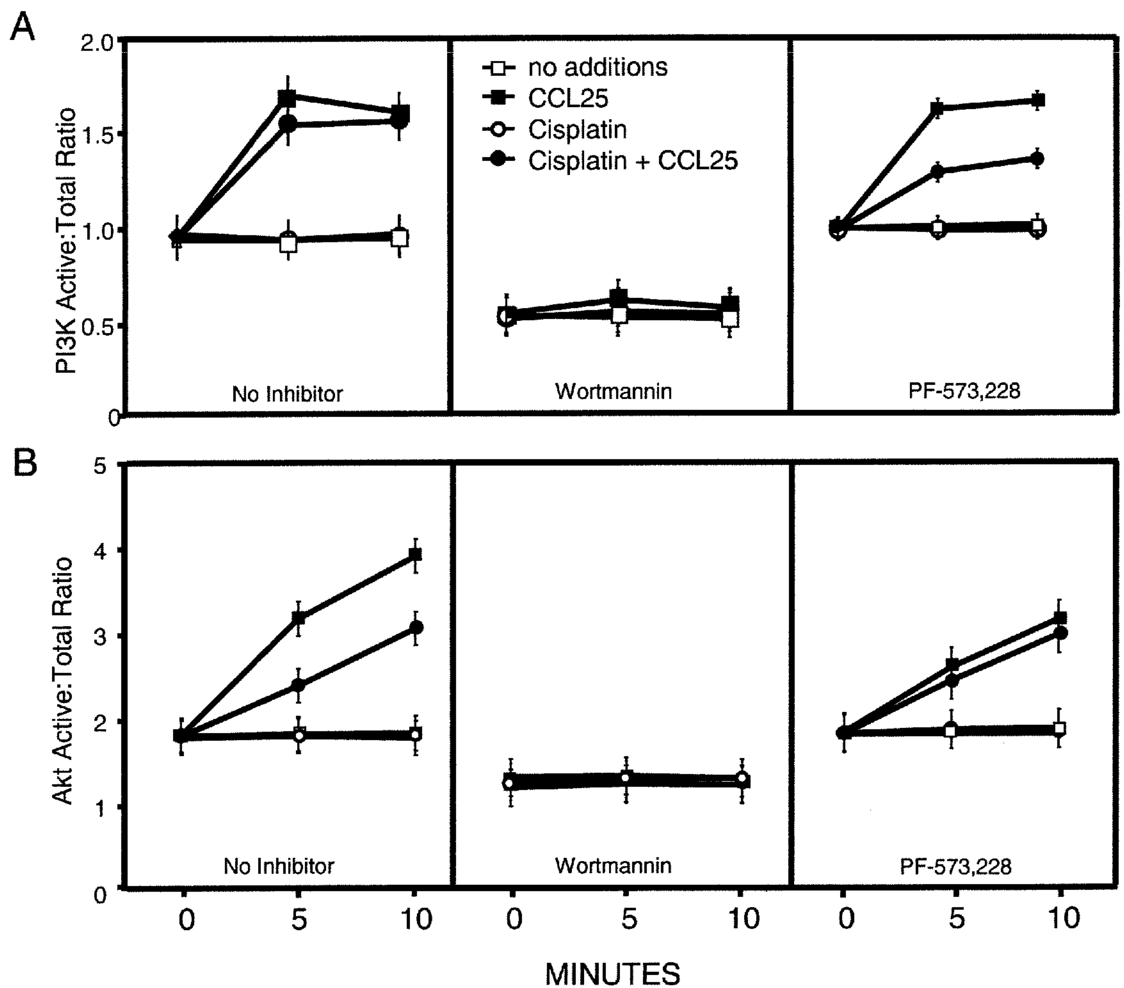
FIGS. 4A-B show PI3K and Akt activation by CCL25-CCR9 interactions in a breast cancer cell line.

FIGS. 4A-B show PI3K and Akt activation by CCL25-CCR9 interactions in a breast cancer cell line. MDA-MB-231 cells were tested for their ability to activate PI3K and Akt following treatment with CCL25, cisplatin and specific kinase inhibitors (wortmannin and PF-573,228). In situ total and phosphorylated PI3K and Akt levels were quantified by Fast Activated Cell-based ELISA before (0 minutes) or after (5 or 10 minutes) CCL25 stimulation in the presence of cisplatin and kinase inhibitors. The ratio ±SEM of active (phosphorylated) to total PI3K (A) or Akt (B) are presented in from 3 separate experiments performed in triplicate. Asterisks indicate statistical differences between untreated and CCL25-treated cells and CCL25+cisplatin-treated cells.

Figure 5:
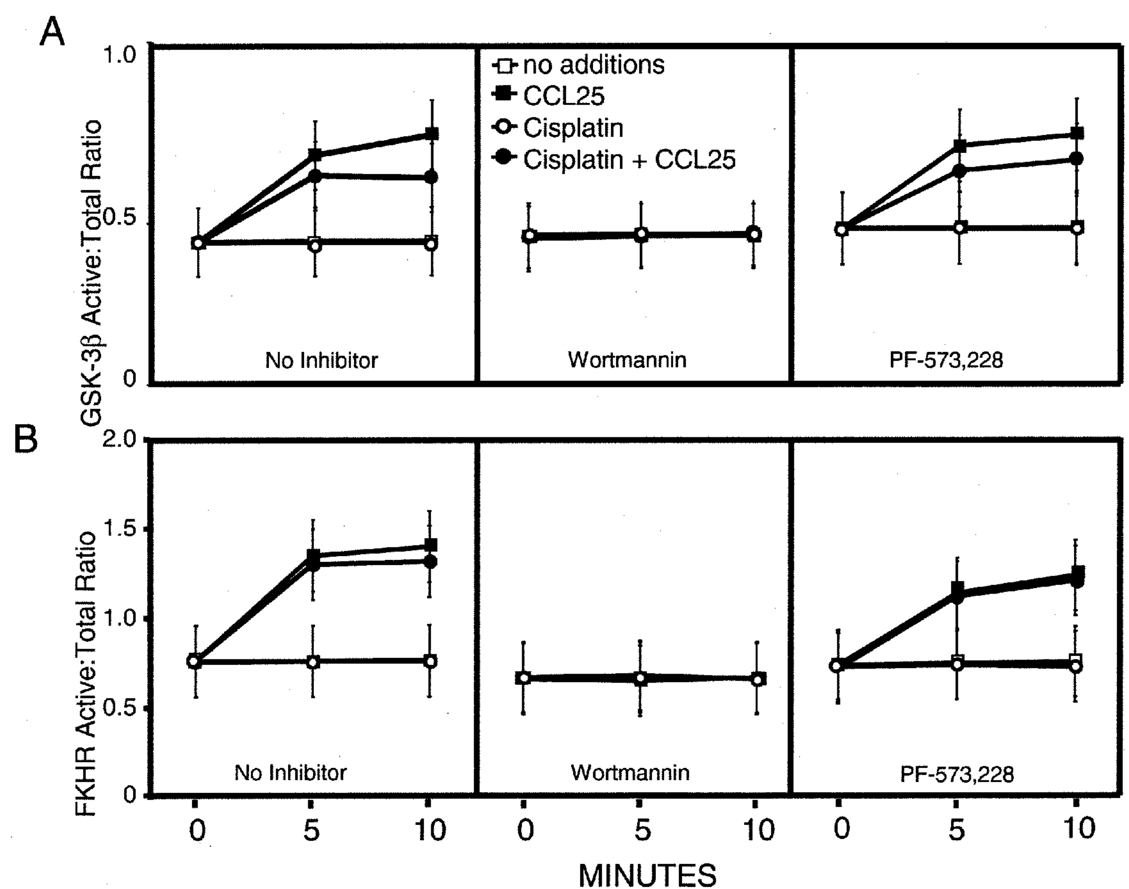
FIGS. 5A-B show GSK-3β and FKHR phosphorylation following CCL25 treatment of a breast cancer cell line.

FIGS. 5A-B show GSK-3β and FKHR phosphorylation following CCL25 treatment of a breast cancer cell line. MDA-MB-231 cells were tested for their ability to phosphorylate GSK-3β and FKHR following treatment with CCL25, cisplatin and specific-kinase inhibitors (wortmannin and PF-573,228). In situ total and phosphorylated GSK-3β and FKHR levels were quantified by Fast Activated Cell-based ELISA before (0 minutes) or after (5 or 10 minutes) CCL25 stimulation in the presence of cisplatin and kinase inhibitors. The ratio of phosphorylated to total GSK-3β (A) or FKHR (B) are presented in ±SE from 3 separate experiments performed in triplicate. Asterisks indicate statistical differences ($p<0.01$) between untreated and CCL25-treated cells and CCL25+cisplatin-treated cells.

Figure 6:
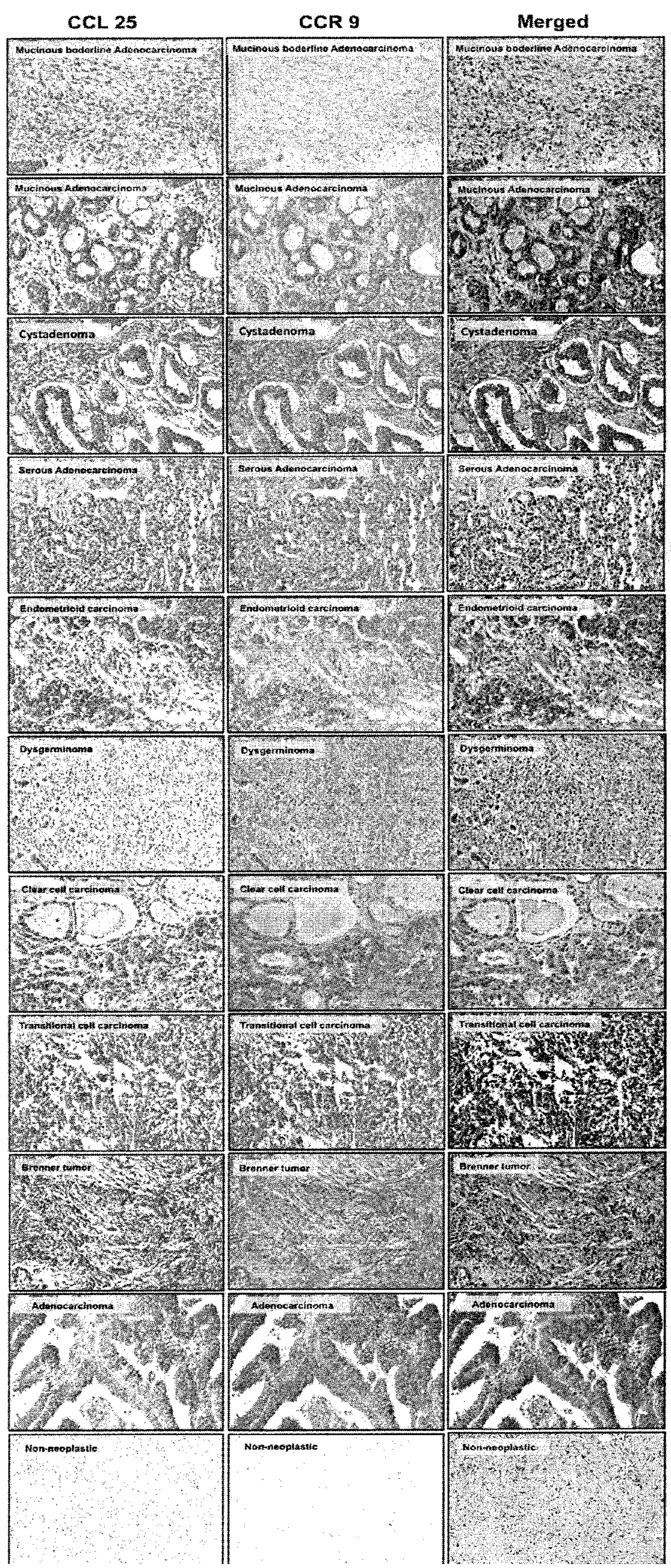
FIG. 6 shows CCR9 and CCL25 expression by ovarian cancer tissues.

FIG. 6 shows CCR9 and CCL25 expression by ovarian cancer tissues. Ovarian cancer tissues from non-neoplastic (n=8), serous adenocarcinoma (n=9), serous papillary cystadenoma (n=1), endometrioid adenocarcinoma (n=5), mucinous adenocarcinoma (n=2), Cystadenoma (n=3), mucinous boderline adenocarcinoma (n=1), clear cell carcinoma (n=5), granulosa cell tumor (n=3), dysgerminoma (n=3), transitional cell carcinoma (n=3), Brenner tumor (n=1), yolk sac tumor (n=4), adenocarcinoma (n=1) and fibroma (n=2) were stained with isotype control or anti-CCR9 and CCL25 antibodies. Brown (DAB) color shows CCR9 staining and Magenta color show CCL25. An Aperio ScanScope CS system with a 40× objective captured digital images of each slide. Representative cases show immunointensities of CCR9 and CCL25.

FIGS. 7A-B show an analysis of CCL25 expression by ovarian cancer tissues. CCL25 expression were analyzed and presented by modified box plot (A). Lower, middle and upper lines, respectively, in the box represent the first quartile (Q1), Median (Q2) and third quartile (Q3). Upper and lower whiskers represent the median ±1.5 (Q3−Q1). Significant differences from non-neoplastic are indicated in the lower panel. The table (B) shows respective p values or significant differences between non-neoplastic tissue (NN) and serous adenocarcinoma (SA), endometrioid adenocarcinoma (EC), mucinous adenocarcinoma (MA), cystadenoma (C), mucinous boderline adenocarcinoma (MBA), clear cell carcinoma (CCC), granulosa cell tumor (GCT), dysgerminoma (D), transitional cell carcinoma (TCC), Brenner tumor (BT), yolk sac tumor (YST), adenocarcinoma (A), and fibroma (F).

FIGS. 8A-B show an analysis of CCR9 expression by ovarian cancer tissues. CCR9 expression was analyzed and presented by modified box plot (A). Lower, middle and upper lines, respectively, in the box represent the first quartile (Q1), Median (Q2) and third quartile (Q3). Upper and lower whiskers represent the median ±1.5 (Q3−Q1 significant differences from non-neoplastic are indicated in the lower panel. The table (B) shows respective p values or significant differences between non-neoplastic tissue (NN) and serous adenocarcinoma (SA), endometrioid adenocarcinoma (EC), mucinous adenocarcinoma (MA), cystadenoma (C), mucinous boderline adenocarcinoma (MBA), clear cell carcinoma (CCC), granulosa cell tumor (GCT), dysgerminoma (D), transitional cell carcinoma (TCC), Brenner tumor (BT), yolk sac tumor (YST), adenocarcinoma (A), and fibroma (F).

Figure 9:
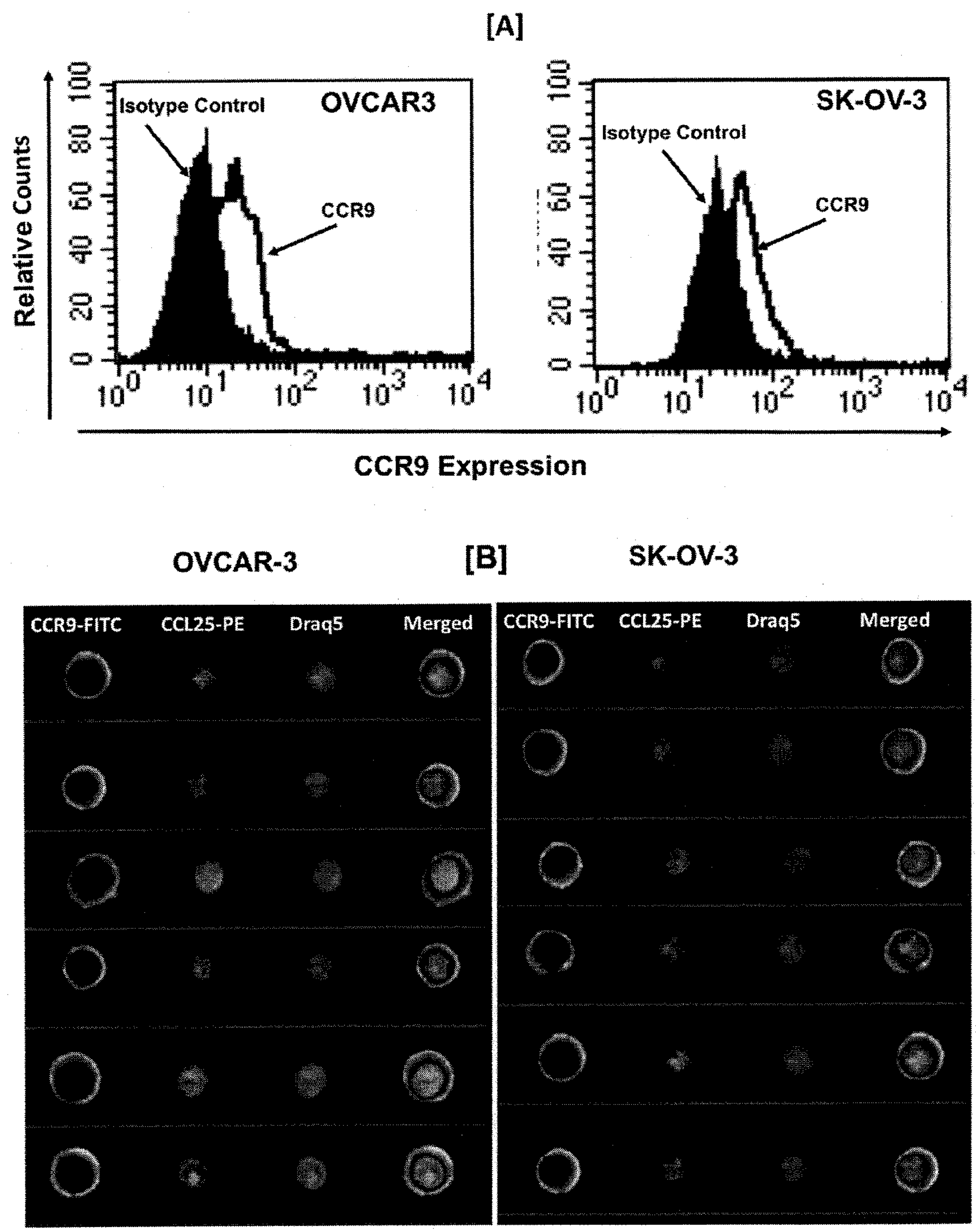
FIGS. 9A-B show CCR9 and CCL25 expression by ovarian cancer cell lines.

FIGS. 9A-B show CCR9 and CCL25 expression by ovarian cancer cell lines. Ovarian cancer cells were stained with fluorescein (FITC)-conjugated anti-CCR9 or FITC-conjugated isotype control antibody and analyzed by FACS (A). Ovarian cancer cells were stained with FITC-conjugated anti-CCR9, intracellular CCL25 was stained with phycoerythrin (PE)-conjugated anti-CCL25 antibody and nuclei were stained with Draq-5 (B). Merged data show the expression of CCR9 on the surface and CCL25 expression in the nucleus.

Figure 10:
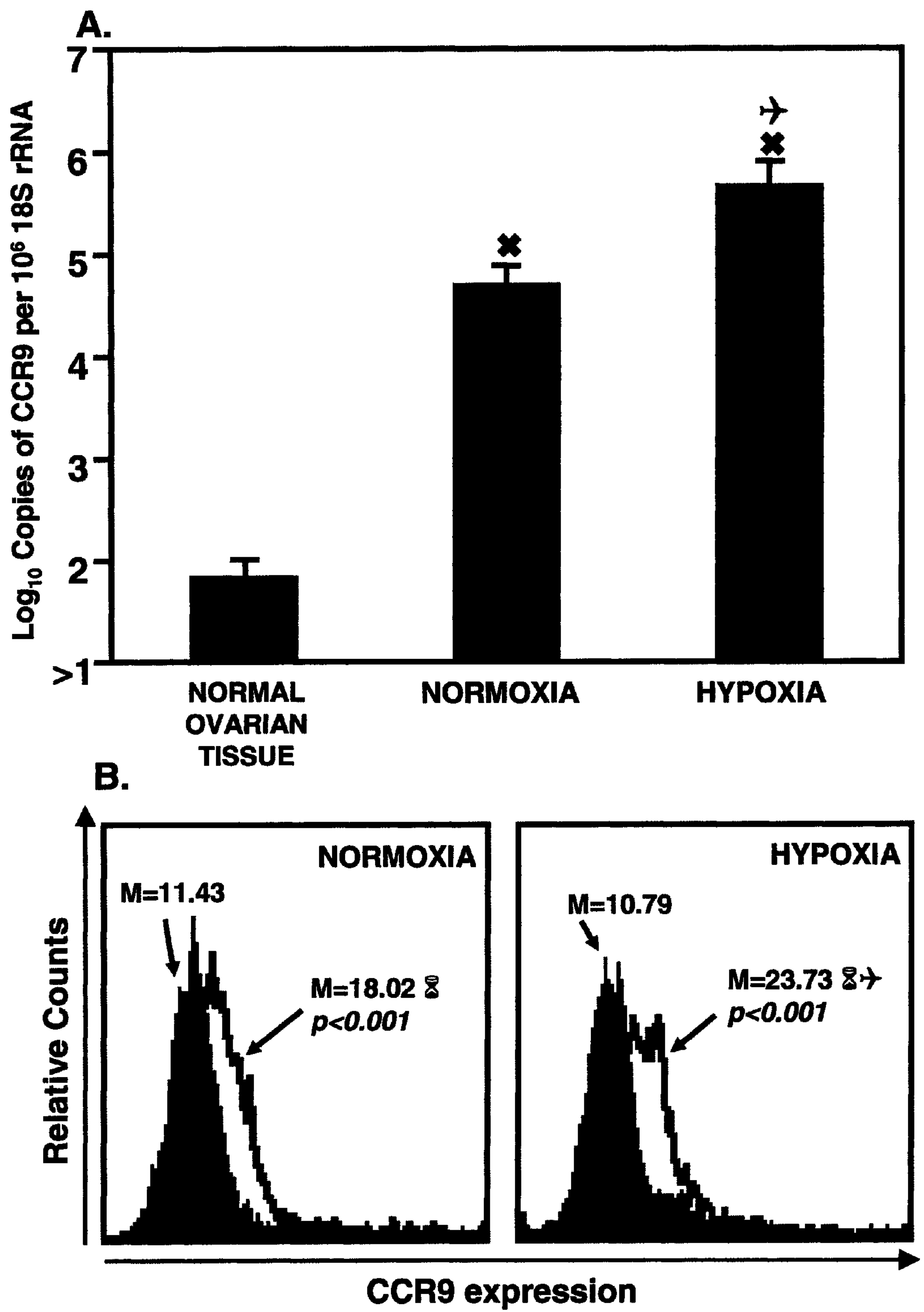
FIGS. 10A-B show hypoxia-regulated CCR9 mRNA and surface protein expression by ovarian cancer cells.

FIGS. 10A-B show hypoxia-regulated CCR9 mRNA and surface protein expression by ovarian cancer cells. Total RNA was isolated from SKOV-3 cell line under normoxic and hypoxic conditions or from normal primary ovary tissue. Quantitative RT-PCR analysis of CCR9 mRNA expression was performed in triplicate. The copies of transcripts are expressed relative to actual copies of 18S rRNA+SE (A). SKOV-3 cells under normoxia and hypoxia were stained with PE-conjugated isotype control antibody (Ab) (solid histogram) or PE-conjugated anti-CCR9 monoclonal Ab (open histogram) and quantified by flow cytometry (B). The mean fluorescent intensities of PE-positive cells are shown. Symbols indicate statistical significant ($p<0.01$) differences in CCR9 expression between normal tissue or isotype control and OvCa cells (@) or between normoxic and hypoxic cells (*).

Figure 11:
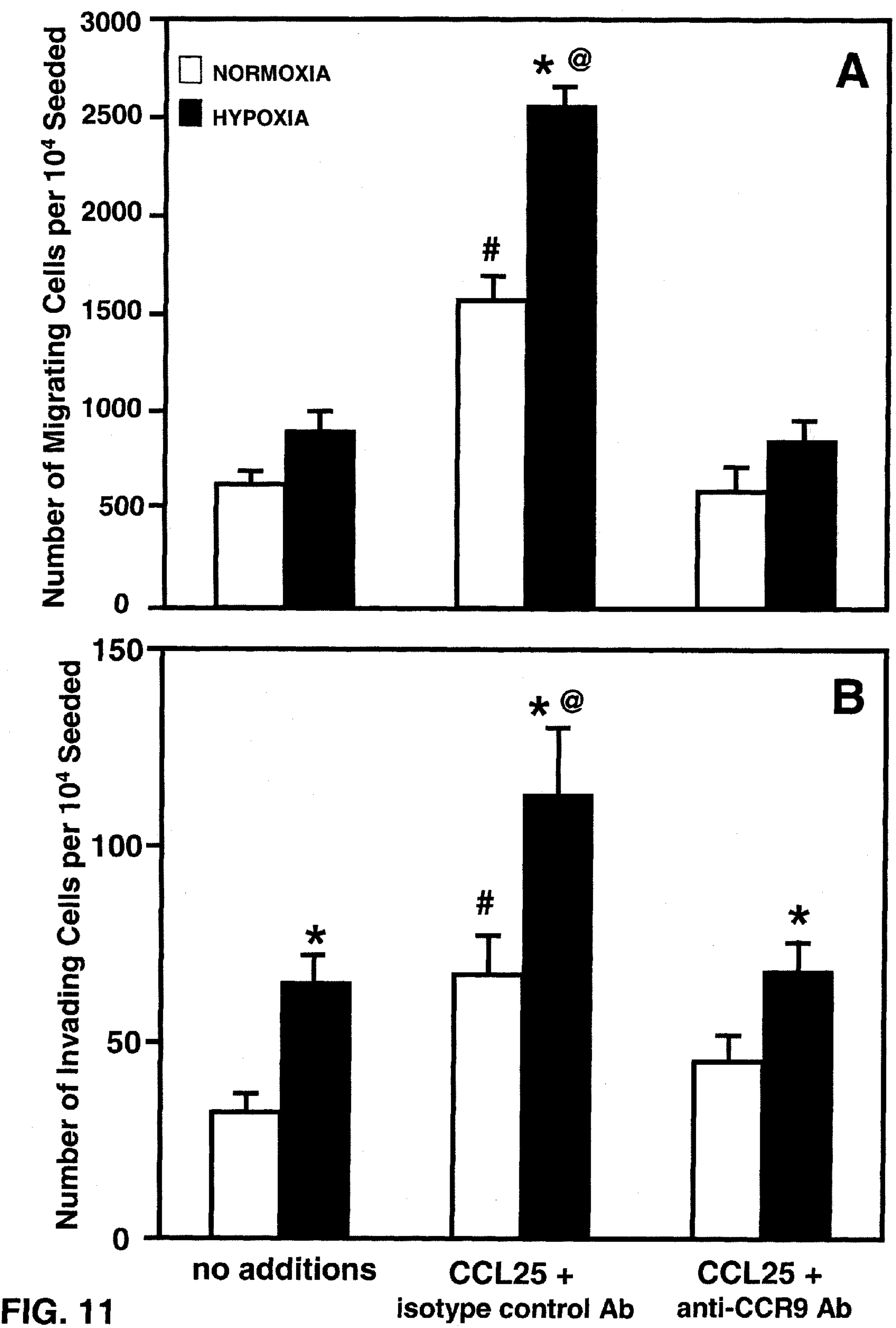
FIGS. 11A-B show hypoxia-mediated and CCL25-mediated migration and invasion of SKOV-3 cells.

FIGS. 11A-B show hypoxia-mediated and CCL25-mediated migration and invasion of SKOV-3 cells. SKOV-3 cells were tested for their ability to migrate toward chemotactic gradients of CCL25 (A). Cells were co-cultured with 1.0 μg/ml mouse anti-CCR9 antibody (Ab) or isotype control Ab during migration assays using 100 ng/ml of CCL25 under normoxic or hypoxic conditions. Also, SKOV-3 cells were tested for their ability to invade or translocate cross Matrigel™ matrix in response to 100 ng/ml of CCL25 under hypoxic or normoxic conditions (B). Cells were co-cultured with 1.0 μg/ml monoclonal antibodies against CCR9 during invasion assays using 100 ng/ml of CCL25 under normoxic or hypoxic conditions. The number of cells (+SE) that migrated or invaded is shown with symbols that indicate significant ($p<0.01$) differences between CCL25-treated and untreated normoxic cells (#), CCL25-treated and untreated hypoxic cells (@), or similarly treated normoxic and hypoxic cells (*).

Figure 12:
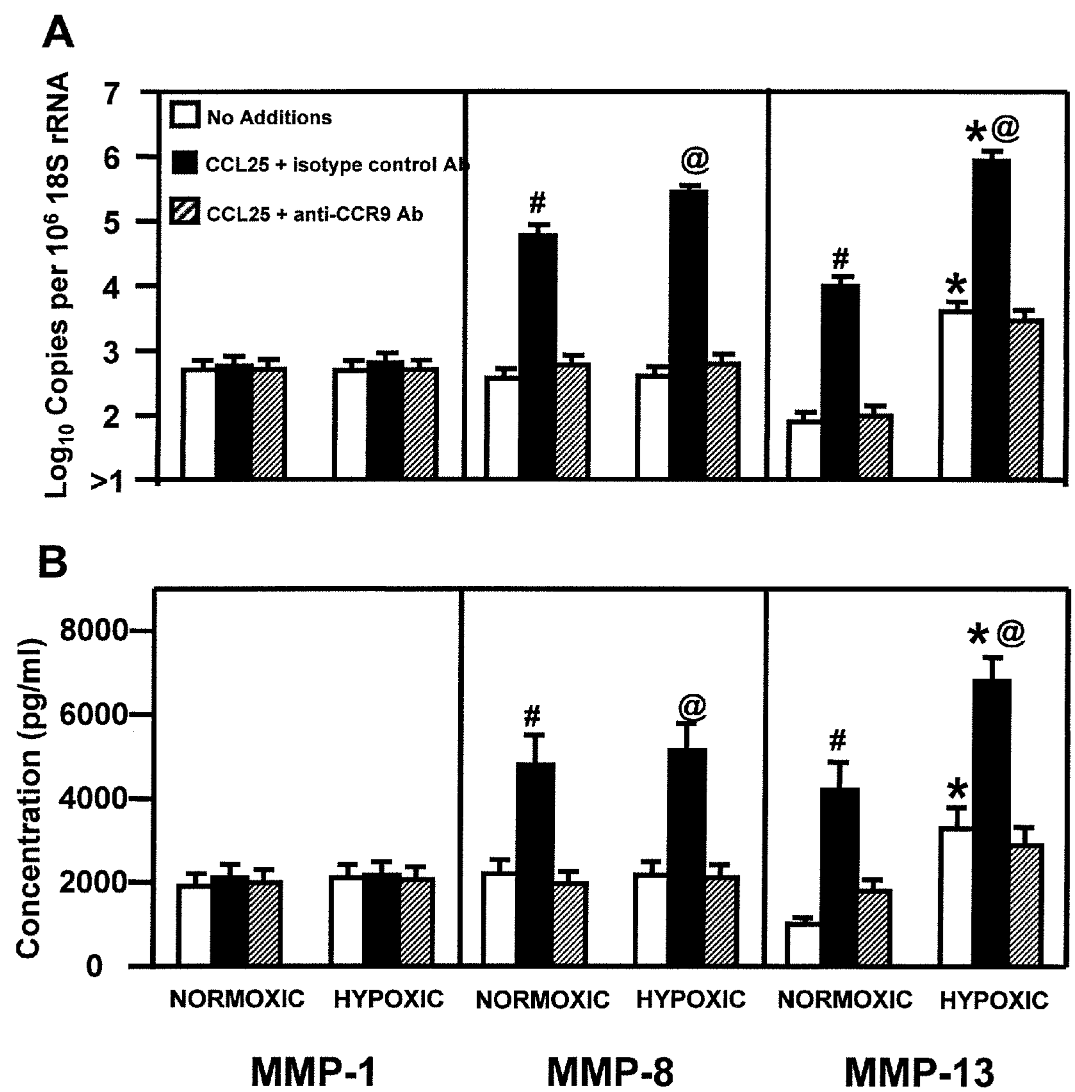
FIGS. 12A-B show CCL25-induced collagenase expression by SKOV-3 cells.

FIGS. 12A-B show CCL25-induced collagenase expression by SKOV-3 cells. Cells were tested for their ability to express collagenases (MMP-1, MMP-8, and MMP-13) mRNA and active protein. SKOV-3 cells were cultured for 24 hours alone, with 100 ng/ml of CCL25+1 μg/ml of isotype control antibody (Ab), or CCL25+1 μg/ml of mouse anti-CCR9 Ab under normoxic or hypoxic conditions. Total RNA was isolated and quantitative RT-PCR analysis was performed for mRNA expression of collagenases and transcript copies are presented relative to actual copies of 18S rRNA (A). Active collagenases were quantified by Fluorokine and Biotrak assays in conditioned media (B). Symbols indicate significant ($p<0.01$) differences between CCL25-treated and untreated normoxic cells (#), CCL25-treated and untreated hypoxic cells (@), or similarly treated normoxic and hypoxic cells (*).

Figure 13:
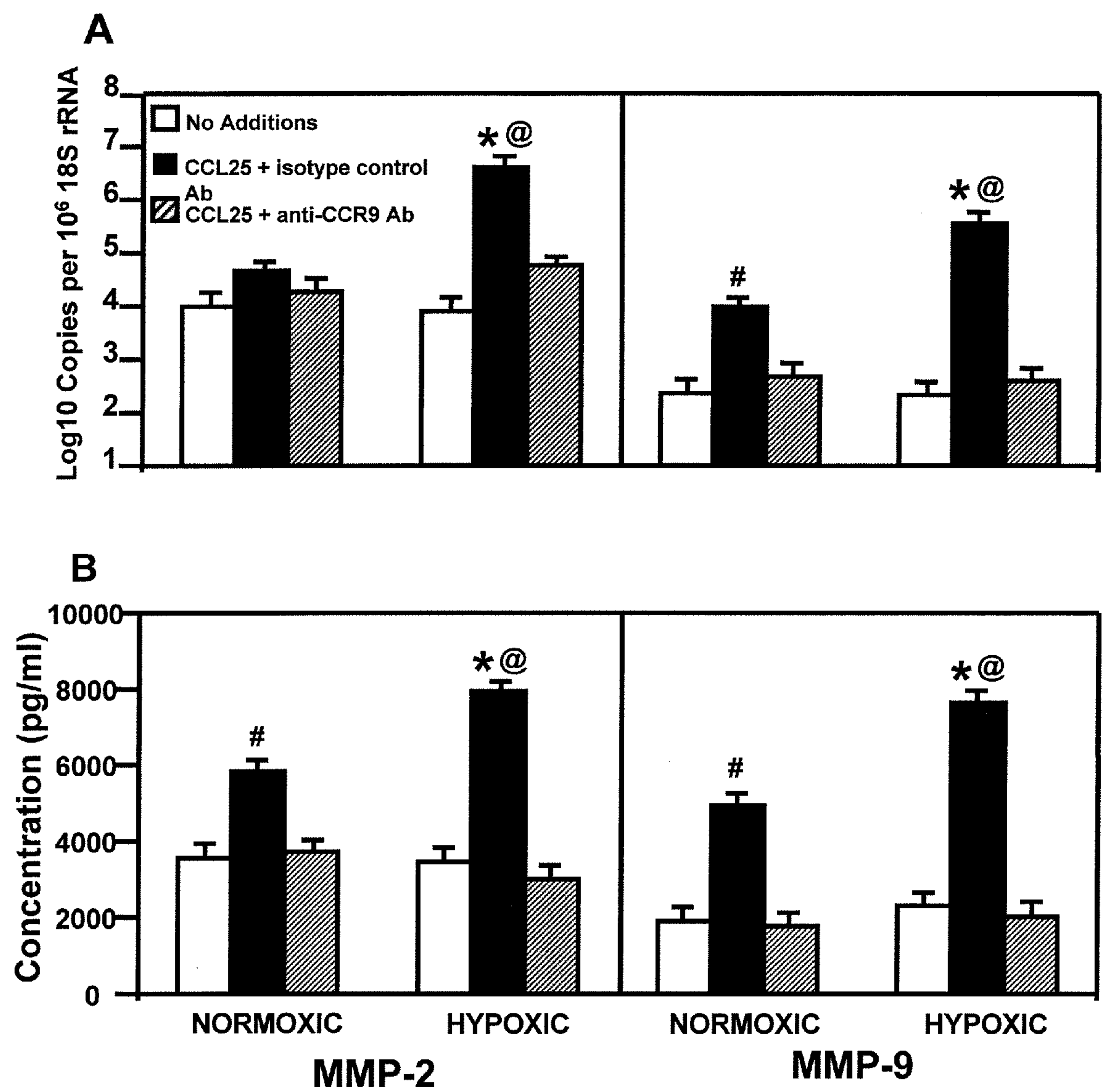
FIGS. 13A-B show CCL25-induced gelatinase expression by SKOV-3 cells.

FIGS. 13A-B show CCL25-induced gelatinase expression by SKOV-3 cells. Cells were tested for their ability to express gelatinases (MMP-2 and MMP-9) mRNA and active protein. SKOV-3 cells were cultured for 24 hours alone, with 100 ng/ml of CCL25+1 μg/ml of isotype control antibody (Ab), or CCL25+1 μg/ml of mouse anti-CCR9 Ab under normoxic or hypoxic conditions. Total RNA was isolated and quantitative RT-PCR analysis was performed for mRNA expression of gelatinases and transcript copies are presented relative to actual copies of 18S rRNA (A). Active gelatinases in conditioned media were quantified by Fluorokine and Biotrak assays (B). Symbols indicate significant ($p<0.01$) differences between CCL25-treated and untreated normoxic cells (#), CCL25-treated and untreated hypoxic cells (@), or similarly treated normoxic and hypoxic cells (*).

Figure 14:
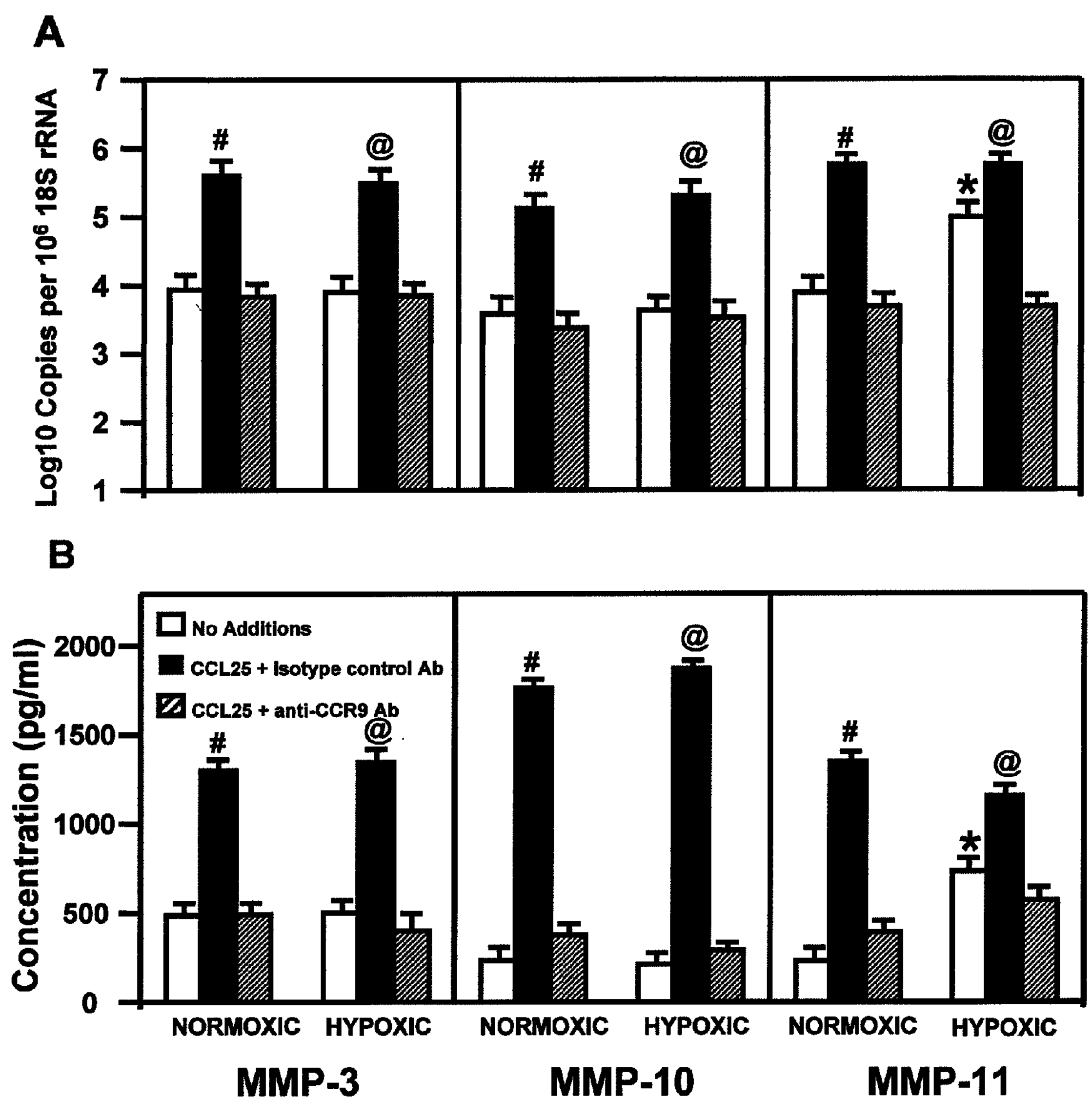
FIGS. 14A-B show CCL25-induced stromelysin expression by SKOV-3 cells.

FIGS. 14A-B show CCL25-induced stromelysin expression by SKOV-3 cells. Cells were tested for their ability to express stromelysins (MMP-3, MMP-10, and MMP-11) mRNA and active protein. SKOV-3 cells were cultured for 24 hours alone, with 100 ng/ml of CCL25+1 μg/ml of isotype control antibody (Ab), or CCL25+1 μg/ml of mouse anti-CCR9 Ab under normoxic or hypoxic conditions. Total RNA was isolated and quantitative RT-PCR analysis was performed for mRNA expression of stromelysins and transcript copies are presented relative to actual copies of 18S rRNA (A). Active stromelysins were quantified by Fluorokine and Biotrak assays in conditioned media (B). Symbols indicate significant ($p<0.01$) differences between CCL25-treated and untreated normoxic cells (#), CCL25-treated and untreated hypoxic cells (@), or similarly treated normoxic and hypoxic cells (*).

Figure 15:
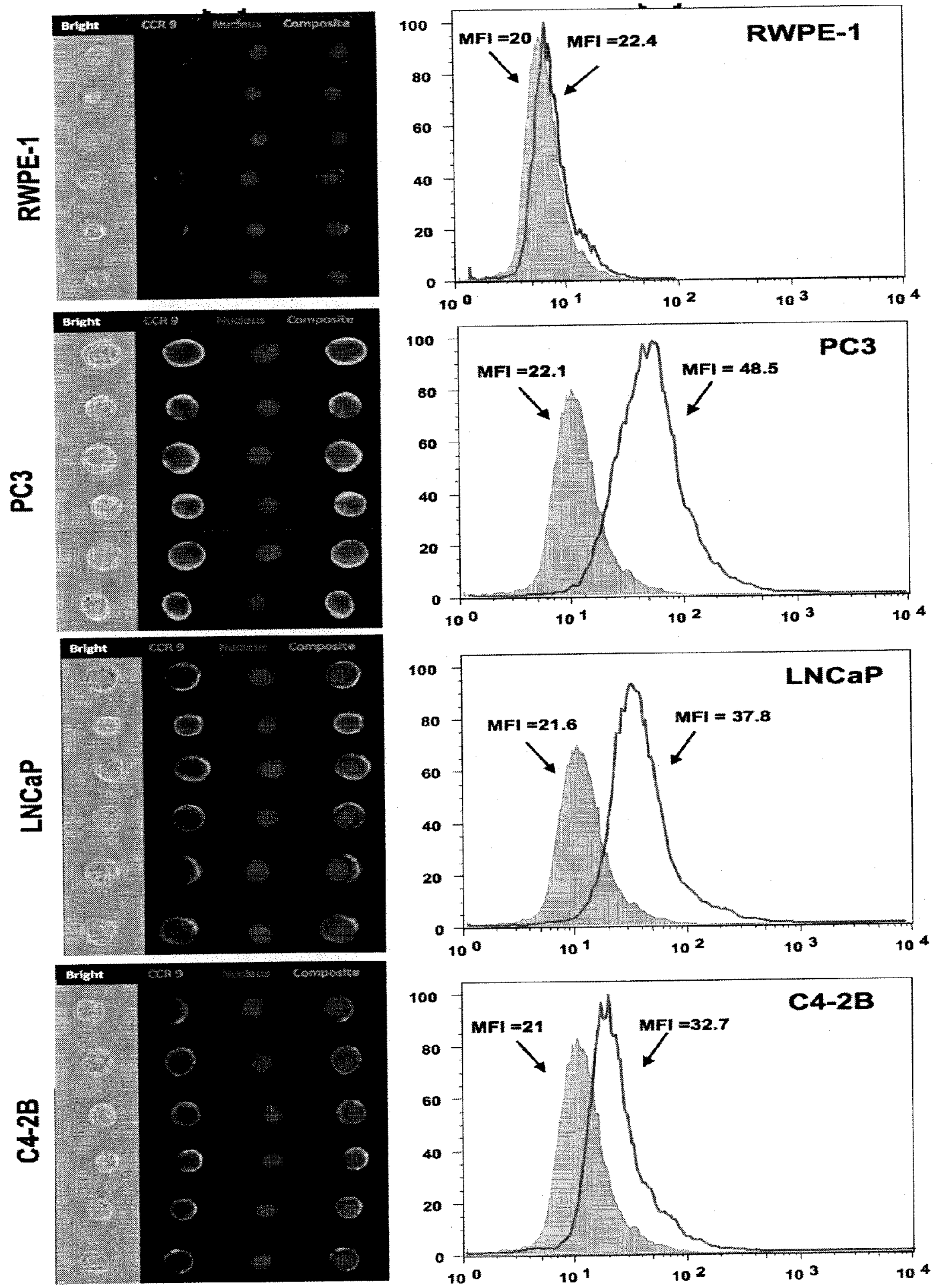
FIG. 15 shows CCR9 expression by prostate cancer cells.

FIG. 15 shows CCR9 expression by prostate cancer cell lines. Prostate cancer cell lines (C4-2B, LNCaP, and PC3) and normal prostate cells (RWPE-1) were stained with FITC-conjugated anti-human CCR9 (green) and 7AAD (nuclear stain; red). Positively stained cells were imaged and quantified by Amnis ImageStream. Panels on the right show the mean fluorescence intensity of CCR9 staining.

FIGS. 16A-D show CCR9 expression by prostate tissue. Tissue microarrays (TMA) were obtained from the National Institutes of Health (NIH), National Cancer Institute (NCI) and the University of Alabama at Birmingham and stained for CCR9. Aperio Scan Scope system with a 40× objective captured digital images of each slide. Representative cases of prostate cancer (CaP)(A), matched benign prostate tissue (MB)(B) and negative controls are indicated and intensities of CCR9 for all tissues scanned and analyzed were quantified using ImageScope software (v. 6.25). FIG. 27D shows the CCR9 immunointensity between MB, benign prostatic hyperplasia (BPH), and prostate cancer (PCa). Asterisks indicate significant ($p<0.01$) differences in CCR9 immunointensity between MB, BPH, and PCa tissue.

Figure 17:
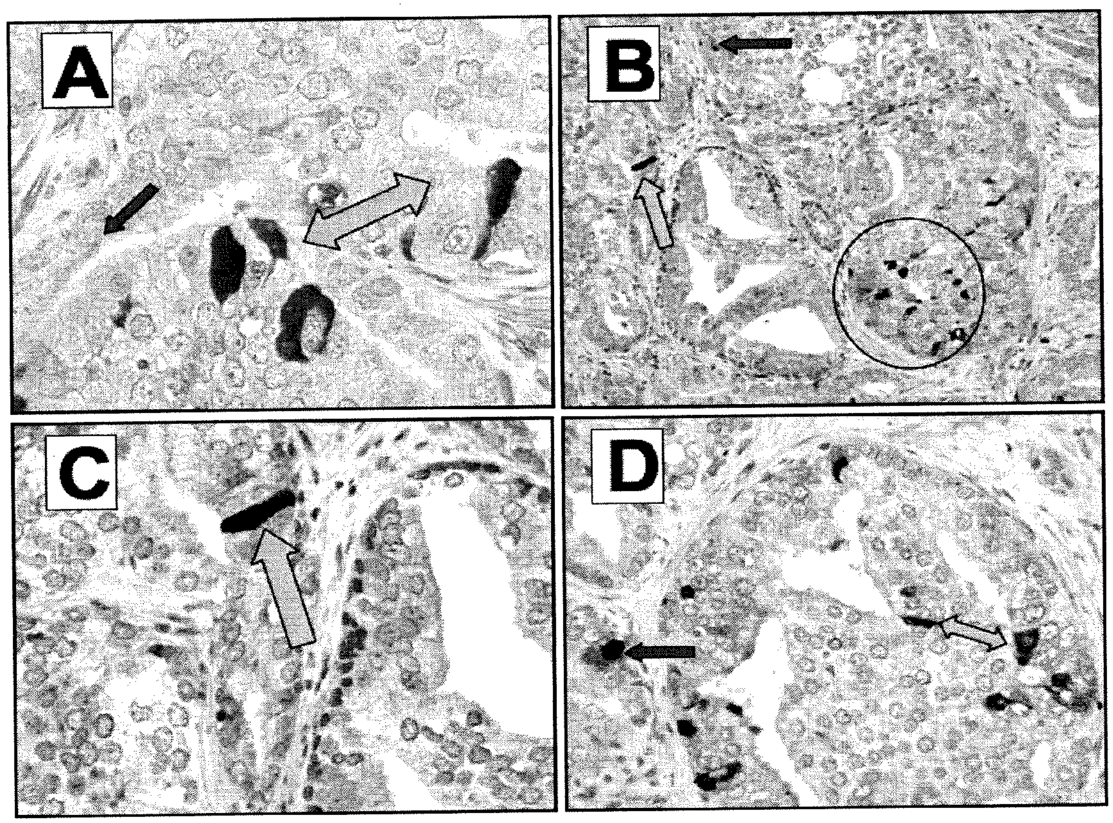
FIGS. 17A-D show CCL25 expression by prostate cancer tissue.

FIGS. 17A-D show CCL25 expression by prostate cancer tissue. Neuroendocrine differentiation of endocrine-paracrine cell phenotypes frequently occurs in prostatic malignancies and has potential prognostic and therapeutic implications. Paracrine cell phenotypes can be considered to be an androgen-insensitive, post-mitotic subpopulation in the prostate and prostate cancer. FIG. 17A demonstrates the expression of CCL25 in paracrine pattern within prostate interepithelial neoplasia. The double-headed arrow points to multiple paracrine cells producing CCL25 (red); brown arrow points cells expressing CCR9 (Brown). FIG. 17B shown cell stained red for CCL25. Brown arrow points the cell NSE. FIGS. 17A and C are higher magnifications of FIGS. 17D and B, respectively.

Figure 18:
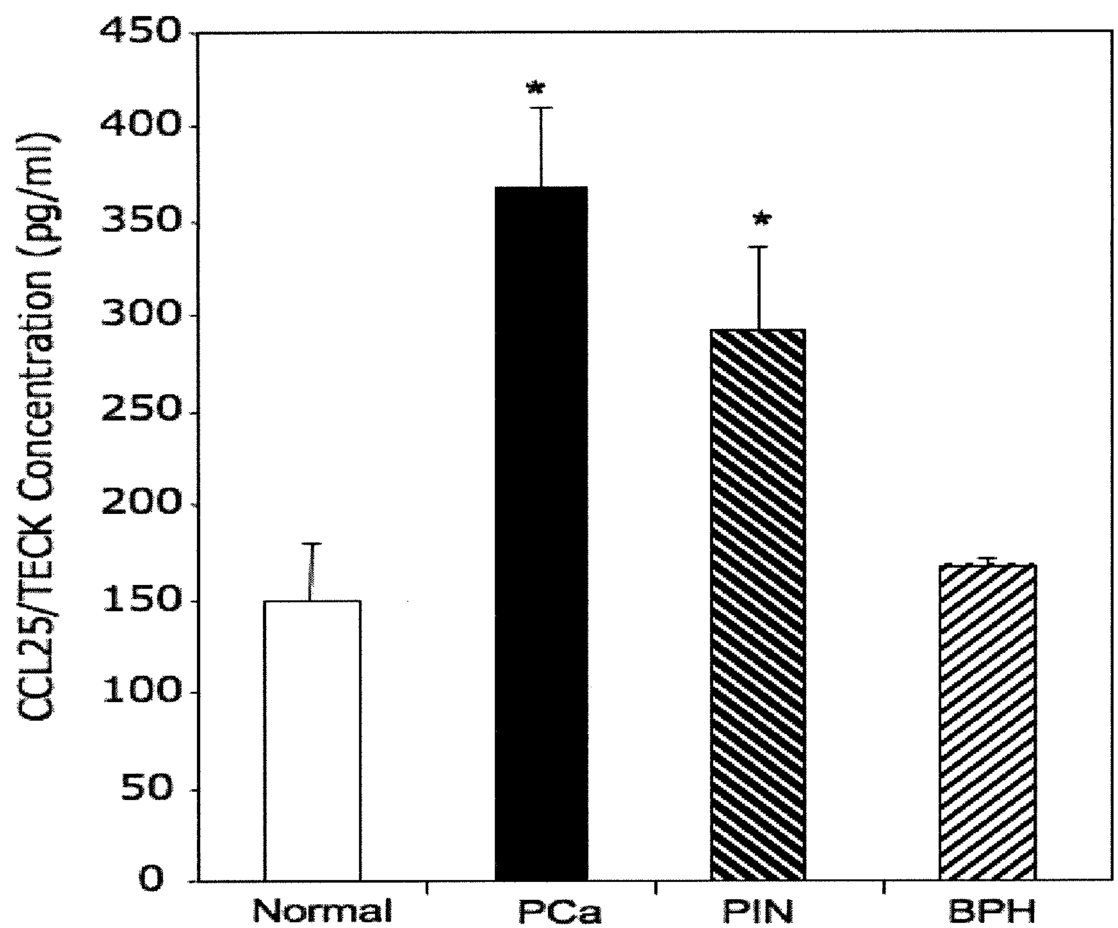
FIG. 18 shows serum CCL25 levels in normal healthy donors or patients with prostatic disease.

FIG. 18 shows serum CCL25 levels in normal healthy donors or patients with prostatic disease. ELISA was used to quantify CCL25 in serum from normal healthy donors, prostate cancer (PCa), prostate interepithelial neoplasia (PIN), and benign prostate hyperplasia (BPH). Asterisks indicate significant differences ($p<0.05$) of CCL25 levels compared to normal healthy donors.

Figure 19:
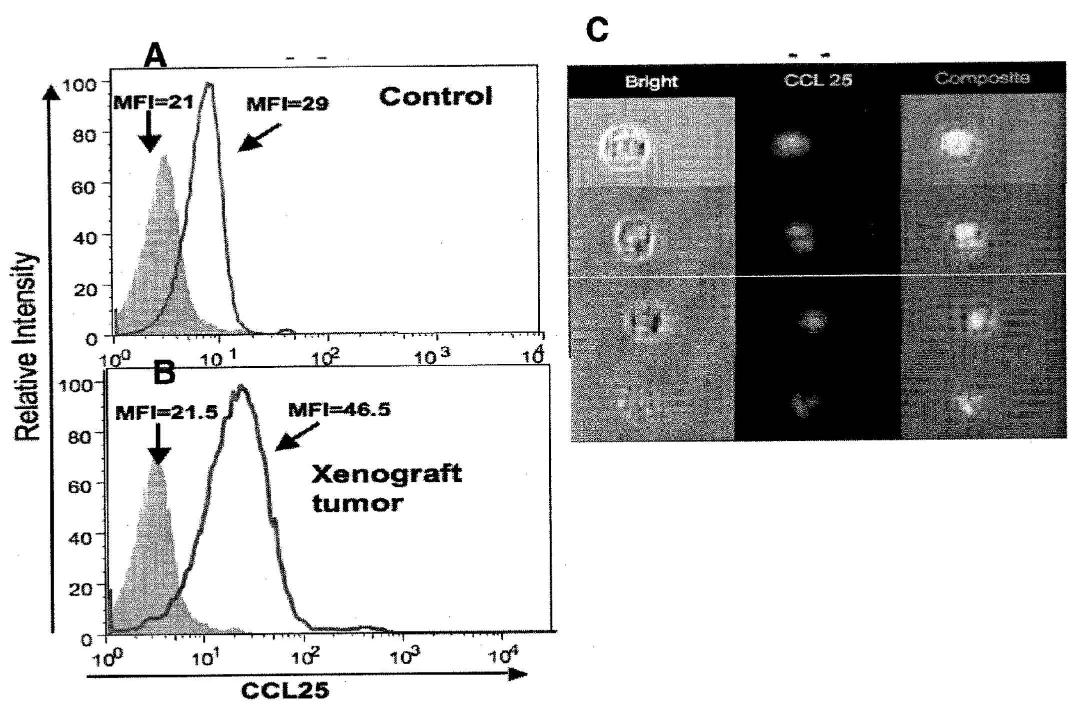
FIGS. 19A-C show CCL25 expression by mouse bone marrow cells.

FIGS. 19A-C shows CCL25 expression by mouse bone marrow cells. Bone marrow cells from non-tumor bearing (A) and tumor-bearing (B) mice were aspirated and stained with FITC-conjugated anti-CCL25 antibody. Positively stained cells (C) were quantified by Amnis ImageStream. Image-based analysis was performed using IDEAS-software and indicated a 1.6 fold increase in CCL25 expression by bone marrow cells after prostate tumor challenge.

Figure 20:
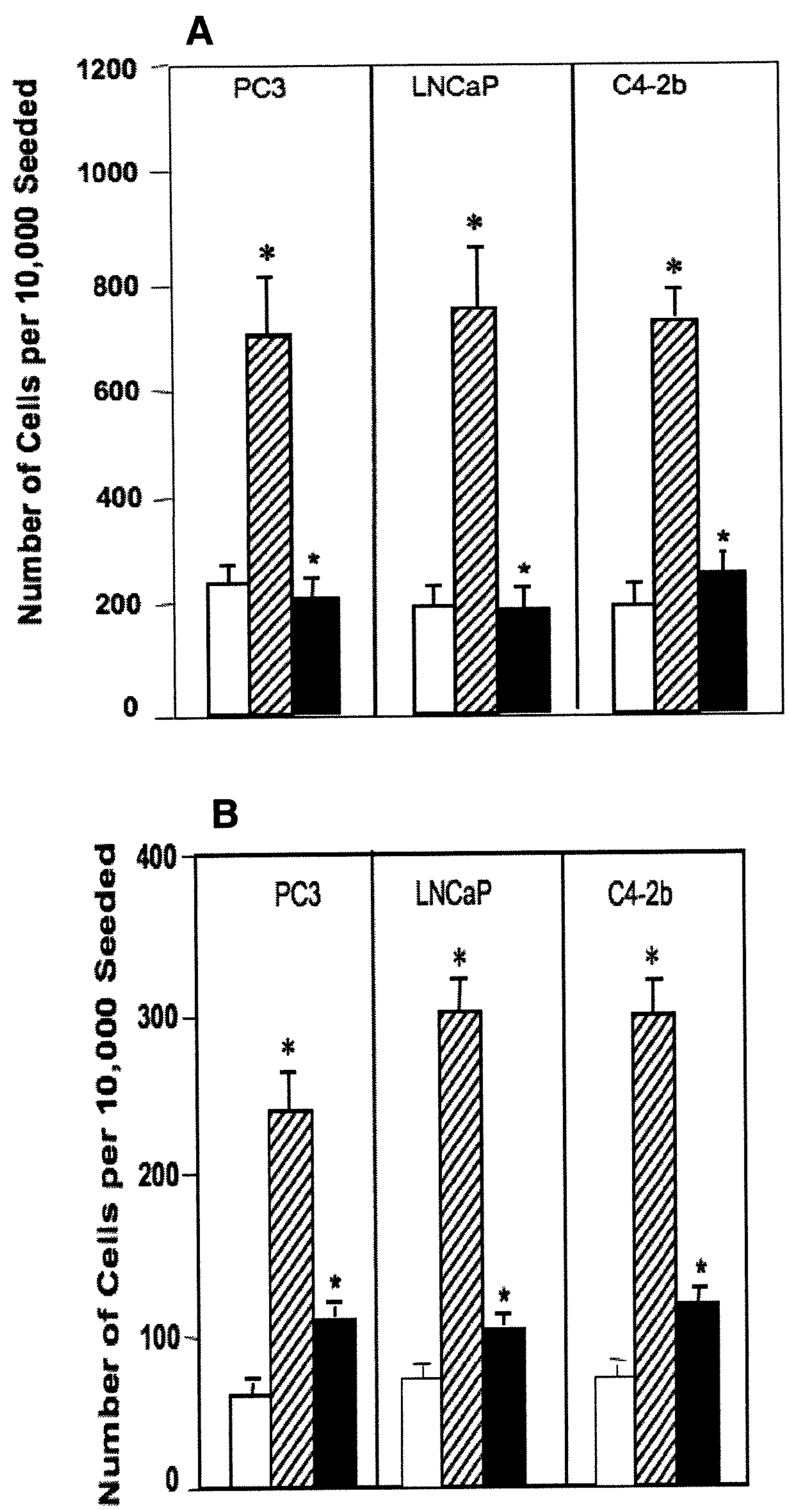
FIGS. 20A-B show CCR9-mediated prostate cancer cell migration and invasion.

FIGS. 20A-B show CCR9-mediated prostate cancer cell migration (A) and invasion (B). LNCaP, PC3, and C4-2b cells were tested for their ability to migrate to no additions (open bar), 100 ng/mL of CCL25 (hashed bar), or 100 ng/mL of CCL25+1 μg/mL anti-CCL25 antibody (solid bar). The number of cells (±SEM) that migrated and invaded in response to CCL25 from the initial 104 cells used to seed the migration and invasion chamber, show migration was CCL25 dependent and inhibited by anti-CCL25 antibody blockade. Asterisks indicate significant differences (p<0.01) between no additions and CCL25-treated cells.]

Figure 21:
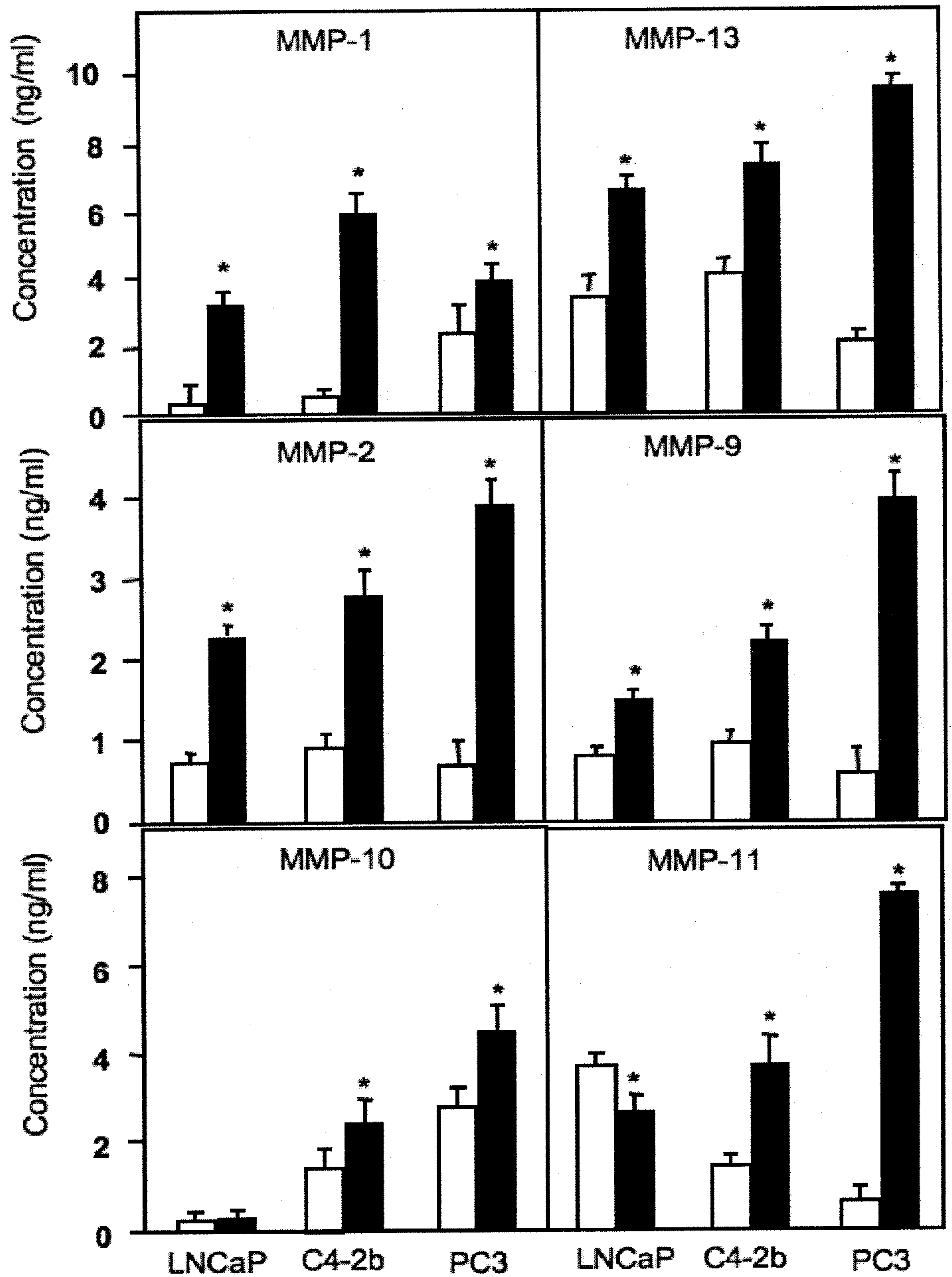
FIG. 21 shows CCL25-induced active MMP expression by prostate cancer cell lines.
Figure 22:
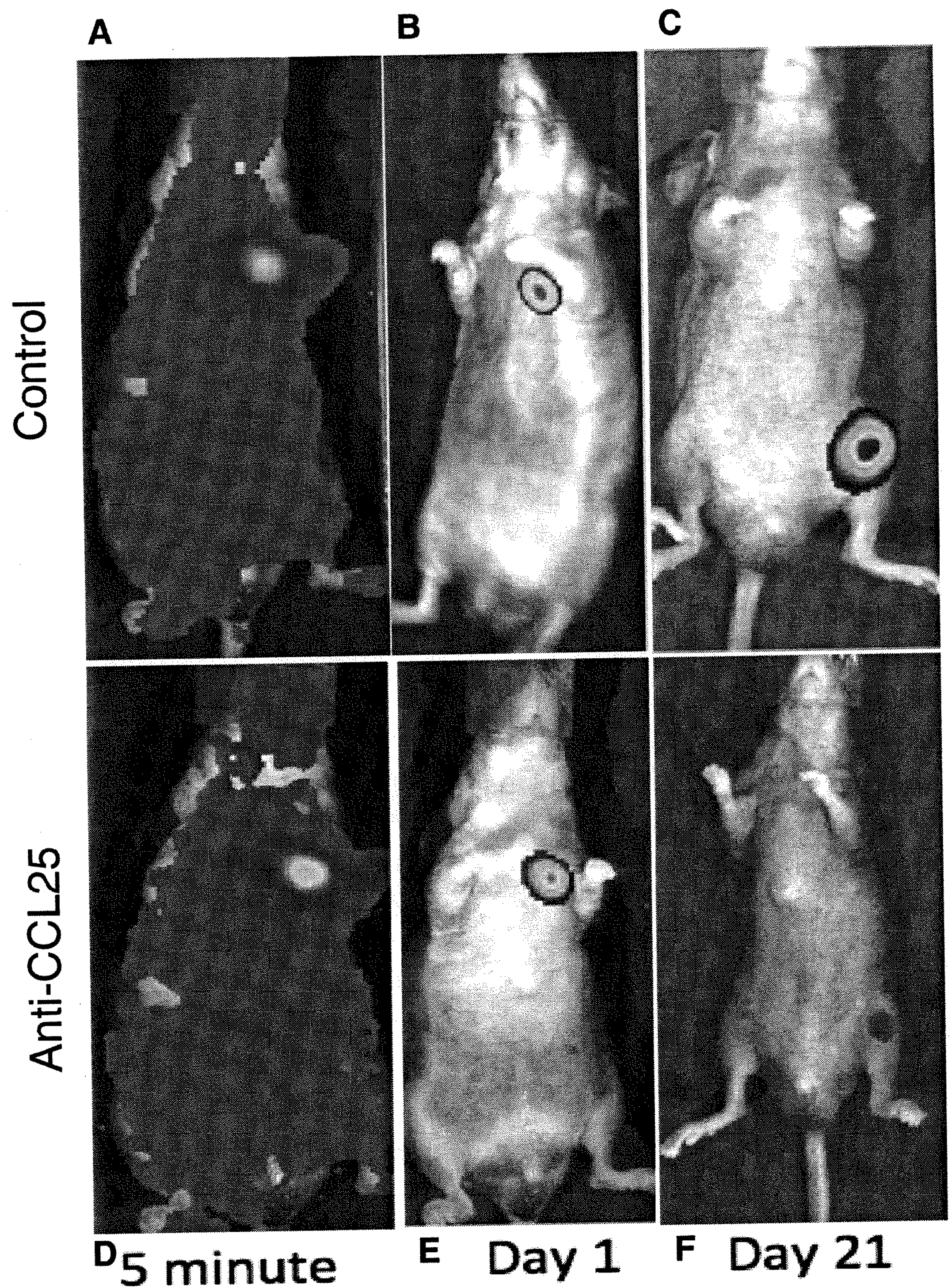
FIGS. 22A-F show inhibition of bone metastasis of PC3 prostate cancer cell line by CCR9 knockdown.

FIG. 21 shows CCL25-induced active matrix metalloproteinase (MMP) expression by LNCaP, PC3, and C4-2b prostate cancer cell lines. Cells were cultured for 24 hours without (open boxes) or with 100 ng/mL CCL25 (solid boxes). MMP-1, MMP-2, MMP-13, MMP-9, MMP-10, and MMP-11 protein levels, in cultured supernatants, were determined by MMP activity assays. Asterisks show a significant (P<0.05) increase or decrease in MMP secretion by a CCL25-treated cell line compared with the untreated cell line.

FIGS. 22A-F show inhibition of bone metastasis of PC3 prostate cancer cell line by CCR9 knockdown. Mice were challenged with a luciferase- and doxycyclene-inducible CCR9-specific shRNA-expressing PC3 cell line (A, D). Mice were challenged with this cell line by intracardiac injection. Subsequently, mice received no additions or doxycycline (0.2 mg/mL) in drinking for 21 days. Metastasis and tumor growth was monitored every week by Caliper Xenogen 100 in vivo imaging system. There were no changes 24 hours post challenge (B, E), but three weeks after challenge significantly less CCR9 knockdown PC3 (F) cells grew as bone metastases than compared to CCR9-positive PC3 cells (C).

Figure 23:
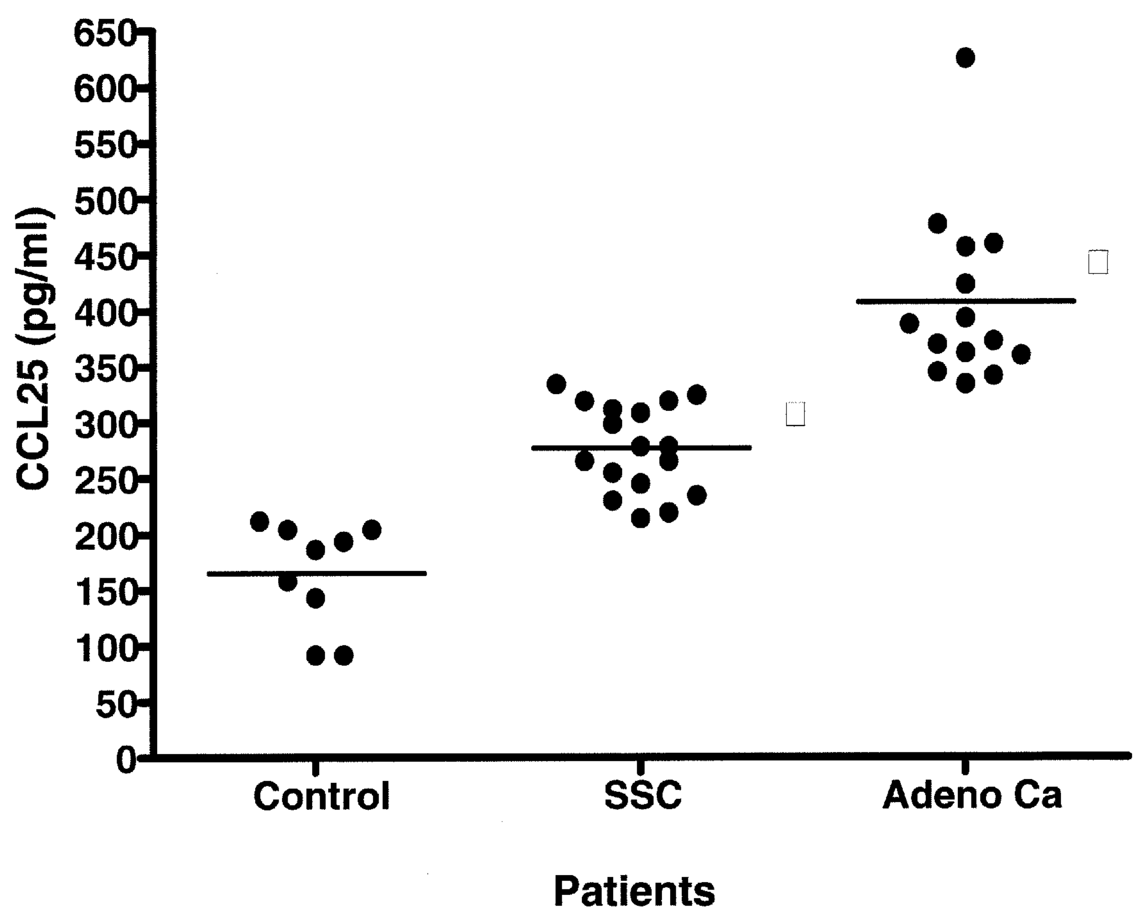
FIG. 23 shows serum CCL25 levels in lung cancer patients.
Figure 24:
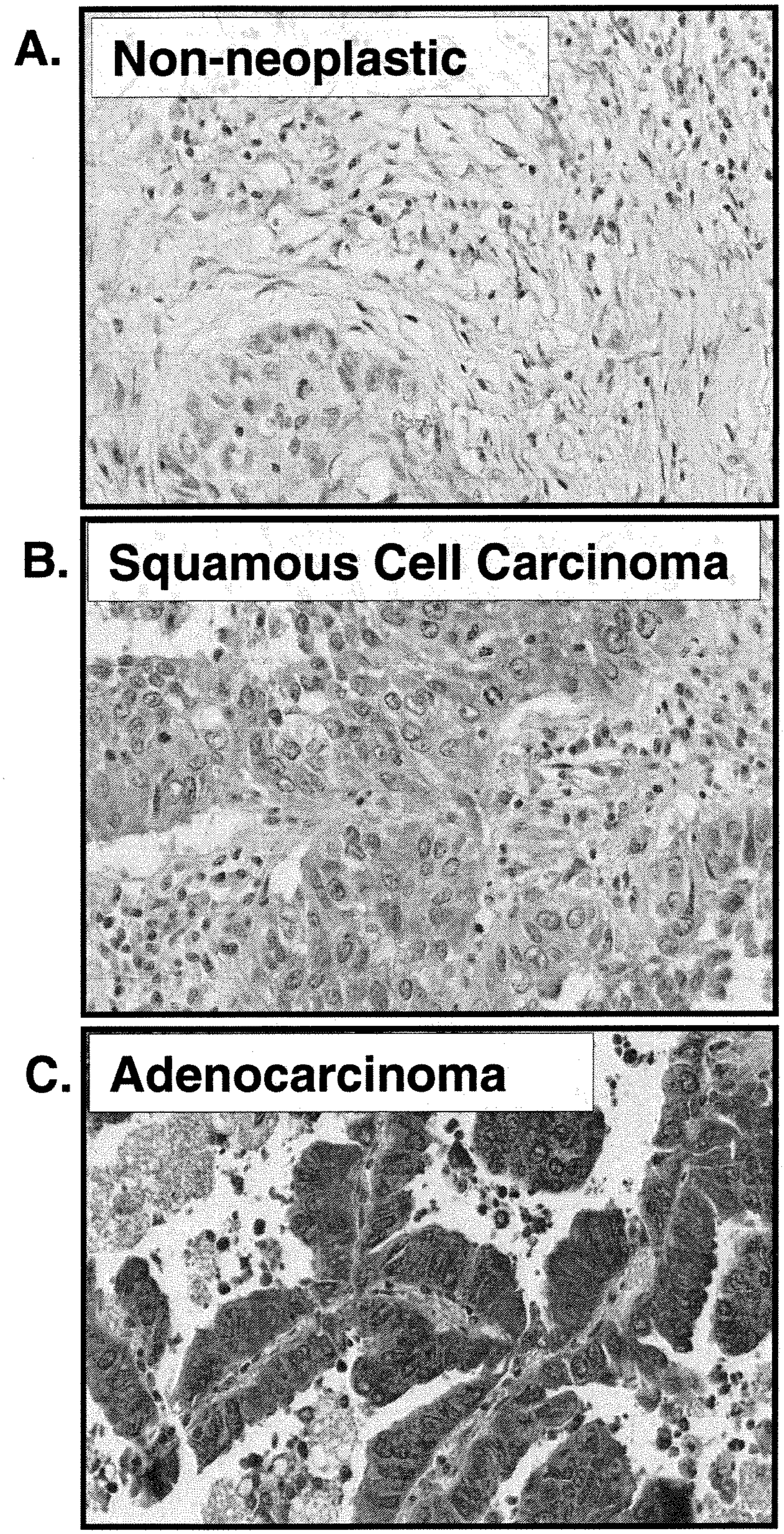
FIGS. 24A-C show CCR9 expression by non-neoplastic lung and lung cancer tissues.
Figure 25:
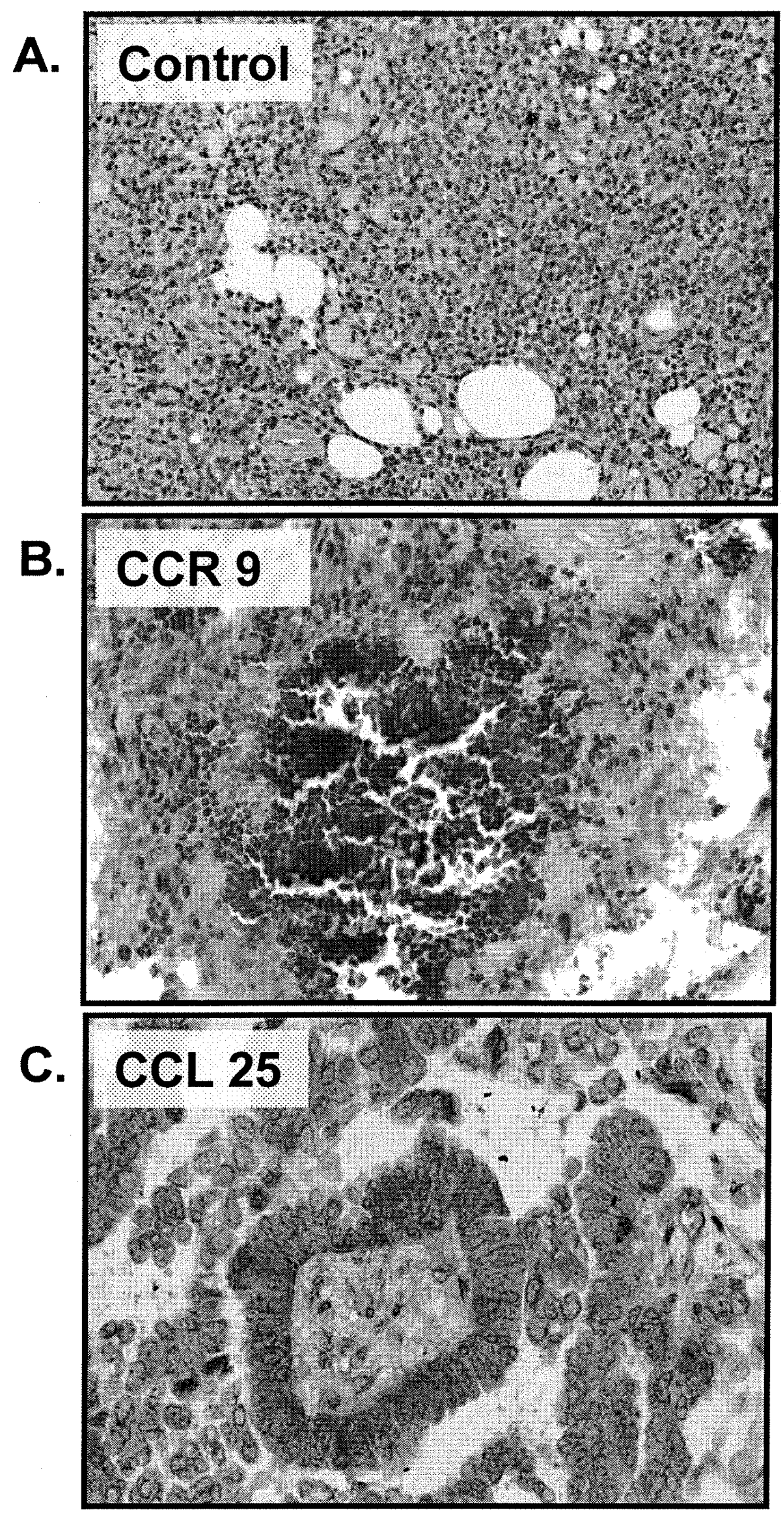
FIGS. 25A-C show CCR9-CCL25 expression by colon cancer tissues.

FIG. 23 shows serum CCL25 levels in lung cancer patients. CCL25 ELISAs were performed to quantify CCL25 levels in serum from patients diagnosed with adenocarcinoma (Adeno Ca; n=14), squamous cell carcinoma (SSC; n=17), and normal healthy donors (control; n=9). ELISAs were capable of detecting >5 pg/mL of CCL25. Solid circles indicate individual serum CCL25 levels and lines show median concentrations of each group. Asterisks indicate significant differences (p<0.01) between controls and groups with lung cancer.

FIGS. 24A-D show CCR9 expression by non-neoplastic lung and lung cancer tissues. Lung tissues from non-neoplastic (n=8)(A), adenocarcinoma (n=54)(B), and squamous cell carcinoma (n=24)(C) were stained with isotype control or anti-CCR9 antibodies. Brown (DAB) color show CCR9 staining. Aperio ScanScope CS system with a 40× objective captured digital images of each slide.

FIGS. 25A-D show CCR9-CCL25 expression by colon cancer tissues. Colon tissues from non-neoplastic (n=8) and adenocarcinoma (n=16) were stained with isotype control (A), anti-CCR9 (B) or anti-CCL25 (C) antibodies. Brown (DAB) stain indicates CCR9 positivity and magenta stain show CCL25 positivity. Aperio ScanScope CS system with a 40× objective captured digital images.

EXAMPLE 2

Detecting Chemokine Expression Levels with Real Time-PCR Analysis

Primer Design

Messenger RNA sequences for CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR1, CXCR2, CXCR3, CXCR4, CXCR5, CXCR5a, CXCR5b, CXCR6, CXCR7, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL24, CCL25, CCL25-1, CCL25-2, CCL27, CCL28, CCR1, CCR2, CCR3, CCR4, CCR5, CCR6, CCR7, CCR8, CCR9, CCR10, CCR11, XCL1, XCL2, XCR1, CX3CR1, or CX3CL1 were obtained from the NIH-NCBI gene bank database. Primers were designed using the BeaconJ 2.0 computer program. Thermodynamic analysis of the primers was conducted using computer programs: Primer PremierJ and MIT Primer 3. The resulting primer sets were compared against the entire human genome to confirm specificity.

Real Time PCR Analysis

Cancer cell lines (ATCC, Rockville, Md.) were cultured in RMPI-1640 containing 10% fetal calf serum supplemented with non-essential amino acids, L-glutamate, and sodium pyruvate (complete media). Primary tumor and normal-paired matched tissues were obtained from clinical isolates (Clinomics Biosciences, Frederick, Md. and UAB Tissue Procurement, Birmingham, Ala.). Messenger RNA (mRNA) was isolated from 106 cells using TriReagent (Molecular Research Center, Cincinnati, Ohio) according to manufacturer's protocols. Potential genomic DNA contamination was removed from these samples by treatment with 10 U/Fl of RNase free DNase (Invitrogen, San Diego, Calif.) for 15 minutes at 37° C. RNA was then precipitated and resuspended in RNA Secure (Ambion, Austin, Tex.). The cDNA was generated by reverse transcribing approximately 2 μg of total RNA using Taqman7 reverse transcription reagents (Applied Biosystems, Foster City, Calif.) according to manufacturer's protocols. Subsequently, cDNAs were amplified with specific human cDNA primers, to CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR1, CXCR2, CXCR3, CXCR4, CXCR5, CXCR5a, CXCR5b, CXCR6, CXCR7, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL24, CCL25, CCL25-1, CCL25-2, CCL27, CCL28, CCR1, CCR2, CCR3, CCR4, CCR5, CCR6, CCR7, CCR8, CCR9, CCR10, CCR11, XCL1, XCL2, XCR1, CX3CR1 or CX3CL1, using SYBR7 Green PCR master mix reagents (Applied Biosystems) according to manufacturer's protocol. The level of copies of mRNA of these targets were evaluated by real-time PCR analysis using the BioRad Icycler and software (Hercules, Calif.).

The RT-PCR products obtained using CXCL1-, CXCL2-, CXCL3-, CXCL4-, CXCL5-, CXCL6-, CXCL7-, CXCL8-, CXCL9-, CXCL10-, CXCL11-, CXCL12-, CXCL13-, CXCL14-, CXCL15-, CXCL16-, CXCR1-, CXCR2-, CXCR3-, CXCR4-, CXCR5-, CXCR5a-, CXCR5b-, CXCR6-, CXCR7-, CCL1-, CCL2-, CCL3-, CCL4-, CCL5-, CCL6-, CCL7-, CCL8-, CCL9-, CCL10-, CCL11-, CCL12-, CCL13-, CCL14-, CCL15-, CCL16-, CCL17-, CCL18-, CCL19-, CCL20-, CCL21-, CCL22-, CCL24-, CCL25-, CCL25-1-, CCL25-2-, CCL27-, CCL28-, CCR1-, CCR2-, CCR3-, CCR4-, CCR5-, CCR6-, CCR7-, CCR8-, CCR9-, CCR10-, CCR11-, XCL1-, XCL2-, XCR1-, CX3CR1-, or CX3CL1-specific primer sets did not cross react with other gene targets due to exclusion of primers that annealed to host sequences (NIH-NCBI Genebank). The primers produced different size amplicon products relative the polymorphisms that resulted in CXCR5a versus CXCR5b and CCL25, CCL25-1, versus CCL25-2. To this end, RT-PCR analysis of adenoma, carcinoma, leukemia, lymphoma, melanoma, and/or myeloma cell lines and tumor tissue revealed that chemokines and chemokine receptors were differentially expressed by cancer cells.

EXAMPLE 3

Anti-chemokine and Anti-chemokine Receptor Antibodies Inhibit Tumor Cell Growth in vitro and in vivo Anti-Sera Preparation 15 amino acid peptides from CXCR1, CXCR2, CXCL1, CXCL2, CXCL3, CXCL5, CXCL6, CXCL7, CXCL8, CXCL12, CXCR5a, CXCR5b, CXCL13, CXCR6, CXCL16, CCL16, CCL25, CCL25-1, CCL25-2, CCR9, CX3CR1, and CX3CL1 (SEQ ID NOS:1-21) were synthesized (Sigma Genosys, The Woodlands, Tex.) and conjugated to hen egg lysozyme (Pierce, Rockford, Ill.) to generate the antigen for subsequent immunizations for anti-sera preparation or monoclonal antibody generation. The endotoxin levels of chemokine peptide conjugates were quantified by the chromogenic Limulus amebocyte lysate assay (Cape Cod, Inc., Falmouth, Miss.) and shown to be <5 EU/mg. 100 μg of the antigen was used as the immunogen together with complete Freund's adjuvant Ribi Adjuvant system (RAS) for the first immunization in a final volume of 1.0 ml. This mixture was administered in 100 ml aliquots on two sites of the back of the rabbit subcutaneously and 400 ml intramuscularly in each hind leg muscle. Three to four weeks later, rabbits received 100 μg of the antigen in addition to incomplete Freund's adjuvant for 3 subsequent immunizations. Anti-sera were collected when anti-CXCR1, -CXCR2, -CXCL1, -CXCL2, -CXCL3, -CXCL5, -CXCL6-CXCL7, -CXCL8, -CXCL12, -CXCR5a, -CXCR5b, -CXCL13, -CXCR6, -CXCL16, -CCL16, -CCL25, -CCL25-1, -CCL25-2, -CCR9, -CX3CR1, and -CX3CL1 antibody titers reached 1:1,000,000. Subsequently, normal or anti-sera were heat-inactivated and diluted 1:50 in PBS.

Monoclonal Antibody Preparation 15 amino acid peptides from CXCR1, CXCR2, CXCL1, CXCL2, CXCL3, CXCL5, CXCL6, CXCL7, CXCL8, CXCL12, CXCR5a, CXCR5b, CXCL13, CXCR6, CXCL16, CCL16, CCL25, CCL25-1, CCL25-2, CCR9, CX3CR1, and CX3CL1 were synthesized (Sigma Genosys) and conjugated to hen egg lysozyme (Pierce) to generate the "antigen" for subsequent immunizations for anti-sera preparation or monoclonal antibody generation. The endotoxin levels of chemokine peptide conjugates were quantified by the chromogenic Limulus amebocyte lysate assay (Cape Cod, Inc., Falmouth, Miss.) and shown to be <5 EU/mg. 100 μg of the antigen was used as the immunogen together with complete Freund's adjuvant Ribi Adjuvant system (RAS) for the first immunization in a final volume of 200 μl. This mixture was subcutaneously administered in 100 μl aliquots at two sites of the back of a rat, mouse, or immunoglobulin-humanized mouse. Two weeks later, animals received 100 μg of the antigen in addition to incomplete Freund's adjuvant for 3 subsequent immunizations. Serum were collected and when anti-CXCR1, -CXCR2, -CXCL1, -CXCL2, -CXCL3, -CXCL5, -CXCL6-CXCL7, -CXCL8, -CXCL12, -CXCR5a, -CXCR5b, -CXCL13, -CXCR6, -CXCL16, -CCL16, -CCL25, -CCL25-1, -CCL25-2, -CCR9, -CX3CR1, or -CX3CL1 antibody titers reached 1:2,000,000, hosts were sacrificed and splenocytes were isolated for hybridoma generation. Briefly, B cells from the spleen or lymph nodes of immunized hosts were fused with immortal myeloma cell lines (e.g., YB2/0). Hybridomas were next isolated after selective culturing conditions (i.e., HAT-supplemented media) and limiting dilution methods of hybridoma cloning. Cells that produce antibodies with the desired specificity were selected using ELISA. Hybridomas from normal rats or mice were humanized with molecular biological techniques in common use. After cloning a high affinity and prolific hybridoma, antibodies were isolated from ascites or culture supernatants and adjusted to a titer of 1:2,000,000 and diluted 1:50 in PBS.

Anti-sera or Monoclonal Antibody Treatment

Immunodeficient nude NIH-III mice (8 to 12 weeks old, Charles River Laboratory, Wilmington, Mass.), which lack T, B, and NK cells, received $1\times10^6$ cancer cells, subcutaneously, for the establishment of a tumor. The established solid tumor was then removed from the host for immediate implantation or stored in liquid nitrogen for later implantation. Freshly isolated or liquid nitrogen frozen tumor tissue (1 g) were surgically implanted in the intestinal adipose tissue for the generation of tumor. Once the xenografted tumor growth reached 5 mm in size, the NIH-III mice received 200 μl intraperitoneal injections of either anti-sera or monoclonal antibodies every three days and the tumor was monitored for progression or regression of growth.

Data Analysis

SigmaStat 2000 (Chicago, Ill.) software was used to analyze and confine the statistical significance of data. The data were subsequently analyzed by the Student's t-test, using a two-factor, unpaired test. In this analysis, treated samples were compared to untreated controls. The significance level was set at $p<0.05$.

In vitro Growth Studies

The adenoma, carcinoma, leukemia, lymphoma, melanoma, and/or myeloma cell lines were grown in complete media in the presence or absence of antibodies specific for CXCR1, CXCR2, CXCL1, CXCL2, CXCL3, CXCL5, CXCL6 CXCL7, CXCL8, CXCR4, CXCL12, CXCR5a, CXCR5b, CXCL13, CXCR6, CXCL16, CCL16, CCR9, CCL25, CCL25-1, CCL25-2, CX3CR1, or CX3CL1. The growth of cancer cell lines expressing CXCR1 and/or CXCR2 were inhibited by antibodies to CXCR1, CXCR2, CXCL1, CXCL2, CXCL3, CXCL5, CXCL6, CXCL7, or CXCL8. Similarly, the growth of cancer cell lines expressing CXCR4 were inhibited by antibodies to CXCR4 or CXCL12. The growth of cancer cell lines expressing CXCR5a or CXCR5a were inhibited by antibodies to CXCR5a, CXCR5b, or CXCL13. The proliferation of cancer cell lines expressing CXCR6 were inhibited by antibodies to CXCR6 or CXCL16. The growth of cancer cell lines expressing CCR9 were inhibited by antibodies to CCR9, CCL25, CCL25-1, or CCL25-2. The propagation of cancer cell lines expressing CX3CR1 were inhibited by antibodies to CX3CR1 or CXC3L1. Of interest, antibodies against the soluble ligands, CXCL1, CXCL2, CXCL3, CXCL5, CXCL6, CXCL7, CXCL8, CXCL12, CXCL13, CXCL16, CCL16, CCL25, CCL25-1, CCL25-2, or CX3CL1, were more effective at growth inhibition that those directed against the membrane receptors.

In vitro Angiogenesis Studies

Microvascular endothelial cells (Cell Systems, Kirkland, Wash.) were grown according to supplier's protocols and allowed to form microvascular venules in an in vitro assay for angiogenesis (BD-Biocoat, Hercules, Calif.), in the presence or absence of antibodies specific for CXCR1, CXCR2, CXCL1, CXCL2, CXCL3, CXCL5, CXCL6, CXCL7, CXCL8, CXCR4, CXCL12, CXCR5a, CXCR5b, CXCL13, CXCR6, CXCL16, CCL16, CCR9, CCL25, CCL25-1, CCL25-2, CX3CR1, or CX3CL1. The angiogenesis was inhibited by antibodies against CXCR1, CXCR2, CXCL1, CXCL2, CXCL3, CXCL5, CXCL6, CXCL7, CXCL8, CXCR4, CXCL12, CXCR6 or CXCL16.

In vivo Growth Studies

Cancer cell lines or primary tumor tissue were adoptively transferred into NIH-III mice and allowed to form the xenograft tumor of interest. Antibodies directed against CXCR1, CXCR2, CXCL1, CXCL2, CXCL3, CXCL5, CXCL6, CXCL7, CXCL8, CXCR4, CXCL12, CXCR5a, CXCR5b, CXCL13, CXCR6, CXCL16, CCL16, CCR9, CCL25, CCL25-1, CCL25-2; CX3CR1, or CX3CL1 differentially affected the progression and regression of tumor size. In certain cases, antibodies directed towards CXCR1, CXCR2, CXCL1, CXCL2, CXCL3, CXCL5, CXCL6, CXCL7, CXCL8, CXCR4, CXCL12, CXCR6 or CXCL16 effectively lead to both regression and impeding progression of tumor growth. Antibodies directed against CXCR4, CXCL12, CXCR5a, CXCR5b, CXCL13, CCL16, CCR9, CCL25, CCL25-1, CCL25-2, CX3CR1, or CX3CL1 were effective at inhibiting the progression of tumor size.

The protein sequences of the chemokines used herein are recorded in NIH-NCBI GenBank as: (1) CXCR1 (ACCESSION# NP 000625), SEQ ID NO:1, (2) CXCR2(ACCESSION# NP 001548), SEQ ID NO:2, (3) CXCL1 (ACCESSION# NP 001502), SEQ ID NO:3, (4) CXCL2 (ACCESSION# NP 002080), SEQ ID NO:4, (5) CXCL3 (ACCESSION# NP 002081), SEQ ID NO:5, (6) CXCL5 (ACCESSION# NP 002985), SEQ ID NO:6, (7) CXCL6 (ACCESSION# NP 002984), SEQ ID NO:7, (8) CXCL7 (ACCESSION# NP 002695), SEQ ID NO:8, (9) CXCL8 (IL-8, ACCESSION# NP 000575), SEQ ID NO:9, (10) CXCR4 (ACCESSION# NP 003458), SEQ ID NO:10, (11) CXCL12 (ACCESSION# NP 000600), SEQ ID NO:11, (12) CXCR5A (ACCESSION# NP 116743), SEQ ID NO:12, (13) CXCR5B (ACCESSION# NP 001707), SEQ ID NO:13, (14) CXCL13 (ACCESSION# NP 006410), SEQ ID NO:14, (15) CXCR6 (ACCESSION# NP 006555), SEQ ID NO:15, (16) CXCL16 (ACCESSION# NP 071342), SEQ ID NO:16, (17) CCL16 (ACCESSION# NP 004581), SEQ ID NO:17, (18) CCL25 (ACCESSION# NP-005615.2), SEQ ID NO:18, (19) CCL25-1 (ACCESSION# NP 005615), SEQ ID NO:19, (20) CCL25-2 (ACCESSION# NP 683686), SEQ ID NO:20, (21) CX3CR1 (ACCESSION# NP 001328), SEQ ID NO:21, and (22) CX3CL1 (ACCESSION# NP 002987), SEQ ID NO:22.

The cDNA sequences are known and are available in NIH-NCBI GenBank under the following accession numbers: (23) CXCR1 (ACCESSION# NM 000634), SEQ ID NO:23, (24) CXCR2(ACCESSION# NM 001557), SEQ ID NO:24, (25) CXCL1 (ACCESSION# NM 001511), SEQ ID NO:25, (26) CXCL2 (ACCESSION# NM 002089), SEQ ID NO:26, (27) CXCL3 (ACCESSION# NM 002090), SEQ ID NO:27, (28) CXCL5 (ACCESSION# NM 002994), SEQ ID NO:28, (29) CXCL6 (ACCESSION# NM 002993), SEQ ID NO:29, (30) CXCL7 (ACCESSION# NM 002704), SEQ ID NO:30, (31) CXCL8 (IL-8, ACCESSION# NM 000584), SEQ ID NO:31, (32) CXCR4 (ACCESSION# NM 003467), SEQ ID NO:32, (33) CXCL12 (ACCESSION# NM 000609), SEQ ID NO:33, (34) CXCR5A (ACCESSION# NM 032966), SEQ ID NO:34, (35) CXCR5B (ACCESSION# NM 001716), SEQ ID NO:35, (36) CXCL13 (ACCESSION# NM 006419), SEQ ID NO:36, (37) CXCR6 (ACCESSION# NM 006564), SEQ ID NO:37, (38) CXCL16 (ACCESSION# NM 022059), SEQ ID NO:38, (39) CCL16 (ACCESSION# NM 004590), SEQ ID NO:39, (40) CCL25 (ACCESSION# NM 005624.3), SEQ ID NO:40, (41) CCL25-1 (ACCESSION# NM 005624), SEQ ID NO:41, (42) CCL25-2 (ACCESSION# NM 148888), SEQ ID NO:42, (43) CX3CR1 (ACCESSION# NM 001337), SEQ ID NO:43, and (44) CX3CL1 (ACCESSION# NM 002996), SEQ ID NO:44.

As shown in the table below, the particular chemokines which are most which any tumor expresses may vary. The methods of the present application may be customized for a particular patient, depending on the chemokines over-expressed by the patient's own tumor. It is possible to identify the particular chemokines which are over-expressed in the tumor using methods of the application and administer antibodies against that over-expressed chemokine. The tailoring of treatment for the cancer patient is novel, and is a particularly valuable aspect of the application.

TABLE 1 indicates the differing amounts of particular chemokines over-expressed in particular tumors that were studied.

TABLE 1

Chemokine, Chemokine Receptor and Cancer Association (dependent on stage of disease).

| Cancer | Chemokine | Chemokine Receptor |
|---|---|---|
| Carcinoma | CCL1, CCL2, CCL4, CCL17, CCL19, CCL21, CCL22, CCL25 | CCR2, CCR7, CCR8, CCR9 |
| | CXCL12, CXCL13, CXCL16 | CXCR4, CXCR5, CXCR6 |
| | CX3CL1 | CX3CR1 |
| Leukemia | CCL1, CCL4, CCL17, CCL19, CCL21, CCL22, CCL25 | CCR7, CCR8, CCR9 |
| | CXCL12 | CXCR4, CXCR7 |
| Lymphoma | CXCL12, CXCL13 | CXCR4, CXCR5 |
| Melanoma | CCL25, CCL27 | CCR9, CCR10 |
| | CXCL1, CXCL2, CXCL3, CXCL5, CXCL6, CXCL7, CXCL8, CXCL12, CXCL13, CXCL16 | CXCR1, CXCR2, CXCR4, CXCR5, CXCR6, CXCR7 |
| | CX3CL1 | CX3CR1 |
| Sarcoma | CCL1, CCL3, CCL4, CCL5, CCL7, CCL8, CCL11, CCL13, CCL17, CCL22, CCL24 | CCR3, CCR5, CCR8 |
| | CXCL12 | CXCR4, CXCR7 |
| | CX3CL1 | CX3CR1 |

EXAMPLE 4

CCR9-CCL25 Induced Anti-Apoptotic and/or Survival Signal Involved in PCa Chemo Resistance LNCaP (hormone responsive, wild type p53 expression), PC3 (hormone refractory, p53 null), and DU145 (hormone refractory, p53 mutated) cell lines are grown with or without CCL25 and with or without doxorubicin (1 μM/2 μM/4 μM), etoposide (20 μM/40 μM), estramustine (4 μM/10 μM), or docetaxel (10 nM/20 nM/40 nM) for 4, 8, 12, and 24 hours. Expression and activation of cell survival, pro- and anti-apoptotic signals (Akt, Src, CamKII, FAK, FKHR, FOXO, CREB, NF-κB, Myc, Fos, Jun Apaf1, Bax, Bcl2, BclX$_L$, BaK, Bad, Bik, Bim, TP53, Caspase-3, -6, -8, -9, survivin, vitronectin, β-Catenin) and molecules responsible for drug resistance or metabolism (Twist-1, Snail-1, Glutathione-S-transferase-π (GST-π), p53, topoisomerase I, IIα, IIβ, and ABC drug transporters) are accessed by real-time PCR and Western blot. Briefly, after treatment of cells, changes in the gene expression is tested using real-time PCR. Activation of signaling molecules is also be tested by phosphorylation specific antibody (i.e., Western blot analysis). To further confirm the role of the activated signaling molecules, following CCL25 treatment, expression or activity of the candidate molecules is inhibited using chemical inhibitors or siRNAs and target genes are analyzed by real-time PCR and Western blot analysis. Subsequently, the response of treated cells to chemotherapeutic drugs is evaluated by Vybrant apoptosis assay (Molecular probes) kit.

RNA Isolation and Real-Time PCR

Total RNA is isolated by TRIZOL™ (Invitrogen) method and quantified by UV spectrophotometry. Quality of RNA is analyzed by electrophoresis. The cDNA synthesis is completed using the ISCRIPT™ cDNA synthesis kit (BioRad) as described by the manufacturer. Real-time PCR is performed using IQ™ SYBR green supermix (BioRad) as described by manufacturer and specific primers designed against FAK, FKHR, FOXO, Apaf1, Bax, Bcl2, $BclX_L$, BaK, Bad, Bid, XIAP, Bik, Bim, TP53, cytochrome C, Caspase-3, -6, -8, -9, survivin, lamin, CamKII, vitronectin, β-Catenin, cadherins, Twist-1, Snail-1, CREB, NF-κB, Myc, Fos, Jun, β-actin and GAPDH. The results are calculated by delta delta Ct to quantify fold changes in mRNAs compared to untreated groups.

Western Blotting

Cells are harvested and resuspended in lysis buffer to extract total protein. Lysis buffer contains 50 mM Tris-HCl, pH 7.4, 150 mM NaCl, 1% Triton X-100, 1% deoxycholate, 0.1% SDS, 5 mM EDTA supplemented with protease inhibitors, 1 mM phenylmethylsulphonylfluoride, 1 mM benzamidine, 10 μg/mL soybean trypsin inhibitor, 50 μg/mL leupeptin, 1 μg/mL pepstatin and 20 μg/mL aprotinin. Cell lysates are stored on ice for 30 min, centrifuged (14000×g) for 20 min at 4° C., and supernatant is used for Western blot analysis of genes demonstrating significant modulation in mRNA level. Similarly, phosphor-specific antibodies are used to test changes in the level of phophorylation of Akt1/2/3, mTOR, FAK, FKHR, FOXO, and GSK-3β. Moreover, activation of caspases and PARP, following cleavage are evaluated using specific antibodies. The results obtained after chemiluminescent detection of protein bands by ECL plus reagent (Pharmecia) on X-ray film is normalized to β-actin and/or GAPDH using Image J image analysis software (NIH).

Detection of Cytochrome C Release

Cells are collected and washed in PBS, and resuspended in extraction buffer containing 220 mM mannitol, 68 mM sucrose, 50 mM PIPES-KOH, pH 7.4, 50 mM KCl, 5 mM EGTA, 2 mM $MgCl_2$, 1 mM DTT, and protease inhibitors. After 30 min incubation on ice, cells are homogenized using Glass-Teflon homogenizer and homogenates will be spun at 14,000 g for 15 min. Cytosolic extracts are used for Western blot analysis using anti-cytochrome C monoclonal antibody (PharMingen).

siRNA Transfection, Chemical Inhibitor, and Apoptosis Detection

Prostate cancer cell lines are transfected with gene specific and nonspecific control siRNAs (Dharmacon) using LipofectAMINE 2000 (Invitrogen). Optimum gene knock-down time and siRNA concentration are confirmed by western blot analysis and further evaluated for cell survival following drug treatment with or without CXCL16, control antibody, and/or anti-CXCR6 antibody. The detection of changes in live, apoptotic, and necrotic cells is evaluated as follows: cell survival is tested by Vybrant apoptosis as described by the manufacturer (Molecular probe), using FACScan flow cytometer and CellQuest™ software (BD Pharmingen). Change in downstream gene expression after gene knockdown is tested using real-time PCR and Western blotting.

Cells treated with CCL25 show enhanced expression of cell survival and drug transporter proteins which show differences in their expression pattern in hormone responsive and non responsive cells. Anti-CCL25 Abs effectively reverse the effect of CCL25 in PCa cells. Doxorubicin, estramustine, etoposide and docetaxel induce apoptosis in PCa cells without CCL25 treatment (or CCR9 blockade).

EXAMPLE 5

CCR9-CCL25 Induced Changes in ABC Drug Transporters

LNCaP, PC3, and DU145 cells are grown with or without CCL25, anti-CCL25 antibody, control antibody, and/or anti-CCR9 antibodies along with or without doxorubicin, estramustine, etoposide or docetaxel for 4, 8, 12 or 16 hours as described earlier. After treatment, changes in the ABC transporter and Twist-1 mRNA expression are quantified by real-time PCR, as described above, using specific primers directed for ABC and Twist-1 cDNA. The genes demonstrating significant alterations in mRNA expression are further tested by Western blot analysis. Nuclear extracts from treated cells are evaluated by chromatin immuno-precipitation (ChIP) assay to determine whether the transcriptional factors induced by CXCL16 bind the promoter region of ABC transporters and Twist-1.

Chromatin Immuno-precipitation (ChIP)

The results from Example 4 provide information about the genes that are regulated as well as those that may modulate transcription factors activated by CCR9-CCL25 interaction. Based on these results, target transcription factors and genes are selected. Specific PCR primers are designed against the promoter region of these genes containing the binding sites of transcription factors. PCR primer are used to amplify the DNA being precipitated along with transcription factors. Cells are harvested by trypsinization in the presence of 20 mM butyrate. 50,000 cells are re-suspended in 500 μl PBS/butyrate. Proteins and DNA are cross-linked with 1% formaldehyde for 8 min at room temperature and cross-linking is stopped with 125 mM glycine for 5 min. Cells are centrifuged at 470 g in a swing-out rotor with soft deceleration settings for 10 min at 4° C. and washed twice in 0.5 ml ice-cold PBS/butyrate by vortexing followed by centrifugation. Cells are lysed by addition of lysis buffer (50 mM Tris-HCl, pH 8, 10 mM EDTA, 1% SDS, protease inhibitor cocktail (Sigma-Aldrich), 1 mM PMSF, 20 mM butyrate, vortexing and subsequent centrifugation. This procedure is known to produce chromatin fragments of 500 bp. The sonicated lysate is diluted 8-fold in RIPA buffer containing a protease inhibitor cocktail, 1 mM PMSF, and 20 mM butyrate (RIPA ChIP buffer). RIPA ChIP buffer (330 μl) is added to the pellet and mixed by vortexing. Immunoprecipitation and washes of the ChIP material is accomplished by the use of antibody-directed against specific transcription factors. Chromatin is aliquoted into tubes containing antibody-bead complexes. Input sample is placed in a tube for phenol-chloroform isoamyl alcohol isolation. The immunoprecipitated material is washed three times and transferred into a new tube while in TE. DNA elution in 1% SDS, cross-link reversal and proteinase K digestion is carried out in a single step for 2 hrs at 68° C. DNA is extracted with phenol-chloroform isoamylalcohol, and ethanol-precipitation in presence of acrylamide carrier (Sigma-Aldrich) and dissolved in TE. Immunoprecipitated DNA from 3-4 independent ChIPs is analyzed by real time PCR. Real-time PCR data is expressed as percent (±SD) precipitated (antibody-bound) DNA relative to input DNA, in three independent replicate ChIP assays.

Phosphorylation and activation of transcription factors such as CREB, Fos, Jun, and NFkB via CCR9-CCL25 signaling subsequently leads to increases in expression of ABC transporters and Twist-1. Decreases in gene expression are observed if negative regulatory elements are present in the same promoter. Since hormone-dependent and refractory PCa cells have differences in the expression of these intracellular signaling molecules, they show variations in genes to be modulated by hormone dependent and refractory conditions. The modulation in gene expression shows differences with drug treatment in presence of CCL25 and in absence of CCL25 treatment.

EXAMPLE 6

In vivo Evaluation of CCL25-directed Therapy

Male nude mice are subcutaneously challenged by luciferase expressing androgen responsive (LNCaP-Luc) and non-responsive (PC3-Luc) cells. Tumor development is measured non-invasively using in vivo imaging system. After establishment of a measurable tumor, mice are divided into treatment (A, B, C, D and E) and control groups (F, G, H, I, J and K). Group "A" receives CCL25 neutralizing antibodies (12.5 mg/kg/day) every alternate day and controls (group F) receive isotype control antibodies (12.5 mg/kg/day). Group "B," "C," "D" and "E" receive CCL25 neutralizing antibodies (12.5 mg/kg/day) with intraperitoneal injection of doxorubicin (5 mg/kg/day on days 1 to 3 followed by administration on days 15 to 17), intravenous injection of etoposide (10 mg/kg/day; on day 1, 5, 9, 14, 19 and 24), intravenous injection of estramustine (4 mg/kg/day on day 1-5 and day 26-31), or intraperitoneal injection of docetaxel (8 mg/kg/day twice a week for 4 weeks), respectively. Controls for these treatment groups ("G," "H," "I" and "J," respectively) receive theses drugs using similar concentration and injection protocol with isotype control antibodies (12.5 mg/kg/day). Group "K" receives PBS and serves as placebo. Tumor progression and regression in treatment and controls are evaluated by non-invasive in vivo imaging. The tumor from treated groups and untreated control groups is excised and evaluated for the changes in the cell survival and drug resistance proteins by immunohistochemistry. In the context used herein, the term "CCL25 neutralizing antibodies" means anti-CCL25 antibodies and/or anti-CCR9 antibodies.

Statistics (Significance) and Sample Size

Sample size (or power) calculations are relevant to the design of preliminary studies and determining the requirements for proposed experiments. To interpret our results, significance tests and statistical analysis are also critical. The traditional α-value, i.e., p=0.01, is used to evaluate the statistical significance of this study. The proposed experiment will require a minimum of 10 mice per group. The data is expressed as the mean±SEM and compared using a two-tailed paired (or unpaired) student's t-test for normally distributed samples or an unpaired Mann Whitney U test as a non-parametric test for samples not normally distributed. The results are analyzed using SYSTAT (Systat software Inc.) statistical program. Single-factor and two-factor variance ANOVA analyses are used to evaluate groups and subgroups, respectively. Hence, results are considered statistically significant if p values are <0.05.

Animals

Six to eight week old male nude mice are subcutaneously injected with PCa cells. Briefly, $5\times10^6$ Luciferase expressing PC3 cells are resuspended in 100 μl of sterile PBS and injected into the flanks of nude mice under isoflurane anesthesia. Luciferase expressing LNCaP cells ($5\times10^6$ cell) are mixed with 50% Matrigel (Becton Dickinson) and injected in the flanks of nude mice under isoflurane anesthesia.

Analysis of In Vivo Tumor Growth

Tumor bearing nude mice receive 150 mg/kg D-Luciferin (Xenogen) by intra-peritoneal injection Using 25×⅝" gauge needle 15 minutes before imaging. The mice are imaged using the IVIS100 in vivo imaging system and results expressed in photons/sec/cm$^2$/sr. Tumor volume is measured by use of calipers and calculated by the formula (Larger diameter)×(smaller diameter)$^2$×0.5.

Cell Survival, Apoptotic and Drug Resistant Gene Expression Analysis

Tumors from all groups are excised three days after completion of treatment protocols. Tumors are fixed in 4% PFA and embedded in paraffin. Paraffin sections (thickness 7 μm) are mounted on glass slides, deparaffinized and re-hydrated (Xylene for 5 min; absolute, 95% and 70% ethanol for 1 min each). The rehydrated sections are used for peroxidase based immunohistochemical staining for drug transporters, PI3K, Akt, FAK, FKHR, FOXO, Apaf1, Bax, Bcl2, $BclX_L$, BaK, Bad, Bid, XIAP, Bik, Bim, TP53, Cytochrome C, Caspase-3, -6, -8, -9, survivin, lamin, CamKII, vitronectin, β-Catenin, cadherins, Twist-1, CREB, NF-κB, Myc, Fos, Jun, CCR9 and CCL25. After staining, slides are scanned and analyzed by the Aperio scanscope (Aperio) system.

CCL25 neutralization leads to decreased cell survival in response to drugs, thus reduction of tumor volume. However, the response also varies among the tumors formed by hormone sensitive (LNCaP) and hormone refractory (PC3 cells). Further, chemotherapeutic drugs have lower efficacy in the tumors with a functional CCR9-CCL25 axis, which may enhance the expression of ABC proteins known to transport these drugs out of the cell.

The above description is for the purpose of teaching the person of ordinary skill in the art how to practice the present invention, and is not intended to detail all those obvious modifications and variations of it that will become apparent to the skilled worker upon reading the description. It is intended, however, that all such obvious modifications and variations be included within the scope of the present invention, which is defined by the following claims. The claims are intended to cover the components and steps in any sequence that is effective to meet the objectives there intended, unless the context specifically indicates the contrary. All the references cited in the specification are herein incorporated by reference in their entirely.

What is claimed is:

1. A method for diagnosing ovarian cancer in a subject, comprising:

contacting, an ovarian tissue sample obtained from said subject with one or more antibodies that bind specifically to CCL25 or CCR9 or both CCL25 and CCR9;

measuring the level(s) of expression of CCL25 and/or CCR9 based on their interactions with said one or more antibodies in said ovarian tissue sample; and comparing the level of expression of CCL25 and/or CCR9 in said ovarian tissue sample to a normal level of expression of said one or more cancer markers, wherein a higher than normal level of expression of CCL25 and/or CCR9 in said ovarian tissue sample is indicative of the presence of ovarian cancer in said subject, and wherein said normal level of expression of CCL25 and/or CCR9 is a predetermined value or is obtained from a control sample of known normal non-cancerous ovarian cells of the same origin or type as said ovarian tissue sample.

2. A method for assessing the prognosis of a subject with ovarian cancer, comprising:

contacting a biological sample obtained from said subject with one or more antibodies that bind specifically to CCL25 or CCR9 or both CCL25 and CCR9;

determining the expression level of CCL25 and/or CCR9 in said biological sample, and comparing the level of expression of CCL25 and/or CCR9 in said biological sample to a control level of expression of CCL25 and/or CCR9, wherein a higher level of expression of said one or more cancer markers in the biological sample relative to said control level indicates that the prognosis of said subject for surviving ovarian cancer is poor, wherein a lower or similar level of expression of said one or more cancer markers in said biological sample relative to said control level indicates that the prognosis of said subject for surviving ovarian cancer is good, wherein a poor prognosis indicates that said ovarian cancer is of an aggressive or invasive type, and wherein said one or more cancer markers comprise CCL25 or CCR9 or both CCL25 and CCR9.

3. The method of claim 2, wherein said biological sample is plasma, saliva or urine.

4. A method for monitoring the course of ovarian cancer treatment in a subject, comprising:

contacting one or more biological samples obtained from said subject, during or after said treatment, with one or more antibodies that bind specifically to CCL25 or CCR9 or both CCL25 and CCR9;

determining the expression level(s) of CCL25 and/or CCR9 in said one or more biological samples, and comparing the expression level(s) of CCL25 and/or CCR9 in said one or more biological samples to control expression level(s) of CCL25 and/or CCR9, wherein said control expression levels are pre-treatment levels of CCL25 and/or CCR9 in said subject or predetermined reference levels, and wherein said treatment is deemed efficacious for ovarian cancer treatment if said expression level(s) of CCL25 and/or CCR9 in said one or more biological samples is similar to or lower than said control expression level(s).

5. The method of claim 4, wherein said biological sample is plasma, saliva or urine.

* * * * *

SEQUENCE LISTING

```
<160> NUMBER OF SEQ ID NOS: 137

<210> SEQ ID NO 1
<211> LENGTH: 350
<212> TYPE: PRT
<213> ORGANISM: Homo sapiens

<400> SEQUENCE: 1

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
```

-continued

```
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350


<210> SEQ ID NO 2
<211> LENGTH: 360
<212> TYPE: PRT
<213> ORGANISM: Homo sapiens

<400> SEQUENCE: 2

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
```

```
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360


<210> SEQ ID NO 3
<211> LENGTH: 107
<212> TYPE: PRT
<213> ORGANISM: Homo sapiens

<400> SEQUENCE: 3

Met Ala Arg Ala Ala Leu Ser Ala Ala Pro Ser Asn Pro Arg Leu Leu
1               5                   10                  15

Arg Val Ala Leu Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
```

65 70 75 80

Gly Arg Lys Ala Cys Leu Asn Pro Ala Ser Pro Ile Val Lys Lys Ile
85 90 95

Ile Glu Lys Met Leu Asn Ser Asp Lys Ser Asn
100 105

<210> SEQ ID NO 4
<211> LENGTH: 107
<212> TYPE: PRT
<213> ORGANISM: Homo sapiens

<400> SEQUENCE: 4

Met Ala Arg Ala Thr Leu Ser Ala Ala Pro Ser Asn Pro Arg Leu Leu
1 5 10 15

Arg Val Ala Leu Leu Leu Leu Leu Leu Val Ala Ala Ser Arg Arg Ala
20 25 30

Ala Gly Ala Pro Leu Ala Thr Glu Leu Arg Cys Gln Cys Leu Gln Thr
35 40 45

Leu Gln Gly Ile His Leu Lys Asn Ile Gln Ser Val Lys Val Lys Ser
50 55 60

Pro Gly Pro His Cys Ala Gln Thr Glu Val Ile Ala Thr Leu Lys Asn
65 70 75 80

Gly Gln Lys Ala Cys Leu Asn Pro Ala Ser Pro Met Val Lys Lys Ile
85 90 95

Ile Glu Lys Met Leu Lys Asn Gly Lys Ser Asn
100 105

<210> SEQ ID NO 5
<211> LENGTH: 107
<212> TYPE: PRT
<213> ORGANISM: Homo sapiens

<400> SEQUENCE: 5

Met Ala His Ala Thr Leu Ser Ala Ala Pro Ser Asn Pro Arg Leu Leu
1 5 10 15

Arg Val Ala Leu Leu Leu Leu Leu Leu Val Ala Ala Ser Arg Arg Ala
20 25 30

Ala Gly Ala Ser Val Val Thr Glu Leu Arg Cys Gln Cys Leu Gln Thr
35 40 45

Leu Gln Gly Ile His Leu Lys Asn Ile Gln Ser Val Asn Val Arg Ser
50 55 60

Pro Gly Pro His Cys Ala Gln Thr Glu Val Ile Ala Thr Leu Lys Asn
65 70 75 80

Gly Lys Lys Ala Cys Leu Asn Pro Ala Ser Pro Met Val Gln Lys Ile
85 90 95

Ile Glu Lys Ile Leu Asn Lys Gly Ser Thr Asn
100 105

<210> SEQ ID NO 6
<211> LENGTH: 114
<212> TYPE: PRT
<213> ORGANISM: Homo sapiens

<400> SEQUENCE: 6

Met Ser Leu Leu Ser Ser Arg Ala Ala Arg Val Pro Gly Pro Ser Ser
1 5 10 15

Ser Leu Cys Ala Leu Leu Val Leu Leu Leu Leu Leu Thr Gln Pro Gly
20 25 30

```
Pro Ile Ala Ser Ala Gly Pro Ala Ala Ala Val Leu Arg Glu Leu Arg
        35                  40                  45

Cys Val Cys Leu Gln Thr Thr Gln Gly Val His Pro Lys Met Ile Ser
    50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn


<210> SEQ ID NO 7
<211> LENGTH: 114
<212> TYPE: PRT
<213> ORGANISM: Homo sapiens

<400> SEQUENCE: 7

Met Ser Leu Pro Ser Ser Arg Ala Ala Arg Val Pro Gly Pro Ser Gly
1               5                   10                  15

Ser Leu Cys Ala Leu Leu Ala Leu Leu Leu Leu Leu Thr Pro Pro Gly
            20                  25                  30

Pro Leu Ala Ser Ala Gly Pro Val Ser Ala Val Leu Thr Glu Leu Arg
        35                  40                  45

Cys Thr Cys Leu Arg Val Thr Leu Arg Val Asn Pro Lys Thr Ile Gly
    50                  55                  60

Lys Leu Gln Val Phe Pro Ala Gly Pro Gln Cys Ser Lys Val Glu Val
65                  70                  75                  80

Val Ala Ser Leu Lys Asn Gly Lys Gln Val Cys Leu Asp Pro Glu Ala
                85                  90                  95

Pro Phe Leu Lys Lys Val Ile Gln Lys Ile Leu Asp Ser Gly Asn Lys
            100                 105                 110

Lys Asn


<210> SEQ ID NO 8
<211> LENGTH: 128
<212> TYPE: PRT
<213> ORGANISM: Homo sapiens

<400> SEQUENCE: 8

Met Ser Leu Arg Leu Asp Thr Thr Pro Ser Cys Asn Ser Ala Arg Pro
1               5                   10                  15

Leu His Ala Leu Gln Val Leu Leu Leu Leu Ser Leu Leu Leu Thr Ala
            20                  25                  30

Leu Ala Ser Ser Thr Lys Gly Gln Thr Lys Arg Asn Leu Ala Lys Gly
        35                  40                  45

Lys Glu Glu Ser Leu Asp Ser Asp Leu Tyr Ala Glu Leu Arg Cys Met
    50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
            100                 105                 110

Ile Lys Lys Ile Val Gln Lys Lys Leu Ala Gly Asp Glu Ser Ala Asp
        115                 120                 125
```

<210> SEQ ID NO 9
<211> LENGTH: 99
<212> TYPE: PRT
<213> ORGANISM: Homo sapiens

<400> SEQUENCE: 9

```
Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 10
<211> LENGTH: 352
<212> TYPE: PRT
<213> ORGANISM: Homo sapiens

<400> SEQUENCE: 10

```
Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240
```

```
Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350


<210> SEQ ID NO 11
<211> LENGTH: 93
<212> TYPE: PRT
<213> ORGANISM: Homo sapiens

<400> SEQUENCE: 11

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90


<210> SEQ ID NO 12
<211> LENGTH: 327
<212> TYPE: PRT
<213> ORGANISM: Homo sapiens

<400> SEQUENCE: 12

Met Ala Ser Phe Lys Ala Val Phe Val Pro Val Ala Tyr Ser Leu Ile
1               5                   10                  15

Phe Leu Leu Gly Val Ile Gly Asn Val Leu Val Leu Val Ile Leu Glu
            20                  25                  30

Arg His Arg Gln Thr Arg Ser Ser Thr Glu Thr Phe Leu Phe His Leu
        35                  40                  45

Ala Val Ala Asp Leu Leu Leu Val Phe Ile Leu Pro Phe Ala Val Ala
    50                  55                  60

Glu Gly Ser Val Gly Trp Val Leu Gly Thr Phe Leu Cys Lys Thr Val
65                  70                  75                  80

Ile Ala Leu His Lys Val Asn Phe Tyr Cys Ser Ser Leu Leu Leu Ala
                85                  90                  95

Cys Ile Ala Val Asp Arg Tyr Leu Ala Ile Val His Ala Val His Ala
            100                 105                 110

Tyr Arg His Arg Arg Leu Leu Ser Ile His Ile Thr Cys Gly Thr Ile
        115                 120                 125
```

```
Trp Leu Val Gly Phe Leu Leu Ala Leu Pro Glu Ile Leu Phe Ala Lys
    130                 135                 140

Val Ser Gln Gly His His Asn Asn Ser Leu Pro Arg Cys Thr Phe Ser
145                 150                 155                 160

Gln Glu Asn Gln Ala Glu Thr His Ala Trp Phe Thr Ser Arg Phe Leu
                165                 170                 175

Tyr His Val Ala Gly Phe Leu Leu Pro Met Leu Val Met Gly Trp Cys
            180                 185                 190

Tyr Val Gly Val Val His Arg Leu Arg Gln Ala Gln Arg Arg Pro Gln
        195                 200                 205

Arg Gln Lys Ala Val Arg Val Ala Ile Leu Val Thr Ser Ile Phe Phe
    210                 215                 220

Leu Cys Trp Ser Pro Tyr His Ile Val Ile Phe Leu Asp Thr Leu Ala
225                 230                 235                 240

Arg Leu Lys Ala Val Asp Asn Thr Cys Lys Leu Asn Gly Ser Leu Pro
                245                 250                 255

Val Ala Ile Thr Met Cys Glu Phe Leu Gly Leu Ala His Cys Cys Leu
            260                 265                 270

Asn Pro Met Leu Tyr Thr Phe Ala Gly Val Lys Phe Arg Ser Asp Leu
        275                 280                 285

Ser Arg Leu Leu Thr Lys Leu Gly Cys Thr Gly Pro Ala Ser Leu Cys
    290                 295                 300

Gln Leu Phe Pro Ser Trp Arg Arg Ser Ser Leu Ser Glu Ser Glu Asn
305                 310                 315                 320

Ala Thr Ser Leu Thr Thr Phe
                325


<210> SEQ ID NO 13
<211> LENGTH: 372
<212> TYPE: PRT
<213> ORGANISM: Homo sapiens

<400> SEQUENCE: 13

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175
```

```
Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370


<210> SEQ ID NO 14
<211> LENGTH: 109
<212> TYPE: PRT
<213> ORGANISM: Homo sapiens

<400> SEQUENCE: 14

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
        35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105


<210> SEQ ID NO 15
<211> LENGTH: 342
<212> TYPE: PRT
<213> ORGANISM: Homo sapiens

<400> SEQUENCE: 15

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
```

```
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340


<210> SEQ ID NO 16
<211> LENGTH: 120
<212> TYPE: PRT
<213> ORGANISM: Homo sapiens

<400> SEQUENCE: 16

Met Lys Val Ser Glu Ala Ala Leu Ser Leu Leu Val Leu Ile Leu Ile
1               5                   10                  15

Ile Thr Ser Ala Ser Arg Ser Gln Pro Lys Val Pro Glu Trp Val Asn
            20                  25                  30

Thr Pro Ser Thr Cys Cys Leu Lys Tyr Tyr Glu Lys Val Leu Pro Arg
        35                  40                  45

Arg Leu Val Val Gly Tyr Arg Lys Ala Leu Asn Cys His Leu Pro Ala
```

```
    50                  55                  60

Ile Ile Phe Val Thr Lys Arg Asn Arg Glu Val Cys Thr Asn Pro Asn
65                  70                  75                  80

Asp Asp Trp Val Gln Glu Tyr Ile Lys Asp Pro Asn Leu Pro Leu Leu
                85                  90                  95

Pro Thr Arg Asn Leu Ser Thr Val Lys Ile Ile Thr Ala Lys Asn Gly
            100                 105                 110

Gln Pro Gln Leu Leu Asn Ser Gln
        115                 120


<210> SEQ ID NO 17
<211> LENGTH: 120
<212> TYPE: PRT
<213> ORGANISM: Homo sapiens

<400> SEQUENCE: 17

Met Lys Val Ser Glu Ala Ala Leu Ser Leu Leu Val Leu Ile Leu Ile
1               5                   10                  15

Ile Thr Ser Ala Ser Arg Ser Gln Pro Lys Val Pro Glu Trp Val Asn
            20                  25                  30

Thr Pro Ser Thr Cys Cys Leu Lys Tyr Tyr Glu Lys Val Leu Pro Arg
        35                  40                  45

Arg Leu Val Val Gly Tyr Arg Lys Ala Leu Asn Cys His Leu Pro Ala
    50                  55                  60

Ile Ile Phe Val Thr Lys Arg Asn Arg Glu Val Cys Thr Asn Pro Asn
65                  70                  75                  80

Asp Asp Trp Val Gln Glu Tyr Ile Lys Asp Pro Asn Leu Pro Leu Leu
                85                  90                  95

Pro Thr Arg Asn Leu Ser Thr Val Lys Ile Ile Thr Ala Lys Asn Gly
            100                 105                 110

Gln Pro Gln Leu Leu Asn Ser Gln
        115                 120


<210> SEQ ID NO 18
<211> LENGTH: 150
<212> TYPE: PRT
<213> ORGANISM: Homo sapiens

<400> SEQUENCE: 18

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
        115                 120                 125

Phe Ser Asn Pro Ile Ser Ser Ser Lys Arg Asn Val Ser Leu Leu Ile
    130                 135                 140
```

```
Ser Ala Asn Ser Gly Leu
145                 150


<210> SEQ ID NO 19
<211> LENGTH: 150
<212> TYPE: PRT
<213> ORGANISM: Homo sapiens

<400> SEQUENCE: 19

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
        115                 120                 125

Phe Ser Asn Pro Ile Ser Ser Ser Lys Arg Asn Val Ser Leu Leu Ile
    130                 135                 140

Ser Ala Asn Ser Gly Leu
145                 150


<210> SEQ ID NO 20
<211> LENGTH: 84
<212> TYPE: PRT
<213> ORGANISM: Homo sapiens

<400> SEQUENCE: 20

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Arg Pro Ser Cys Cys Lys Glu Val Glu Phe Trp Lys Leu Gln Val Ile
65                  70                  75                  80

Ile Val Gln Val


<210> SEQ ID NO 21
<211> LENGTH: 355
<212> TYPE: PRT
<213> ORGANISM: Homo sapiens

<400> SEQUENCE: 21

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30
```

```
Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355


<210> SEQ ID NO 22
<211> LENGTH: 397
<212> TYPE: PRT
<213> ORGANISM: Homo sapiens

<400> SEQUENCE: 22

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45
```

```
Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395
```

<210> SEQ ID NO 23
<211> LENGTH: 2502
<212> TYPE: DNA
<213> ORGANISM: Homo sapiens

<400> SEQUENCE: 23

```
tattcatcaa gtgccctcta gctgttaagt cactctgatc tctgactgca gctcctactg     60

ttggacacac ctggccggtg cttcagttag atcaaaccat tgctgaaact gaagaggaca    120

tgtcaaatat tacagatcca cagatgtggg attttgatga tctaaatttc actggcatgc    180
```

```
cacctgcaga tgaagattac agcccctgta tgctagaaac tgagacactc aacaagtatg    240
ttgtgatcat cgcctatgcc ctagtgttcc tgctgagcct gctgggaaac tccctggtga    300
tgctggtcat cttatacagc agggtcggcc gctccgtcac tgatgtctac ctgctgaacc    360
tggccttggc cgacctactc tttgccctga ccttgcccat ctgggccgcc tccaaggtga    420
atggctggat ttttggcaca ttcctgtgca aggtggtctc actcctgaag gaagtcaact    480
tctacagtgg catcctgctg ttggcctgca tcagtgtgga ccgttacctg gccattgtcc    540
atgccacacg cacactgacc cagaagcgtc acttggtcaa gtttgtttgt cttggctgct    600
ggggactgtc tatgaatctg tccctgccct tcttcctttt ccgccaggct taccatccaa    660
acaattccag tccagtttgc tatgaggtcc tgggaaatga cacagcaaaa tggcggatgg    720
tgttgcggat cctgcctcac acctttggct tcatcgtgcc gctgtttgtc atgctgttct    780
gctatggatt caccctgcgt acactgttta aggcccacat ggggcagaag caccgagcca    840
tgagggtcat ctttgctgtc gtcctcatct tcctgctttg ctggctgccc tacaacctgg    900
tcctgctggc agacaccctc atgaggaccc aggtgatcca ggagagctgt gagcgccgca    960
acaacatcgg ccgggccctg gatgccactg agattctggg atttctccat agctgcctca   1020
accccatcat ctacgccttc atcggccaaa attttcgcca tggattcctc aagatcctgg   1080
ctatgcatgg cctggtcagc aaggagttct tggcacgtca tcgtgttacc tcctacactt   1140
cttcgtctgt caatgtctct tccaacctct gaaaaccatc gatgaaggaa tatctcttct   1200
cagaaggaaa gaataaccaa caccctgagg ttgtgtgtgg aaggtgatct ggctctggac   1260
aggcactatc tgggttttgg ggggacgcta taggatgtgg ggaagttagg aactggtgtc   1320
ttcaggggcc acaccaacct tctgaggagc tgttgaggta cctccaagga ccggcctttg   1380
cacctccatg gaaacgaagc accatcattc ccgttgaacg tcacatcttt aacccactaa   1440
ctggctaatt agcatggcca catctgagcc ccgaatctga cattagatga gagaacaggg   1500
ctgaagctgt gtcctcatga gggctggatg ctctcgttga ccctcacagg agcatctcct   1560
caactctgag tgttaagcgt tgagccacca agctggtggc tctgtgtgct ctgatccgag   1620
ctcagggggg tggttttccc atctcaggtg tgttgcagtg tctgctggag acattgaggc   1680
aggcactgcc aaaacatcaa cctgccagct ggccttgtga ggagctggaa acacatgttc   1740
cccttggggg tggtggatga acaaagagaa agagggtttg gaagccagat ctatgccaca   1800
agaacccccct ttacccccat gaccaacatc gcagacacat gtgctggcca cctgctgagc   1860
cccaagtgga acgagacaag cagcccttag cccttcccct ctgcagcttc caggctggcg   1920
tgcagcatca gcatccctag aaagccatgt gcagccacca gtccattggg caggcagatg   1980
ttcctaataa agcttctgtt ccgtgcttgt ccctgtggaa gtatcttggt tgtgacagag   2040
tcaagggtgt gtgcagcatt gttggctgtt cctgcagtag aatgggggca gcacctccta   2100
agaaggcacc tctctgggtt gaagggcagt gttccctggg gctttaactc ctgctagaac   2160
agtctcttga ggcacagaaa ctcctgttca tgcccatacc cctggccaag gaagatccct   2220
ttgtccacaa gtaaaaggaa atgctcctcc agggagtctc agcttcaccc tgaggtgagc   2280
atcatcttct gggttaggcc ttgcctaggc atagccctgc ctcaagctat gtgagctcac   2340
cagtccctcc ccaaatgctt tccatgagtt gcagtttttt cctagtctgt tttccctcct   2400
tggagacagg gccctgtcgg tttattcact gtatgtcctt ggtgcctgga gcctactaaa   2460
tgctcaataa ataatgatca caggaaaaaa aaaaaaaaaa aa                       2502
```

<210> SEQ ID NO 24
<211> LENGTH: 2880
<212> TYPE: DNA
<213> ORGANISM: Homo sapiens

<400> SEQUENCE: 24

```
aggttcaaaa cattcagaga cagaaggtgg atagacaaat ctccaccttc agactggtag      60
gctcctccag aagccatcag acaggaagat gtgaaaatcc ccagcactca tcccagaatc     120
actaagtggc acctgtcctg ggccaaagtc ccaggacaga cctcattgtt cctctgtggg     180
aatacctccc caggagggca tcctggattt ccccccttgca acccaggtca gaagtttcat    240
cgtcaaggtt gtttcatctt ttttttcctg tctaacagct ctgactacca cccaaccttg     300
aggcacagtg aagacatcgg tggccactcc aataacagca ggtcacagct gctcttctgg     360
aggtgtccta caggtgaaaa gcccagcgac ccagtcagga tttaagttta cctcaaaaat     420
ggaagatttt aacatggaga gtgacagctt tgaagatttc tggaaaggtg aagatcttag     480
taattacagt tacagctcta ccctgccccc ttttctacta gatgccgccc catgtgaacc     540
agaatccctg gaaatcaaca agtattttgt ggtcattatc tatgccctgg tattcctgct     600
gagcctgctg ggaaactccc tcgtgatgct ggtcatctta tacagcaggg tcggccgctc     660
cgtcactgat gtctacctgc tgaacctagc cttggccgac ctactctttg ccctgacctt     720
gcccatctgg gccgcctcca aggtgaatgg ctggattttt ggcacattcc tgtgcaaggt     780
ggtctcactc ctgaaggaag tcaacttcta tagtggcatc ctgctactgg cctgcatcag     840
tgtggaccgt tacctggcca ttgtccatgc cacacgcaca ctgacccaga agcgctactt     900
ggtcaaattc atatgtctca gcatctgggg tctgtccttg ctcctggccc tgcctgtctt     960
acttttccga aggaccgtct actcatccaa tgttagccca gcctgctatg aggacatggg    1020
caacaataca gcaaactggc ggatgctgtt acggatcctg ccccagtcct ttggcttcat    1080
cgtgccactg ctgatcatgc tgttctgcta cggattcacc ctgcgtacgc tgtttaaggc    1140
ccacatgggg cagaagcacc gggccatgcg ggtcatcttt gctgtcgtcc tcatcttcct    1200
gctctgctgg ctgccctaca acctggtcct gctggcagac accctcatga ggacccaggt    1260
gatccaggag acctgtgagc gccgcaatca catcgaccgg gctctggatg ccaccgagat    1320
tctgggcatc cttcacagct gcctcaaccc cctcatctac gccttcattg gccagaagtt    1380
tcgccatgga ctcctcaaga ttctagctat acatggcttg atcagcaagg actccctgcc    1440
caaagacagc aggccttcct ttgttggctc ttcttcaggg cacacttcca ctactctcta    1500
agacctcctg cctaagtgca gccccgtggg gttcctccct tctcttcaca gtcacattcc    1560
aagcctcatg tccactggtt cttcttggtc tcagtgtcaa tgcagccccc attgtggtca    1620
caggaagtag aggaggccac gttcttacta gtttcccttg catggtttag aaagcttgcc    1680
ctggtgcctc accccttgcc ataattacta tgtcatttgc tggagctctg cccatcctgc    1740
ccctgagccc atggcactct atgttctaag aagtgaaaat ctacactcca gtgagacagc    1800
tctgcatact cattaggatg gctagtatca aaagaaagaa aatcaggctg gccaacgggg    1860
tgaaaccctg tctctactaa aaatacaaaa aaaaaaaaaa attagccggg cgtggtggtg    1920
agtgcctgta atcacagcta cttgggaggc tgagatggga gaatcacttg aacccgggag    1980
gcagaggttg cagtgagccg agattgtgcc cctgcactcc agcctgagcg acagtgagac    2040
tctgtctcag tccatgaaga tgtagaggag aaactggaac tctcgagcgt tgctgggggg    2100
gattgtaaaa tggtgtgacc actgcagaag acagtatggc agctttcctc aaaacttcag    2160
acatagaatt aacacatgat cctgcaattc cacttatagg aattgaccca caagaaatga    2220
```

```
aagcagggac ttgaacccat atttgtacac caatattcat agcagcttat tcacaagacc   2280

caaaaggcag aagcaaccca aatgttcatc aatgaatgaa tgaatggcta agcaaaatgt   2340

gatatgtacc taacgaagta tccttcagcc tgaaagagga atgaagtact catacatgtt   2400

acaacacgga cgaaccttga aaactttatg ctaagtgaaa taagccagac atcaacagat   2460

aaatagttta tgattccacc tacatgaggt actgagagtg aacaaattta cagagacaga   2520

aagcagaaca gtgattacca gggactgagg ggaggggagc atgggaagtg acggtttaat   2580

gggcacaggg tttatgttta ggatgttgaa aaagttctgc agataaacag tagtgatagt   2640

tgtaccgcaa tgtgacttaa tgccactaaa ttgacactta aaaatggttt aaatggtcaa   2700

ttttgttatg tatattttat atcaatttaa aaaaaaacct gagccccaaa aggtatttta   2760

atcaccaagg ctgattaaac caaggctaga accacctgcc tatatttttt gttaaatgat   2820

ttcattcaat atcttttttt taataaacca tttttacttg ggtgtttata aaaaaaaaaa   2880
```

<210> SEQ ID NO 25
<211> LENGTH: 1119
<212> TYPE: DNA
<213> ORGANISM: Homo sapiens

<400> SEQUENCE: 25

```
cacagagccc gggccgcagg cacctcctcg ccagctcttc cgctcctctc acagccgcca     60

gacccgcctg ctgagcccca tggcccgcgc tgctctctcc gccgccccca gcaatccccg    120

gctcctgcga gtggcactgc tgctcctgct cctggtagcc gctggccggc gcgcagcagg    180

agcgtccgtg gccactgaac tgcgctgcca gtgcttgcag accctgcagg gaattcaccc    240

caagaacatc caaagtgtga acgtgaagtc ccccggaccc cactgcgccc aaaccgaagt    300

catagccaca ctcaagaatg ggcggaaagc ttgcctcaat cctgcatccc ccatagttaa    360

gaaaatcatc gaaaagatgc tgaacagtga caaatccaac tgaccagaag ggaggaggaa    420

gctcactggt ggctgttcct gaaggaggcc ctgcccttat aggaacagaa gaggaaagag    480

agacacagct gcagaggcca cctggattgt gcctaatgtg tttgagcatc gcttaggaga    540

agtcttctat ttatttattt attcattagt tttgaagatt ctatgttaat attttaggtg    600

taaaataatt aagggtatga ttaactctac ctgcacactg tcctattata ttcattcttt    660

ttgaaatgtc aaccccaagt tagttcaatc tggattcata tttaatttga aggtagaatg    720

ttttcaaatg ttctccagtc attatgttaa tatttctgag gagcctgcaa catgccagcc    780

actgtgatag aggctggcgg atccaagcaa atggccaatg agatcattgt gaaggcaggg    840

gaatgtatgt gcacatctgt tttgtaactg tttagatgaa tgtcagttgt tatttattga    900

aatgatttca cagtgtgtgg tcaacatttc tcatgttgaa actttaagaa ctaaaatgtt    960

ctaaatatcc cttggacatt ttatgtcttt cttgtaaggc atactgcctt gtttaatggt   1020

agttttacag tgtttctggc ttagaacaaa ggggcttaat tattgatgtt ttcatagaga   1080

atataaaaat aaagcactta tagaaaaaaa aaaaaaaaa                          1119
```

<210> SEQ ID NO 26
<211> LENGTH: 1234
<212> TYPE: DNA
<213> ORGANISM: Homo sapiens

<400> SEQUENCE: 26

```
gagctccggg aatttccctg gcccgggact ccgggctttc cagccccaac catgcataaa     60

aggggttcgc cgttctcgga gagccacaga gcccgggcca caggcagctc cttgccagct    120
```

```
ctcctcctcg cacagccgct cgaaccgcct gctgagcccc atggcccgcg ccacgctctc    180

cgccgccccc agcaatcccc ggctcctgcg ggtggcgctg ctgctcctgc tcctggtggc    240

cgccagccgg cgcgcagcag gagcgcccct ggccactgaa ctgcgctgcc agtgcttgca    300

gaccctgcag ggaattcacc tcaagaacat ccaaagtgtg aaggtgaagt cccccggacc    360

ccactgcgcc caaaccgaag tcatagccac actcaagaat gggcagaaag cttgtctcaa    420

ccccgcatcg cccatggtta agaaaatcat cgaaaagatg ctgaaaaatg gcaaatccaa    480

ctgaccagaa ggaaggagga agcttattgg tggctgttcc tgaaggaggc cctgcccctta    540

caggaacaga agaggaaaga gagacacagc tgcagaggcc acctggattg cgcctaatgt    600

gtttgagcat cacttaggag aagtcttcta tttatttatt tatttattta tttgtttgtt    660

ttagaagatt ctatgttaat attttatgtg taaaataagg ttatgattga atctacttgc    720

acactctccc attatattta ttgtttattt taggtcaaac ccaagttagt tcaatcctga    780

ttcatattta atttgaagat agaaggtttg cagatattct ctagtcattt gttaatattt    840

cttcgtgatg acatatcaca tgtcagccac tgtgatagag gctgaggaat ccaagaaaat    900

ggccagtgag atcaatgtga cggcagggaa atgtatgtgt gtctattttg taactgtaaa    960

gatgaatgtc agttgttatt tattgaaatg atttcacagt gtgtggtcaa catttctcat   1020

gttgaagctt taagaactaa aatgttctaa atatcccttg gacattttat gtctttcttg   1080

taaggcatac tgccttgttt aatgttaatt atgcagtgtt tccctctgtg ttagagcaga   1140

gaggtttcga tatttattga tgttttcaca aagaacagga aaataaaata tttaaaaata   1200

taaaaaaaaa aaaaaaaaaa aaaaaaaaaa aaaa                               1234
```

<210> SEQ ID NO 27
<211> LENGTH: 1166
<212> TYPE: DNA
<213> ORGANISM: Homo sapiens

<400> SEQUENCE: 27

```
gctccgggaa tttccctggc ccggccgctc cgggctttcc agtctcaacc atgcataaaa     60

agggttcgcc gatcttgggg agccacacag cccgggtcgc aggcacctcc ccgccagctc    120

tcccgcttct cgcacagctt cccgacgcgt ctgctgagcc ccatggccca cgccacgctc    180

tccgccgccc ccagcaatcc ccggctcctg cgggtggcgc tgctgctcct gctcctggtg    240

gccgccagcc ggcgcgcagc aggagcgtcc gtggtcactg aactgcgctg ccagtgcttg    300

cagacactgc agggaattca cctcaagaac atccaaagtg tgaatgtaag gtcccccgga    360

ccccactgcg cccaaaccga agtcatagcc acactcaaga atgggaagaa agcttgtctc    420

aaccccgcat cccccatggt tcagaaaatc atcgaaaaga tactgaacaa ggggagcacc    480

aactgacagg agagaagtaa gaagcttatc agcgtatcat tgacacttcc tgcagggtgg    540

tccctgccct taccagagct gaaaatgaaa aagagaacag cagctttcta gggacagctg    600

gaaaggactt aatgtgtttg actatttctt acgagggttc tacttattta tgtatttatt    660

tttgaaagct tgtattttaa tattttacat gctgttattt aaagatgtga gtgtgtttca    720

tcaaacatag ctcagtcctg attatttaat tggaatatga tgggttttaa atgtgtcatt    780

aaactaatat ttagtgggag accataatgt gtcagccacc ttgataaatg acagggtggg    840

gaactggagg gtgggggat tgaaatgcaa gcaattagtg gatcactgtt agggtaaggg    900

aatgtatgta cacatctatt ttttatactt ttttttaaa aaaagaatgt cagttgttat     960

ttattcaaat tatctcacat tatgtgttca acatttttat gctgaagttt cccttagaca   1020
```

```
ttttatgtct tgcttgtagg gcataatgcc ttgtttaatg tccattctgc agcgtttctc   1080

tttcccttgg aaaagagaat ttatcattac tgttacattt gtacaaatga catgataata   1140

aaagttttat gaaaaaaaaa aaaaaa                                         1166


<210> SEQ ID NO 28
<211> LENGTH: 2475
<212> TYPE: DNA
<213> ORGANISM: Homo sapiens

<400> SEQUENCE: 28

gtgcagaagg cacgaggaag ccacagtgct ccggatcctc caatcttcgc tcctccaatc     60

tccgctcctc cacccagttc aggaacccgc gaccgctcgc agcgctctct tgaccactat    120

gagcctcctg tccagccgcg cggcccgtgt ccccggtcct tcgagctcct tgtgcgcgct    180

gttggtgctg ctgctgctgc tgacgcagcc agggcccatc gccagcgctg gtcctgccgc    240

tgctgtgttg agagagctgc gttgcgtttg tttacagacc acgcaaggag ttcatcccaa    300

aatgatcagt aatctgcaag tgttcgccat aggcccacag tgctccaagg tggaagtggt    360

agcctccctg aagaacggga aggaaatttg tcttgatcca gaagcccctt ttctaaagaa    420

agtcatccag aaaattttgg acggtggaaa caaggaaaac tgattaagag aaatgagcac    480

gcatggaaaa gtttcccagt cttcagcaga gaagttttct ggaggtctct gaacccaggg    540

aagacaagaa ggaaagattt tgttgttgtt tgtttatttg tttttccagt agttagcttt    600

cttcctggat tcctcacttt gaagagtgtg aggaaaacct atgtttgccg cttaagcttt    660

cagctcagct aatgaagtgt ttagcatagt acctctgcta tttgctgtta ttttatctgc    720

tatgctattg aagttttggc aattgactat agtgtgagcc aggaatcact ggctgttaat    780

ctttcaaagt gtcttgaatt gtaggtgact attatatttc caagaaatat tccttaagat    840

attaactgag aaggctgtgg atttaatgtg gaaatgatgt ttcataagaa ttctgttgat    900

ggaaatacac tgttatcttc acttttataa gaaataggaa atattttaat gtttcttggg    960

gaatatgtta gagaatttcc ttactcttga ttgtgggata ctatttaatt atttcacttt   1020

agaaagctga gtgtttcaca ccttatctat gtagaatata tttccttatt cagaatttct   1080

aaaagtttaa gttctatgag ggctaatatc ttatcttcct ataattttag acattcttta   1140

tctttttagt atggcaaact gccatcattt acttttaaac tttgatttta tatgctattt   1200

attaagtatt ttattaggag taccataatt ctggtagcta aatatatatt ttagatagat   1260

gaagaagcta gaaaacaggc aaattcctga ctgctagttt atatagaaat gtattctttt   1320

agtttttaaa gtaaaggcaa acttaacaat gacttgtact ctgaaagttt tggaaacgta   1380

ttcaaacaat ttgaatataa atttatcatt tagttataaa aatatatagc gacatcctcg   1440

aggccctagc atttctcctt ggataggggga ccagagagag cttggaatgt taaaaacaaa  1500

acaaaacaaa aaaaaacaag gagaagttgt ccaagggatg tcaatttttt atccctctgt   1560

atgggttaga ttttccaaaa tcataatttg aagaaggcca gcatttatgg tagaatatat   1620

aattatatat aaggtggcca cgctggggca agttccctcc ccactcacag ctttggcccc   1680

tttcacagag tagaacctgg gttagaggat tgcagaagac gagcggcagc ggggagggca   1740

gggaagatgc ctgtcgggtt tttagcacag ttcatttcac tgggattttg aagcatttct   1800

gtctgaatgt aaagcctgtt ctagtcctgg tgggacacac tggggttggg ggtgggggaa   1860

gatgcggtaa tgaaaccggt tagtcagtgt tgtcttaata tccttgataa tgctgtaaag   1920

tttattttta caaatatttc tgtttaagct atttcacctt tgtttggaaa tccttccctt   1980
```

```
ttaaagagaa aatgtgacac ttgtgaaaag gcttgtagga aagctcctcc cttttttttct   2040
ttaaaccttt aaatgacaaa cctaggtaat taatggttgt gaatttctat ttttgctttg   2100
tttttaatga acatttgtct ttcagaatag gattctgtga taatatttaa atggcaaaaa   2160
caaaacataa ttttgtgcaa ttaacaaagc tactgcaaga aaaataaaac atttcttggt   2220
aaaaacgtat gtatttatat attatatatt tatatataat atatattata tatttagcat   2280
tgctgagctt tttagatgcc tattgtgtat cttttaaagg ttttgaccat tttgttatga   2340
gtaattacat atatattaca ttcactatat taaaattgta cttttttact atgtgtctca   2400
ttggttcata gtctttattt tgtcctttga ataaacatta aaagatttct aaacttcaaa   2460
aaaaaaaaaa aaaaa                                                     2475

<210> SEQ ID NO 29
<211> LENGTH: 1677
<212> TYPE: DNA
<213> ORGANISM: Homo sapiens

<400> SEQUENCE: 29

accccttctt tccacactgc cccctgagtt cagggaattt ccccagcatc ccaaagcttg     60
agtttcctgc cagtcgggag ggatgaatgc agataaaggg agtgcagaag gcacgaggaa    120
accaaagtgc tctgtatcct ccagtctccg cgcctccacc cagctcagga acccgcgaac    180
cctctcttga ccactatgag cctcccgtcc agccgcgcgg cccgtgtccc gggtccttcg    240
ggctccttgt gcgcgctgct cgcgctgctg ctcctgctga cgccgccggg gcccctcgcc    300
agcgctggtc ctgtctctgc tgtgctgaca gagctgcgtt gcacttgttt acgcgttacg    360
ctgagagtaa accccaaaac gattggtaaa ctgcaggtgt tccccgcagg cccgcagtgc    420
tccaaggtgg aagtggtagc ctccctgaag aacgggaagc aagtttgtct ggacccggaa    480
gccccttttc taaagaaagt catccagaaa attttggaca gtggaaacaa gaaaaactga    540
gtaacaaaaa agaccatgca tcataaaatt gcccagtctt cagcggagca gttttctgga    600
gatccctgga cccagtaaga ataagaagga agggttggtt tttttccatt ttctacatgg    660
attccctact ttgaagagtg tgggggaaag cctacgcttc tccctgaagt ttacagctca    720
gctaatgaag tactaatata gtatttccac tatttactgt tattttacct gataagttat    780
tgaacccttt ggcaattgac catattgtga gcaaagaatc actggttatt agtctttcaa    840
tgaatattga attgaagata actattgtat ttctatcata cattccttaa agtcttaccg    900
aaaaggctgt ggatttcgta tggaaataat gttttattag tgtgctgttg agggaggtat    960
cctgttgttc ttactcactc ttctcataaa ataggaaata ttttagttct gtttcttggg   1020
gaatatgtta ctctttaccc taggatgcta tttaagttgt actgtattag aacactgggt   1080
gtgtcatacc gttatctgtg cagaatatat ttccttattc agaatttcta aaaatttaag   1140
ttctgtaagg gctaatatat tctcttccta tggttttaga cgtttgatgt cttcttagta   1200
tggcataatg tcatgattta ctcattaaac tttgattttg tatgctattt tttcactata   1260
ggatgactat aattctggtc actaaatata cactttagat agatgaagaa gcccaaaaac   1320
agataaattc ctgattgcta atttacatag aaatgtattc tcttggtttt ttaaataaaa   1380
gcaaaattaa caatgatctg tgctctgaaa gttttgaaaa tatatttgaa caatttgaat   1440
ataaattcat catttagtcc tcaaaatata tatagcattg ctaagatttt cagatatcta   1500
ttgtggatct tttaaaggtt ttgaccattt tgttatgagg aattatacat gtatcacatt   1560
cactatatta aaattgcact tttatttttt cctgtgtgtc atgttggttt ttggtacttg   1620
```

tattgtcatt tggagaaaca ataaaagatt tctaaaccaa aaaaaaaaaa aaaaaaa 1677

<210> SEQ ID NO 30
<211> LENGTH: 1307
<212> TYPE: DNA
<213> ORGANISM: Homo sapiens

<400> SEQUENCE: 30
acttatctgc agacttgtag gcagcaactc accctcactc agaggtcttc tggttctgga 60
aacaactcta gctcagcctt ctccaccatg agcctcagac ttgataccac cccttcctgt 120
aacagtgcga gaccacttca tgccttgcag gtgctgctgc ttctgtcatt gctgctgact 180
gctctggctt cctccaccaa aggacaaact aagagaaact tggcgaaagg caaagaggaa 240
agtctagaca gtgacttgta tgctgaactc cgctgcatgt gtataaagac aacctctgga 300
attcatccca aaaacatcca aagtttggaa gtgatcggga aaggaaccca ttgcaaccaa 360
gtcgaagtga tagccacact gaaggatggg aggaaaatct gcctggaccc agatgctccc 420
agaatcaaga aaattgtaca gaaaaaattg gcaggtgatg aatctgctga ttaatttgtt 480
ctgtttctgc caaacttctt taactcccag gaagggtaga attttgaaac cttgattttc 540
tagagttctc atttattcag gatacctatt cttactgtat taaaatttgg atatgtgttt 600
cattctgtct caaaaatcac attttattct gagaaggttg gttaaaagat ggcagaaaga 660
agatgaaaat aaataagcct ggtttcaacc ctctaattct tgcctaaaca ttggactgta 720
ctttgcattt ttttctttaa aaatttctat tctaacacaa cttggttgat tttcctggt 780 ctactttatg gttattagac atactcatgg gtattattag atttcataat ggtcaatgat 840
aataggaatt acatggagcc caacagagaa tatttgctca atacattttt gttaatatat 900
ttaggaactt aatggagtct ctcagtgtct tagtcctagg atgtcttatt taaaatactc 960
cctgaaagtt tattctgatg tttattttag ccatcaaaca ctaaaataat aaattggtga 1020
atatgaatct tataaactgt ggttagctgg tttaaagtga atatatttgc cactagtaga 1080
acaaaaatag atgatgaaaa tgaattaaca tatctacata gttataattc tatcattaga 1140
atgagcctta taaataagta caatatagga cttcaacctt actagactcc taattctaaa 1200
ttctactttt ttcatcaaca gaactttcat tcattttta aaccctaaaa cttataccca 1260
cactattctt acaaaaatat tcacatgaaa taaaaatttg ctattga 1307

<210> SEQ ID NO 31
<211> LENGTH: 1718
<212> TYPE: DNA
<213> ORGANISM: Homo sapiens

<400> SEQUENCE: 31
gagggtgcat aagttctcta gtagggtgat gatataaaaa gccaccggag cactccataa 60
ggcacaaact ttcagagaca gcagagcaca caagcttcta ggacaagagc caggaagaaa 120
ccaccggaag gaaccatctc actgtgtgta aacatgactt ccaagctggc cgtggctctc 180
ttggcagcct tcctgatttc tgcagctctg tgtgaaggtg cagttttgcc aaggagtgct 240
aaagaactta gatgtcagtg cataaagaca tactccaaac ctttccaccc caaatttatc 300
aaagaactga gagtgattga gagtggacca cactgcgcca acacagaaat tattgtaaag 360
ctttctgatg gaagagagct ctgtctggac cccaaggaaa actgggtgca gagggttgtg 420
gagaagtttt tgaagagggc tgagaattca taaaaaaatt cattctctgt ggtatccaag 480
aatcagtgaa gatgccagtg aaacttcaag caaatctact tcaacacttc atgtattgtg 540

```
tgggtctgtt gtagggttgc cagatgcaat acaagattcc tggttaaatt tgaatttcag    600
taaacaatga atagtttttc attgtaccat gaaatatcca gaacatactt atatgtaaag    660
tattatttat ttgaatctac aaaaaacaac aaataatttt taaatataag gattttccta    720
gatattgcac gggagaatat acaaatagca aaattgaggc caagggccaa gagaatatcc    780
gaactttaat ttcaggaatt gaatgggttt gctagaatgt gatatttgaa gcatcacata    840
aaaatgatgg gacaataaat tttgccataa agtcaaattt agctggaaat cctggatttt    900
tttctgttaa atctggcaac cctagtctgc tagccaggat ccacaagtcc ttgttccact    960
gtgccttggt ttctccttta tttctaagtg gaaaaagtat tagccaccat cttacctcac   1020
agtgatgttg tgaggacatg tggaagcact ttaagttttt tcatcataac ataaattatt   1080
ttcaagtgta acttattaac ctatttatta tttatgtatt tatttaagca tcaaatattt   1140
gtgcaagaat ttggaaaaat agaagatgaa tcattgattg aatagttata aagatgttat   1200
agtaaattta ttttatttta gatattaaat gatgttttat tagataaatt tcaatcaggg   1260
tttttagatt aaacaaacaa acaattgggt acccagttaa attttcattt cagataaaca   1320
acaaataatt ttttagtata agtacattat tgtttatctg aaattttaat tgaactaaca   1380
atcctagttt gatactccca gtcttgtcat tgccagctgt gttggtagtg ctgtgttgaa   1440
ttacggaata atgagttaga actattaaaa cagccaaaac tccacagtca atattagtaa   1500
tttcttgctg gttgaaactt gtttattatg tacaaataga ttcttataat attatttaaa   1560
tgactgcatt tttaaataca aggctttata tttttaactt taagatgttt ttatgtgctc   1620
tccaaatttt ttttactgtt tctgattgta tggaaatata aaagtaaata tgaaacattt   1680
aaaatataat ttgttgtcaa agtaaaaaaa aaaaaaaa                           1718
```

<210> SEQ ID NO 32
<211> LENGTH: 1691
<212> TYPE: DNA
<213> ORGANISM: Homo sapiens

<400> SEQUENCE: 32

```
aacttcagtt tgttggctgc ggcagcaggt agcaaagtga cgccgagggc ctgagtgctc     60
cagtagccac cgcatctgga gaaccagcgg ttaccatgga ggggatcagt atatacactt    120
cagataacta caccgaggaa atgggctcag gggactatga ctccatgaag gaaccctgtt    180
tccgtgaaga aaatgctaat ttcaataaaa tcttcctgcc caccatctac tccatcatct    240
tcttaactgg cattgtgggc aatggattgg tcatcctggt catgggttac cagaagaaac    300
tgagaagcat gacggacaag tacaggctgc acctgtcagt ggccgacctc ctctttgtca    360
tcacgcttcc cttctgggca gttgatgccg tggcaaactg gtactttggg aacttcctat    420
gcaaggcagt ccatgtcatc tacacagtca acctctacag cagtgtcctc atcctggcct    480
tcatcagtct ggaccgctac ctggccatcg tccacgccac caacagtcag aggccaagga    540
agctgttggc tgaaaaggtg gtctatgttg gcgtctggat ccctgccctc ctgctgacta    600
ttcccgactt catctttgcc aacgtcagtg aggcagatga cagatatatc tgtgaccgct    660
tctaccccaa tgacttgtgg gtggttgtgt tccagtttca gcacatcatg gttggcctta    720
tcctgcctgg tattgtcatc ctgtcctgct attgcattat catctccaag ctgtcacact    780
ccaagggcca ccagaagcgc aaggccctca agaccacagt catcctcatc ctggctttct    840
tcgcctgttg gctgccttac tacattggga tcagcatcga ctccttcatc ctcctggaaa    900
tcatcaagca agggtgtgag tttgagaaca ctgtgcacaa gtggatttcc atcaccgagg    960
```

```
ccctagcttt cttccactgt tgtctgaacc ccatcctcta tgctttcctt ggagccaaat   1020
ttaaaacctc tgcccagcac gcactcacct ctgtgagcag agggtccagc ctcaagatcc   1080
tctccaaagg aaagcgaggt ggacattcat ctgtttccac tgagtctgag tcttcaagtt   1140
ttcactccag ctaacacaga tgtaaaagac tttttttat acgataaata actttttttt    1200
aagttacaca tttttcagat ataaaagact gaccaatatt gtacagtttt tattgcttgt   1260
tggatttttg tcttgtgttt ctttagtttt tgtgaagttt aattgactta tttatataaa   1320
ttttttttgt ttcatattga tgtgtgtcta ggcaggacct gtggccaagt tcttagttgc   1380
tgtatgtctc gtggtaggac tgtagaaaag ggaactgaac attccagagc gtgtagtgaa   1440
tcacgtaaag ctagaaatga tccccagctg tttatgcata gataatctct ccattcccgt   1500
ggaacgtttt tcctgttctt aagacgtgat tttgctgtag aagatggcac ttataaccaa   1560
agcccaaagt ggtatagaaa tgctggtttt tcagttttca ggagtgggtt gatttcagca   1620
cctacagtgt acagtcttgt attaagttgt taataaaagt acatgttaaa cttaaaaaaa   1680
aaaaaaaaaa a                                                          1691
```

<210> SEQ ID NO 33
<211> LENGTH: 3545
<212> TYPE: DNA
<213> ORGANISM: Homo sapiens

<400> SEQUENCE: 33

```
gccgcacttt cactctccgt cagccgcatt gcccgctcgg cgtccggccc ccgacccgcg     60
ctcgtccgcc cgcccgcccg cccgcccgcg ccatgaacgc caaggtcgtg gtcgtgctgg    120
tcctcgtgct gaccgcgctc tgcctcagcg acgggaagcc cgtcagcctg agctacagat    180
gcccatgccg attcttcgaa agccatgttg ccagagccaa cgtcaagcat ctcaaaattc    240
tcaacactcc aaactgtgcc cttcagattg tagcccggct gaagaacaac aacagacaag    300
tgtgcattga cccgaagcta aagtggattc aggagtacct ggagaaagct ttaaacaaga    360
ggttcaagat gtgagagggt cagacgcctg aggaaccctt acagtaggag cccagctctg    420
aaaccagtgt tagggaaggg cctgccacag cctcccctgc cagggcaggg ccccaggcat    480
tgccaagggc tttgttttgc acactttgcc atattttcac catttgatta tgtagcaaaa    540
tacatgacat ttatttttca tttagtttga ttattcagtg tcactggcga cacgtagcag    600
cttagactaa ggccattatt gtacttgcct tattagagtg tctttccacg gagccactcc    660
tctgactcag ggctcctggg ttttgtattc tctgagctgt gcaggtgggg agactgggct    720
gagggagcct ggccccatgg tcagccctag ggtggagagc caccaagagg gacgcctggg    780
ggtgccagga ccagtcaacc tgggcaaagc ctagtgaagg cttctctctg tgggatggga    840
tggtggaggg ccacatggga ggctcacccc cttctccatc cacatgggag ccgggtctgc    900
ctcttctggg agggcagcag ggctaccctg agctgaggca gcagtgtgag gccagggcag    960
agtgagaccc agccctcatc ccgagcacct ccacatcctc cacgttctgc tcatcattct   1020
ctgtctcatc catcatcatg tgtgtccacg actgtctcca tggccccgca aaaggactct   1080
caggaccaaa gctttcatgt aaactgtgca ccaagcagga aatgaaaatg tcttgtgtta   1140
cctgaaaaca ctgtgcacat ctgtgtcttg tttggaatat tgtccattgt ccaatcctat   1200
gtttttgttc aaagccagcg tcctcctctg tgaccaatgt cttgatgcat gcactgttcc   1260
ccctgtgcag ccgctgagcg aggagatgct ccttgggccc tttgagtgca gtcctgatca   1320
gagccgtggt cctttggggt gaactacctt ggttccccca ctgatcacaa aaacatggtg   1380
```

```
ggtccatggg cagagcccaa gggaattcgg tgtgcaccag ggttgacccc agaggattgc   1440
tgccccatca gtgctccctc acatgtcagt accttcaaac tagggccaag cccagcactg   1500
cttgaggaaa acaagcattc acaacttgtt tttggttttt aaaacccagt ccacaaaata   1560
accaatcctg gacatgaaga ttctttccca attcacatct aacctcatct tcttcaccat   1620
ttggcaatgc catcatctcc tgccttcctc ctgggccctc tctgctctgc gtgtcacctg   1680
tgcttcgggc ccttcccaca ggacatttct ctaagagaac aatgtgctat gtgaagagta   1740
agtcaacctg cctgacattt ggagtgttcc ccttccactg agggcagtcg atagagctgt   1800
attaagccac ttaaaatgtt cacttttgac aaaggcaagc acttgtgggt ttttgttttg   1860
tttttcattc agtcttacga atacttttgc cctttgatta aagactccag ttaaaaaaaa   1920
ttttaatgaa gaaagtggaa aacaaggaag tcaaagcaag gaaactatgt aacatgtagg   1980
aagtaggaag taaattatag tgatgtaatc ttgaattgta actgttcttg aatttaataa   2040
tctgtagggt aattagtaac atgtgttaag tattttcata agtatttcaa attggagctt   2100
catggcagaa ggcaaaccca tcaacaaaaa ttgtccctta aacaaaaatt aaaatcctca   2160
atccagctat gttatattga aaaaatagag cctgagggat ctttactagt tataaagata   2220
cagaactctt tcaaaacctt ttgaaattaa cctctcacta taccagtata attgagtttt   2280
cagtggggca gtcattatcc aggtaatcca agatatttta aaatctgtca cgtagaactt   2340
ggatgtacct gcccccaatc catgaaccaa gaccattgaa ttcttggttg aggaaacaaa   2400
catgacccta aatcttgact acagtcagga aaggaatcat ttctatttct cctccatggg   2460
agaaaataga taagagtaga aactgcaggg aaaattattt gcataacaat tcctctacta   2520
acaatcagct ccttcctgga gactgcccag ctaaagcaat atgcatttaa atacagtctt   2580
ccatttgcaa gggaaaagtc tcttgtaatc cgaatctctt tttgctttcg aactgctagt   2640
caagtgcgtc cacgagctgt ttactaggga tccctcatct gtccctccgg gacctggtgc   2700
tgcctctacc tgacactccc ttgggctccc tgtaacctct tcagaggccc tcgctgccag   2760
ctctgtatca ggacccagag gaaggggcca gaggctcgtt gactggctgt gtgttgggat   2820
tgagtctgtg ccacgtgttt gtgctgtggt gtgtccccct ctgtccaggc actgagatac   2880
cagcgaggag gctccagagg gcactctgct tgttattaga gattacctcc tgagaaaaaa   2940
ggttccgctt ggagcagagg ggctgaatag cagaaggttg cacctccccc aaccttagat   3000
gttctaagtc tttccattgg atctcattgg acccttccat ggtgtgatcg tctgactggt   3060
gttatcaccg tgggctccct gactgggagt tgatcgcctt tcccaggtgc tacacccttt   3120
tccagctgga tgagaatttg agtgctctga tccctctaca gagcttccct gactcattct   3180
gaaggagccc cattcctggg aaatattccc tagaaacttc caaatcccct aagcagacca   3240
ctgataaaac catgtagaaa atttgttatt ttgcaacctc gctggactct cagtctctga   3300
gcagtgaatg attcagtgtt aaatgtgatg aatactgtat tttgtattgt ttcaattgca   3360
tctcccagat aatgtgaaaa tggtccagga gaaggccaat tcctatacgc agcgtgcttt   3420
aaaaaataaa taagaaacaa ctctttgaga aacaacaatt tctactttga agtcatacca   3480
atgaaaaaat gtatatgcac ttataatttt cctaataaag ttctgtactc aaatgtagcc   3540
accaa                                                               3545
```

<210> SEQ ID NO 34
<211> LENGTH: 2896
<212> TYPE: DNA
<213> ORGANISM: Homo sapiens

<400> SEQUENCE: 34

```
ccactctaag gaatgcggtc cctttgacag gcgaaaaact gaagttggaa aagacaaagt     60
gatttgttca aaattgaaat ttgaaacttg acatttggtc agtgggccct atgtaggaaa    120
aaacctccaa gagagctagg gttcctctca gagaggaaag acaggtcctt aggtcctcac    180
cctcccgtct ccttgccctt gcagttctgg gaactggaca gattggacaa ctataacgac    240
acctccctgg tggaaaatca tctctgccct gccacagagg ggcccctcat ggcctccttc    300
aaggccgtgt tcgtgcccgt ggcctacagc ctcatcttcc tcctgggcgt gatcggcaac    360
gtcctggtgc tggtgatcct ggagcggcac cggcagacac gcagttccac ggagaccttc    420
ctgttccacc tggccgtggc cgacctcctg ctggtcttca tcttgccctt tgccgtggcc    480
gagggctctg tgggctgggt cctggggacc ttcctctgca aaactgtgat tgccctgcac    540
aaagtcaact tctactgcag cagcctgctc ctggcctgca tcgccgtgga ccgctacctg    600
gccattgtcc acgccgtcca tgcctaccgc caccgccgcc tcctctccat ccacatcacc    660
tgtgggacca tctggctggt gggcttcctc cttgccttgc cagagattct cttcgccaaa    720
gtcagccaag gccatcacaa caactccctg ccacgttgca ccttctccca agagaaccaa    780
gcagaaacgc atgcctggtt cacctcccga ttcctctacc atgtggcggg attcctgctg    840
cccatgctgg tgatgggctg gtgctacgtg gggtagtgc acaggttgcg ccaggcccag     900
cggcgccctc agcggcagaa ggcagtcagg gtggccatcc tggtgacaag catcttcttc    960
ctctgctggt caccctacca catcgtcatc ttcctggaca ccctggcgag gctgaaggcc   1020
gtggacaata cctgcaagct gaatggctct ctccccgtgg ccatcaccat gtgtgagttc   1080
ctgggcctgg cccactgctg cctcaacccc atgctctaca ctttcgccgg cgtgaagttc   1140
cgcagtgacc tgtcgcggct cctgacgaag ctgggctgta ccggccctgc ctccctgtgc   1200
cagctcttcc ctagctggcg caggagcagt ctctctgagt cagagaatgc cacctctctc   1260
accacgttct aggtcccagt gtcccctttt attgctgctt ttccttgggg caggcagtga   1320
tgctggatgc tccttccaac aggagctggg atcctaaggg ctcaccgtgg ctaagagtgt   1380
cctaggagta tcctcatttg ggtagctag aggaaccaac cccatttct agaacatccc     1440
tgccagctct tctgccggcc ctggggctag gctggagccc agggagcgga aagcagctca   1500
aaggcacagt gaaggctgtc cttacccatc tgcacccccc tgggctgaga gaacctcacg   1560
cacctcccat cctaatcatc caatgctcaa gaaacaactt ctacttctgc ccttgccaac   1620
ggagagcgcc tgcccctccc agaacacact ccatcagctt aggggctgct gacctccaca   1680
gcttcccctc tctcctcctg cccacctgtc aaacaaagcc agaagctgag caccagggga   1740
tgagtggagg ttaaggctga ggaaaggcca gctggcagca gagtgtggcc ttcggacaac   1800
tcagtcccta aaaacacaga cattctgcca ggcccccaag cctgcagtca tcttgaccaa   1860
gcaggaagct cagactggtt gagttcaggt agctgcccct ggctctgacc gaaacagcgc   1920
tgggtccacc ccatgtcacc ggatcctggg tggtctgcag gcagggctga ctctaggtgc   1980
ccttggaggc cagccagtga cctgaggaag cgtgaaggcc gagaagcaag aaagaaaccc   2040
gacagaggga agaaaagagc tttcttcccg aaccccaagg agggagatgg atcaatcaaa   2100
cccggcggtc ccctccgcca ggcgagatgg ggtggggtgg agaactccta gggtggctgg   2160
gtccagggga tgggaggttg tgggcattga tggggaagga ggctggcttg tcccctcctc   2220
actcccttcc cataagctat agacccgagg aaactcagag tcggaacgga gaaaggtgga   2280
ctggaagggg cccgtgggag tcatctcaac catcccctcc gtggcatcac cttaggcagg   2340
```

```
gaagtgtaag aaacacactg aggcagggaa gtccccaggc cccaggaagc cgtgccctgc   2400
ccccgtgagg atgtcactca gatggaaccg caggaagctg ctccgtgctt gtttgctcac   2460
ctggggtgtg ggaggcccgt ccggcagttc tgggtgctcc ctaccacctc cccagccttt   2520
gatcaggtgg ggagtcaggg acccctgccc ttgtcccact caagccaagc agccaagctc   2580
cttgggaggc cccactgggg aaataacagc tgtggctcac gtgagagtgt cttcacggca   2640
ggacaacgag gaagccctaa gacgtccctt ttttctctga gtatctcctc gcaagctggg   2700
taatcgatgg gggagtctga agcagatgca aagaggcaag aggctggatt ttgaattttc   2760
tttttaataa aaaggcacct ataaaacagg tcaatacagt acaggcagca cagagacccc   2820
cggaacaagc ctaaaaattg tttcaaaata aaaaccaaga agatgtcttc acatattgta   2880
aaaaaaaaaa aaaaaa                                                   2896
```

```
<210> SEQ ID NO 35
<211> LENGTH: 2919
<212> TYPE: DNA
<213> ORGANISM: Homo sapiens

<400> SEQUENCE: 35
```

```
aaaaaaaaaa agtgatgagt tgtgaggcag gtcgcggccc tactgcctca ggagacgatg     60
cgcagctcat ttgcttaaat ttgcagctga cggctgccac ctctctagag gcacctggcg    120
gggagcctct caacataaga cagtgaccag tctggtgact cacagccggc acagccatga    180
actacccgct aacgctggaa atggacctcg agaacctgga ggacctgttc tgggaactgg    240
acagattgga caactataac gacacctccc tggtggaaaa tcatctctgc cctgccacag    300
aggggcccct catggcctcc ttcaaggccg tgttcgtgcc cgtggcctac agcctcatct    360
tcctcctggg cgtgatcggc aacgtcctgg tgctggtgat cctggagcgg caccggcaga    420
cacgcagttc cacggagacc ttcctgttcc acctggccgt ggccgacctc ctgctggtct    480
tcatcttgcc ctttgccgtg gccgagggct ctgtgggctg ggtcctgggg accttcctct    540
gcaaaactgt gattgccctg cacaaagtca acttctactg cagcagcctg ctcctggcct    600
gcatcgccgt ggaccgctac ctggccattg tccacgccgt ccatgcctac cgccaccgcc    660
gcctcctctc catccacatc acctgtggga ccatctggct ggtgggcttc ctccttgcct    720
tgccagagat tctcttcgcc aaagtcagcc aaggccatca caacaactcc ctgccacgtt    780
gcaccttctc ccaagagaac caagcagaaa cgcatgcctg gttcacctcc cgattcctct    840
accatgtggc gggattcctg ctgcccatgc tggtgatggg ctggtgctac gtgggggtag    900
tgcacaggtt gcgccaggcc cagcggcgcc ctcagcggca gaaggcagtc agggtggcca    960
tcctggtgac aagcatcttc ttcctctgct ggtcacccta ccacatcgtc atcttcctgg   1020
acaccctggc gaggctgaag gccgtggaca atacctgcaa gctgaatggc tctctccccg   1080
tggccatcac catgtgtgag ttcctgggcc tggcccactg ctgcctcaac cccatgctct   1140
acactttcgc cggcgtgaag ttccgcagtg acctgtcgcg gctcctgacg aagctgggct   1200
gtaccggccc tgcctccctg tgccagctct tccctagctg gcgcaggagc agtctctctg   1260
agtcagagaa tgccacctct ctcaccacgt tctaggtccc agtgtcccct tttattgctg   1320
cttttccttg gggcaggcag tgatgctgga tgctccttcc aacaggagct gggatcctaa   1380
gggctcaccg tggctaagag tgtcctagga gtatcctcat ttggggtagc tagaggaacc   1440
aacccccatt tctagaacat ccctgccagc tcttctgccg gccctggggc taggctggag   1500
cccagggagc ggaaagcagc tcaaaggcac agtgaaggct gtccttaccc atctgcaccc   1560
```

```
ccctgggctg agagaacctc acgcacctcc catcctaatc atccaatgct caagaaacaa   1620

cttctacttc tgcccttgcc aacggagagc gcctgcccct cccagaacac actccatcag   1680

cttaggggct gctgacctcc acagcttccc ctctctcctc ctgcccacct gtcaaacaaa   1740

gccagaagct gagcaccagg ggatgagtgg aggttaaggc tgaggaaagg ccagctggca   1800

gcagagtgtg gccttcggac aactcagtcc ctaaaaacac agacattctg ccaggccccc   1860

aagcctgcag tcatcttgac caagcaggaa gctcagactg gttgagttca ggtagctgcc   1920

cctggctctg accgaaacag cgctgggtcc accccatgtc accggatcct gggtggtctg   1980

caggcagggc tgactctagg tgcccttgga ggccagccag tgacctgagg aagcgtgaag   2040

gccgagaagc aagaaagaaa cccgacagag ggaagaaaag agctttcttc ccgaacccca   2100

aggagggaga tggatcaatc aaacccggcg gtcccctccg ccaggcgaga tggggtgggg   2160

tggagaactc ctagggtggc tgggtccagg ggatgggagg ttgtgggcat tgatggggaa   2220

ggaggctggc ttgtcccctc ctcactccct tcccataagc tatagacccg aggaaactca   2280

gagtcggaac ggagaaaggt ggactggaag gggcccgtgg gagtcatctc aaccatcccc   2340

tccgtggcat caccttaggc agggaagtgt aagaaacaca ctgaggcagg gaagtcccca   2400

ggccccagga agccgtgccc tgccccgtg aggatgtcac tcagatggaa ccgcaggaag   2460

ctgctccgtg cttgtttgct cacctggggt gtgggaggcc cgtccggcag ttctgggtgc   2520

tccctaccac ctccccagcc tttgatcagg tggggagtca gggacccctg cccttgtccc   2580

actcaagcca agcagccaag ctccttggga ggccccactg gggaaataac agctgtggct   2640

cacgtgagag tgtcttcacg gcaggacaac gaggaagccc taagacgtcc cttttttctc   2700

tgagtatctc ctcgcaagct gggtaatcga tgggggagtc tgaagcagat gcaaagaggc   2760

aagaggctgg attttgaatt ttctttttaa taaaaaggca cctataaaac aggtcaatac   2820

agtacaggca gcacagagac ccccggaaca agcctaaaaa ttgtttcaaa ataaaaacca   2880

agaagatgtc ttcacatatt gtaaaaaaaa aaaaaaaaa                          2919
```

<210> SEQ ID NO 36
<211> LENGTH: 1219
<212> TYPE: DNA
<213> ORGANISM: Homo sapiens

<400> SEQUENCE: 36

```
gagaagatgt ttgaaaaaac tgactctgct aatgagcctg gactcagagc tcaagtctga     60

actctacctc cagacagaat gaagttcatc tcgacatctc tgcttctcat gctgctggtc    120

agcagcctct ctccagtcca aggtgttctg gaggtctatt acacaagctt gaggtgtaga    180

tgtgtccaag agagctcagt ctttatccct agacgcttca ttgatcgaat tcaaatcttg    240

ccccgtggga atggttgtcc aagaaaagaa atcatagtct ggaagaagaa caagtcaatt    300

gtgtgtgtgg accctcaagc tgaatggata caaagaatga tggaagtatt gagaaaaaga    360

agttcttcaa ctctaccagt tccagtgttt aagagaaaga ttccctgatg ctgatatttc    420

cactaagaac acctgcattc ttcccttatc cctgctctgg attttagttt tgtgcttagt    480

taaatctttt ccaggaaaaa gaacttcccc atacaaataa gcatgagact atgtaaaaat    540

aaccttgcag aagctgatgg ggcaaactca agcttcttca ctcacagcac cctatataca    600

cttggagttt gcattcttat tcatcaggga ggaaagtttc tttgaaaata gttattcagt    660

tataagtaat acaggattat tttgattata tacttgttgt ttaatgttta aaatttctta    720

gaaaacaatg gaatgagaat ttaagcctca aatttgaaca tgtggcttga attaagaaga    780
```

```
aaattatggc atatattaaa agcaggcttc tatgaaagac tcaaaaagct gcctgggagg    840
cagatggaac ttgagcctgt caagaggcaa aggaatccat gtagtagata tcctctgctt    900
aaaaactcac tacggaggag aattaagtcc tacttttaaa gaatttcttt ataaaattta    960
ctgtctaaga ttaatagcat tcgaagatcc ccagacttca tagaatactc agggaaagca   1020
tttaaagggt gatgtacaca tgtatccttt cacacattg ccttgacaaa cttctttcac   1080
tcacatcttt ttcactgact ttttttgtgg ggggcggggc cggggggact ctggtatcta   1140
attctttaat gattcctata aatctaatga cattcaataa agttgagcaa acattttact   1200
taaaaaaaaa aaaaaaaaa                                                1219
```

<210> SEQ ID NO 37
<211> LENGTH: 1953
<212> TYPE: DNA
<213> ORGANISM: Homo sapiens

<400> SEQUENCE: 37

```
gcagaccttg cttcatgagc aagctcatct ctggaacaaa ctggcaaagc atctctgctg     60
gtgttcatca gaacagacac catggcagag catgattacc atgaagacta tgggttcagc    120
agtttcaatg acagcagcca ggaggagcat caagacttcc tgcagttcag caaggtcttt    180
ctgccctgca tgtacctggt ggtgtttgtc tgtggtctgg tggggaactc tctggtgctg    240
gtcatatcca tcttctacca taagttgcag agcctgacgg atgtgttcct ggtgaaccta    300
cccctggctg acctggtgtt tgtctgcact ctgcccttct gggcctatgc aggcatccat    360
gaatgggtgt ttggccaggt catgtgcaag agcctactgg gcatctacac tattaacttc    420
tacacgtcca tgctcatcct cacctgcatc actgtggatc gtttcattgt agtggttaag    480
gccaccaagg cctacaacca gcaagccaag aggatgacct ggggcaaggt caccagcttg    540
ctcatctggg tgatatccct gctggtttcc ttgccccaaa ttatctatgg caatgtcttt    600
aatctcgaca agctcatatg tggttaccat gacgaggcaa tttccactgt ggttcttgcc    660
acccagatga cactggggtt cttcttgcca ctgctcacca tgattgtctg ctattcagtc    720
ataatcaaaa cactgcttca tgctggaggc ttccagaagc acagatctct aaagatcatc    780
ttcctggtga tggctgtgtt cctgctgacc cagatgccct tcaacctcat gaagttcatc    840
cgcagcacac actgggaata ctatgccatg accagctttc actacaccat catggtgaca    900
gaggccatcg catacctgag ggcctgcctt aaccctgtgc tctatgcctt tgtcagcctg    960
aagtttcgaa agaacttctg gaaacttgtg aaggacattg gttgcctccc ttaccttggg   1020
gtctcacatc aatggaaatc ttctgaggac aattccaaga ctttttctgc ctcccacaat   1080
gtggaggcca ccagcatgtt ccagttatag gccttgccag ggtttcgaga agctgctctg   1140
gaatttgcaa gtcatggctg tgccctcttg atgtggtgag gcaggctttg tttatagctt   1200
gcgcattctc atggagaagt tatcagacac tctggctggt ttggaatgct tcttctcagg   1260
catgaacatg tactgttctc ttcttgaaca ctcatgctga aagcccaagt agggggtcta   1320
aaatttttaa ggactttcct tcctccatct ccaagaatgc tgaaaccaag gggggatgaca   1380
tgtgactcct atgatctcag gttctccttg attgggactg gggctgaagg ttgaagaggt   1440
gagcacggcc aacaaagctg ttgatggtag gtggcacact gggtgcccaa gctcagaagg   1500
ctcttctgac tactgggcaa agagtgtaga tcagagcagc agtgaaaaca agtgctggca   1560
ccaccaggca cctcacagaa atgagatcag gctctgcctc accttggggc ttgacttttg   1620
tataggtaga tgttcagatt gctttgatta atccagaata actagcacca gggactatga   1680
```

```
atgggcaaaa ctgaattata agaggctgat aattccagtg gtccatggaa tgcttgaaaa   1740

atgtgcaaaa cagcgtttaa gactgtaatg aatctaagca gcatttctga agtggactct   1800

ttggtggctt tgcattttaa aaatgaaatt ttccaatgtc tgccacacaa acgtatgtaa   1860

atgtatatac ccacacacat acacacatat gtcatatatt actagcatat gagtttcata   1920

gctaagaaat aaaactgtta aagtctccaa act                                1953
```

```
<210> SEQ ID NO 38
<211> LENGTH: 2344
<212> TYPE: DNA
<213> ORGANISM: Homo sapiens

<400> SEQUENCE: 38

ggtgcgtccg cgggtggctg ccccgcaggt gcgcgcggcc ggggctggcg gcgactctct     60

ccaccgggcc gcccgggagg ctcatgcagc gcggctgggt cccgcggcgc ccggatcggg    120

gaagtgaaag tgcctcggag gaggagggcc ggtccggcag tgcagccgcc tcacaggtcg    180

gcggacgggc caggcgggcg gcctcctgaa ccgaaccgaa tcggctcctc gggccgtcgt    240

cctcccgccc ctcctcgccc gccgccggag ttttctttcg gtttcttcca agattcctgg    300

ccttccctcg acggagccgg gcccagtgcg gggcgcagg gcgcgggagc tccacctcct    360

cggctttccc tgcgtccaga ggctggcatg gcgcgggccg agtactgagc gcacggtcgg    420

ggcacagcag ggccgggggg tgcagctggc tcgcgcctcc tctccggccg ccgtctcctc    480

cggtccccgg cgaaagccat tgagacacca gctggacgtc acgcgccgga gcatgtctgg    540

gagtcagagc gaggtggctc catccccgca gagtccgcgg agccccgaga tgggacggga    600

cttgcggccc gggtcccgcg tgctcctgct cctgcttctg ctcctgctgg tgtacctgac    660

tcagccaggc aatggcaacg agggcagcgt cactggaagt tgttattgtg gtaaaagaat    720

ttcttccgac tccccgccat cggttcagtt catgaatcgt ctccggaaac acctgagagc    780

ttaccatcgg tgtctatact acacgaggtt ccagctcctt tcctggagcg tgtgtggggg    840

caacaaggac ccatgggttc aggaattgat gagctgtctt gatctcaaag aatgtggaca    900

tgcttactcg gggattgtgg cccaccagaa gcatttactt cctaccagcc ccccaatttc    960

tcaggcctca gagggggcat cttcagatat ccacacccct gcccagatgc tcctgtccac   1020

cttgcagtcc actcagcgcc ccaccctccc agtaggatca ctgtcctcgg acaaagagct   1080

cactcgtccc aatgaaacca ccattcacac tgcgggccac agtctggcag ctgggcctga   1140

ggctggggag aaccagaagc agccggaaaa aaatgctggt cccacagcca ggacatcagc   1200

cacagtgcca gtcctgtgcc tcctggccat catcttcatc ctcaccgcag ccctttccta   1260

tgtgctgtgc aagaggagga gggggcagtc accgcagtcc tctccagatc tgccggttca   1320

ttatatacct gtggcacctg actctaatac ctgagccaag aatggaagct tgtgaggaga   1380

cggactctat gttgcccagg ctgttatgga actcctgagt caagtgatcc tcccaccttg   1440

gcctctgaag gtgcgaggat tataggcgtc acctaccaca tccagcctac acgtatttgt   1500

taatatctaa cataggacta accagccact gccctctctt aggcccctca tttaaaaacg   1560

gttatactat aaaatctgct tttcacactg ggtgataata acttggacaa attctatgtg   1620

tattttgttt tgttttgctt tgctttgttt tgagacggag tctcgctctg tcatccaggc   1680

tggagtgcag tggcatgatc tcggctcact gcaaccccca tctcccaggt tcaagcgatt   1740

ctcctgcctc ctcctgagta gctgggacta caggtgctca ccaccacacc cggctaattt   1800

tttgtatttt tagtagagac ggggtttcac catgttgacc aggctggtct cgaactcctg   1860
```

acctggtgat ctgcccaccc aggcctccca aagtgctggg attaaaggtg tgagccacca 1920
tgcctggccc tatgtgtgtt ttttaactac taaaaattat ttttgtaatg attgagtctt 1980
ctttatggaa acaactggcc tcagcccttg cgcccttact gtgattcctg gcttcatttt 2040
ttgctgatgg ttccccctcg tcccaaatct ctctcccagt acaccagttg ttcctccccc 2100
acctcagccc tctcctgcat cctcctgtac ccgcaacgaa ggcctgggct ttcccaccct 2160
ccctccttag caggtgccgt gctgggacac catacgggtt ggtttcacct cctcagtccc 2220
ttgcctaccc cagtgagagt ctgatcttgt ttttattgtt attgctttta ttattattgc 2280
ttttattatc attaaaactc tagttcttgt tttgtctctc cgaaaaaaaa aaaaaaaaaa 2340
aaaa 2344

<210> SEQ ID NO 39
<211> LENGTH: 1497
<212> TYPE: DNA
<213> ORGANISM: Homo sapiens

<400> SEQUENCE: 39
cggaccacca gcaacagaca acatcttcat tcggctctcc ctgaagctgt actgcctcgc 60
tgagaggatg aaggtctccg aggctgccct gtctctcctt gtcctcatcc ttatcattac 120
ttcggcttct cgcagccagc caaaagttcc tgagtgggtg aacaccccat ccacctgctg 180
cctgaagtat tatgagaaag tgttgccaag gagactagtg gtgggataca gaaaggccct 240
caactgtcac ctgccagcaa tcatcttcgt caccaagagg aaccgagaag tctgcaccaa 300
ccccaatgac gactgggtcc aagagtacat caaggatccc aacctacctt tgctgcctac 360
caggaacttg tccacggtta aaattattac agcaaagaat ggtcaacccc agctcctcaa 420
ctcccagtga tgaccaggct ttagtggaag cccttgttta cagaagagag ggtaaacct 480 atgaaaacag gggaagcctt attaggctga aactagccag tcacattgag agaagcagaa 540
caatgatcaa aataaaggag aagtatttcg aatattttct caatcttagg aggaaatacc 600
aaagttaagg gacgtgggca gaggtacgct cttttatttt tatatttata tttttatttt 660
tttgagatag ggtcttactc tgtcacccag gctggagtgc agtggtgtga tcttggctca 720
cttgatcttg gctcactgta acctccacct cccaggctca agtgatcctc ccaccccagc 780
ctcctgagta gctgggacta caggcttgcg ccaccacacc tggctaattt ttgtattttt 840
ggtagagacg ggattctacc atgttgccca ggctggtctc aaactcgtgt gcccaagcaa 900
tccacctgcc tcagccttcc aaaagtgctg ggattacagg cgtgagccac cacatccggc 960
cagtgcactc ttaatacaca gaaaaatata tttcacatcc ttctcctgct ctctttcaat 1020
tcctcacttc acaccagtac acaagccatt ctaaatactt agccagtttc cagccttcca 1080
gatgatcttt gccctctggg tcttgaccca ttaagagccc catagaactc ttgatttttc 1140
ctgtccatct ttatggattt ttctggatct atattttctt caattattct ttcattttat 1200
aatgcaactt tttcatagga agtccggatg ggaatattca cattaatcat ttttgcagag 1260
actttgctag atcctctcat attttgtctt cctcagggtg gcaggggtac agagagtgcc 1320
tgattggaaa aaaaaaaaaa agagagagag agagaagaag aagaagaaga gacacaaatc 1380
tctacctccc atgttaagct ttgcaggaca gggaaagaaa gggtatgaga cacggctagg 1440
ggtaaactct tagtccaaaa cccaagcatg caataaataa aactccctta tttgaca 1497

<210> SEQ ID NO 40
<211> LENGTH: 1002

<212> TYPE: DNA
<213> ORGANISM: Homo sapiens

<400> SEQUENCE: 40

```
agatgggaca gcttggccta cagcccggcg ggcatcagct cccttgaccc agtggatatc      60
ggtggccccg ttattcgtcc aggtgcccag ggaggaggac ccgcctgcag catgaacctg     120
tggctcctgg cctgcctggt ggccggcttc ctgggagcct gggcccccgc tgtccacacc     180
caaggtgtct ttgaggactg ctgcctggcc taccactacc ccattgggtg ggctgtgctc     240
cggcgcgcct ggacttaccg gatccaggag gtgagcggga gctgcaatct gcctgctgcg     300
atattctacc tccccaagag acacaggaag gtgtgtggga accccaaaag cagggaggtg     360
cagagagcca tgaagctcct ggatgctcga aataaggttt ttgcaaagct ccaccacaac     420
acgcagacct tccaagcagg ccctcatgct gtaaagaagt tgagttctgg aaactccaag     480
ttatcatcgt ccaagtttag caatcccatc agcagcagta agaggaatgt ctccctcctg     540
atatcagcta attcaggact gtgagccggc tcatttctgg gctccatcgg cacaggaggg     600
gccggatctt tctccgataa aaccgtcgcc ctacagaccc agctgtcccc acgcctctgt     660
cttttgggtc aagtcttaat ccctgcacct gagttggtcc tccctctgca cccccaccac     720
ctcctgcccg tctggcaact ggaaagaggg agttggcctg attttaagcc ttttgccgct     780
ccggggacca gcagcaatcc tgggcagcca gtggctcttg tagagaagac ttaggatacc     840
tctctcactt tctgtttctt gccgtccacc ccgggccatg ccagtgtgtc cctctgggtc     900
cctccaaaac tctggtcagt tcaaggatgc cctcccagg ctatgctttt ctataacttt      960
taaataaacc ttgggggtg atggagtcat tcctgcctgt ta                        1002
```

<210> SEQ ID NO 41
<211> LENGTH: 1002
<212> TYPE: DNA
<213> ORGANISM: Homo sapiens

<400> SEQUENCE: 41

```
agatgggaca gcttggccta cagcccggcg ggcatcagct cccttgaccc agtggatatc      60
ggtggccccg ttattcgtcc aggtgcccag ggaggaggac ccgcctgcag catgaacctg     120
tggctcctgg cctgcctggt ggccggcttc ctgggagcct gggcccccgc tgtccacacc     180
caaggtgtct ttgaggactg ctgcctggcc taccactacc ccattgggtg ggctgtgctc     240
cggcgcgcct ggacttaccg gatccaggag gtgagcggga gctgcaatct gcctgctgcg     300
atattctacc tccccaagag acacaggaag gtgtgtggga accccaaaag cagggaggtg     360
cagagagcca tgaagctcct ggatgctcga aataaggttt ttgcaaagct ccaccacaac     420
acgcagacct tccaagcagg ccctcatgct gtaaagaagt tgagttctgg aaactccaag     480
ttatcatcgt ccaagtttag caatcccatc agcagcagta agaggaatgt ctccctcctg     540
atatcagcta attcaggact gtgagccggc tcatttctgg gctccatcgg cacaggaggg     600
gccggatctt tctccgataa aaccgtcgcc ctacagaccc agctgtcccc acgcctctgt     660
cttttgggtc aagtcttaat ccctgcacct gagttggtcc tccctctgca cccccaccac     720
ctcctgcccg tctggcaact ggaaagaggg agttggcctg attttaagcc ttttgccgct     780
ccggggacca gcagcaatcc tgggcagcca gtggctcttg tagagaagac ttaggatacc     840
tctctcactt tctgtttctt gccgtccacc ccgggccatg ccagtgtgtc cctctgggtc     900
cctccaaaac tctggtcagt tcaaggatgc cctcccagg ctatgctttt ctataacttt      960
taaataaacc ttgggggtg atggagtcat tcctgcctgt ta                        1002
```

<210> SEQ ID NO 42
<211> LENGTH: 744
<212> TYPE: DNA
<213> ORGANISM: Homo sapiens

<400> SEQUENCE: 42

```
atgaacctgt ggctcctggc ctgcctggtg gccggcttcc tgggagcctg ggcccccgct     60
gtccacaccc aaggtgtctt tgaggactgc tgcctggcct accactaccc cattgggtgg    120
gctgtgctcc ggcgcgcctg gacttaccgg atccaggagg tgagcgggag ctgcaatctg    180
cctgctgcga tcaggccctc atgctgtaaa gaagttgagt tctggaaact ccaagttatc    240
atcgtccaag tttagcaatc ccatcagcag cagtaagagg aatgtctccc tcctgatatc    300
agctaattca ggactgtgag ccggctcatt tctgggctcc atcggcacag gaggggccgg    360
atctttctcc gataaaaccg tcgccctaca gacccagctg tccccacgcc tctgtctttt    420
gggtcaagtc ttaatccctg cacctgagtt ggtcctccct ctgcaccccc accacctcct    480
gcccgtctgg caactggaaa gagggagttg gcctgatttt aagccttttg ccgctccggg    540
gaccagcagc aatcctgggc agccagtggc tcttgtagag aagacttagg atacctctct    600
cactttctgt ttcttgccgt ccaccccggg ccatgccagt gtgtccctct gggtccctcc    660
aaaactctgg tcagttcaag gatgcccctc ccaggctatg cttttctata acttttaaat    720
aaaccttggg gggtgatgga gtca                                           744
```

<210> SEQ ID NO 43
<211> LENGTH: 3108
<212> TYPE: DNA
<213> ORGANISM: Homo sapiens

<400> SEQUENCE: 43

```
gaaatactcg tctctggtaa agtctgagca ggacagggtg gctgactggc agatccagag     60
gttcccttgg cagtccacgc caggccttca ccatggatca gttccctgaa tcagtgacag    120
aaaactttga gtacgatgat ttggctgagg cctgttatat tggggacatc gtggtctttg    180
ggactgtgtt cctgtccata ttctactccg tcatctttgc cattggcctg gtgggaaatt    240
tgttggtagt gtttgccctc accaacagca agaagcccaa gagtgtcacc gacatttacc    300
tcctgaacct ggccttgtct gatctgctgt ttgtagccac tttgcccttc tggactcact    360
atttgataaa tgaaaagggc ctccacaatg ccatgtgcaa attcactacc gccttcttct    420
tcatcggctt ttttggaagc atattcttca tcaccgtcat cagcattgat aggtacctgg    480
ccatcgtcct ggccgccaac tccatgaaca accggaccgt gcagcatggc gtcaccatca    540
gcctaggcgt ctgggcagca gccattttgg tggcagcacc ccagttcatg ttcacaaagc    600
agaaagaaaa tgaatgcctt ggtgactacc ccgaggtcct ccaggaaatc tggcccgtgc    660
tccgcaatgt ggaaacaaat tttcttggct tcctactccc cctgctcatt atgagttatt    720
gctacttcag aatcatccag acgctgtttt cctgcaagaa ccacaagaaa gccaaagcca    780
ttaaactgat ccttctggtg gtcatcgtgt ttttcctctt ctggacaccc tacaacgtta    840
tgattttcct ggagacgctt aagctctatg acttctttcc cagttgtgac atgaggaagg    900
atctgaggct ggccctcagt gtgactgaga cggttgcatt tagccattgt tgcctgaatc    960
ctctcatcta tgcatttgct ggggagaagt tcagaagata cctttaccac ctgtatggga   1020
aatgcctggc tgtcctgtgt gggcgctcag tccacgttga tttctcctca tctgaatcac   1080
aaaggagcag gcatggaagt gttctgagca gcaattttac ttaccacacg agtgatggag   1140
```

```
atgcattgct ccttctctga agggaatccc aaagccttgt gtctacagag aacctggagt   1200

tcctgaacct gatgctgact agtgaggaaa gatttttgtt gttatttctt acaggcacaa   1260

aatgatggac ccaatgcaca caaaacaacc ctagagtgtt gttgagaatt gtgctcaaaa   1320

tttgaagaat gaacaaattg aactctttga atgacaaaga gtagacattt ctcttactgc   1380

aaatgtcatc agaacttttt ggtttgcaga tgacaaaaat tcaactcaga ctagtttagt   1440

taaatgaggg tggtgaatat tgttcatatt gtggcacaag caaaagggtg tctgagccct   1500

caaagtgagg ggaaaccagg gcctgagcca agctagaatt ccctctctct gactctcaaa   1560

tcttttagtc attatagatc ccccagactt tacatgacac agctttatca ccagagaggg   1620

actgacaccc atgtttctct ggccccaagg gcaaaattcc cagggaagtg ctctgatagg   1680

ccaagtttgt atcaggtgcc catccctgga aggtgctgtt atccatgggg aagggatata   1740

taagatggaa gcttccagtc caatctcatg gagaagcaga aatacatatt tccaagaagt   1800

tggatgggtg ggtactattc tgattacaca aaacaaatgc cacacatcac ccttaccatg   1860

tgcctgatcc agcctctccc ctgattacac cagcctcgtc ttcattaagc cctcttccat   1920

catgtcccca aacctgcaag ggctccccac tgcctactgc atcgagtcaa aactcaaatg   1980

cttggcttct catacgtcca ccatggggtc ctaccaatag attccccatt gcctcctcct   2040

tcccaaagga ctccacccat cctatcagcc tgtctcttcc atatgacctc atgcatctcc   2100

acctgctccc aggccagtaa gggaaataga aaaaccctgc ccccaaataa gaagggatgg   2160

attccaaccc caactccagt agcttgggac aaatcaagct tcagtttcct ggtctgtaga   2220

agagggataa ggtacctttc acatagagat catcctttcc agcatgagga actagccacc   2280

aactcttgca ggtctcaacc cttttgtctg cctcttagac ttctgctttc cacacctggc   2340

actgctgtgc tgtgcccaag ttgtggtgct gacaaagctt ggaagagcct gcaggtgctg   2400

ctgcgtggca tagcccagac acagaagagg ctggttctta cgatggcacc cagtgagcac   2460

tcccaagtct acagagtgat agccttccgt aacccaactc tcctggactg ccttgaatat   2520

cccctcccag tcaccttgtg gcaagcccct gcccatctgg gaaaataccc catcattcat   2580

gctactgcca acctggggag ccagggctat gggagcagct tttttttccc ccctagaaac   2640

gtttggaaca atctaaaagt ttaaagctcg aaaacaattg taataatgct aaagaaaaag   2700

tcatccaatc taaccacatc aatattgtca ttcctgtatt cacccgtcca gaccttgttc   2760

acactctcac atgtttagag ttgcaatcgt aatgtacaga tggttttata atctgatttg   2820

ttttcctctt aacgttagac cacaaatagt gctcgctttc tatgtagttt ggtaattatc   2880

attttagaag actctaccag actgtgtatt cattgaagtc agatgtggta actgttaaat   2940

tgctgtgtat ctgatagctc tttggcagtc tatatgtttg tataatgaat gagagaataa   3000

gtcatgttcc ttcaagatca tgtaccccaa tttacttgcc attactcaat tgataaacat   3060

ttaacttgtt tccaatgttt agcaaataca tattttatag aacttcca               3108
```

<210> SEQ ID NO 44
<211> LENGTH: 3304
<212> TYPE: DNA
<213> ORGANISM: Homo sapiens

<400> SEQUENCE: 44

```
ctgagctctg ccgcctggct ctagccgcct gcctggcccc cgccgggact cttgcccacc     60

ctcagccatg gctccgatat ctctgtcgtg gctgctccgc ttggccacct tctgccatct    120

gactgtcctg ctggctggac agcaccacgg tgtgacgaaa tgcaacatca cgtgcagcaa    180
```

```
gatgacatca aagatacctg tagctttgct catccactat caacagaacc aggcatcatg    240
cggcaaacgc gcaatcatct tggagacgag acagcacagg ctgttctgtg ccgacccgaa    300
ggagcaatgg gtcaaggacg cgatgcagca tctggaccgc caggctgctg ccctaactcg    360
aaatggcggc accttcgaga agcagatcgg cgaggtgaag cccaggacca cccctgccgc    420
cgggggaatg gacgagtctg tggtcctgga gcccgaagcc acaggcgaaa gcagtagcct    480
ggagccgact ccttcttccc aggaagcaca gagggccctg ggacctcccc cagagctgcc    540
gacgggcgtg actggttcct cagggaccag gctccccccg acgccaaagg ctcaggatgg    600
agggcctgtg ggcacggagc ttttccgagt gcctcccgtc tccactgccg ccacgtggca    660
gagttctgct ccccaccaac ctgggcccag cctctgggct gaggcaaaga cctctgaggc    720
cccgtccacc caggacccct ccacccaggc ctccactgcg tcctccccag ccccagagga    780
gaatgctccg tctgaaggcc agcgtgtgtg gggtcaggga cagagcccca ggccagagaa    840
ctctctggag cgggaggaga tgggtcccgt gccagcgcac acggatgcct tccaggactg    900
gggcctggc agcatggccc acgtctctgt ggtccctgtc tcctcagaag ggacccccag    960
cagggagcca gtggcttcag gcagctggac ccctaaggct gaggaaccca tccatgccac   1020
catggacccc cagaggctgg gcgtccttat cactcctgtc cctgacgccc aggctgccac   1080
ccggaggcag gcggtggggc tgctggcctt ccttggcctc ctcttctgcc tgggggtggc   1140
catgttcacc taccagagcc tccagggctg ccctcgaaag atggcaggag agatggcgga   1200
gggccttcgc tacatccccc ggagctgtgg tagtaattca tatgtcctgg tgcccgtgtg   1260
aactcctctg gcctgtgtct agttgtttga ttcagacagc tgcctgggat ccctcatcct   1320
catacccacc cccacccaag ggcctggcct gagctgggat gattggaggg gggaggtggg   1380
atcctccagg tgcacaagct ccaagctccc aggcattccc caggaggcca gccttgacca   1440
ttctccacct tccagggaca gagggggtgg cctcccaact caccccagcc ccaaaactct   1500
cctctgctgc tggctggtta gaggttccct ttgacgccat cccagcccca atgaacaatt   1560
atttattaaa tgcccagccc cttctgaccc atgctgccct gtgagtacta cagtcctccc   1620
atctcacaca tgagcatcag gccaggccct ctgcccactc cctgcaacct gattgtgtct   1680
cttggtcctg ctgcagttgc cagtcacccc ggccacctgc ggtgctatct cccccagccc   1740
catcctctgt acagagccca cgccccact ggtgacatgt cttttcttgc atgaggctag   1800
tgtggtgttt cctggcactg cttccagtga ggctctgccc ttggttaggc attgtgggaa   1860
ggggagataa gggtatctgg tgactttcct ctttggtcta cactgtgctg agtctgaagg   1920
ctgggttctg atcctagttc caccatcaag ccaccaacat actcccatct gtgaaaggaa   1980
agagggaggt aaggaatacc tgtcccctg acaacactca ttgacctgag gcccttctct   2040
ccagcccctg gatgcagcct cacagtcctt accagcagag caccttagac agtccctgcc   2100
aatggactaa cttgtctttg gaccctgagg cccagagggc ctgcaaggga gtgagttgat   2160
agcacagacc ctgccctgtg ggcccccaaa tggaaatggg cagagcagag accatccctg   2220
aaggccccgc ccaggcttag tcactgagac agcccgggct ctgcctccca tcacccgcta   2280
agagggaggg agggctccag acacatgtcc aagaagccca ggaaaggctc caggagcagc   2340
cacattcctg atgcttcttc agagactcct gcaggcagcc aggccacaag acccttgtgg   2400
tcccacccca cacacgccag attctttcct gaggctgggc tcccttccca cctctctcac   2460
tccttgaaaa cactgttctc tgccctccaa gaccttctcc ttcacctttg tccccaccgc   2520
agacaggacc agggatttcc atgatgtttt ccatgagtcc cctgtttgtt tctgaaaggg   2580
```

```
acgctacccg ggaagggggc tgggacatgg gaaaggggaa gttgtaggca taaagtcagg   2640

ggttcccttt tttggctgct gaaggctcga gcatgcctgg atggggctgc accggctggc   2700

ctggcccctc agggtccctg gtggcagctc acctctccct tggattgtcc ccgacccttg   2760

ccgtctacct gaggggcctc ttatgggctg ggttctaccc aggtgctagg aacactcctt   2820

cacagatggg tgcttggagg aaggaaaccc agctctggtc catagagagc aagacgctgt   2880

gctgccctgc ccacctggcc tctgcactcc cctgctgggt gtggcgcagc atattcagga   2940

agctcagggc ctggctcagg tggggtcact ctggcagctc agagagggtg ggagtgggtc   3000

caatgcactt tgttctggct cttccaggct gggagagcct ttcaggggtg ggacaccctg   3060

tgatggggcc ctgcctcctt tgtgaggaag ccgctggggc cagttggtcc cccttccatg   3120

gactttgtta gtttctccaa gcaggacatg gacaaggatg atctaggaag actttggaaa   3180

gagtaggaag actttggaaa gacttttcca accctcatca ccaacgtctg tgccattttg   3240

tattttacta ataaaattta aaagtcttgt gaaaaaaaaa aaaaaaaaaa aaaaaaaaaa   3300

aaaa                                                                3304


<210> SEQ ID NO 45
<211> LENGTH: 16
<212> TYPE: PRT
<213> ORGANISM: Homo sapiens

<400> SEQUENCE: 45

Arg Ser Ser Ser Thr Leu Pro Val Pro Val Phe Lys Arg Lys Ile Pro
1               5                   10                  15


<210> SEQ ID NO 46
<211> LENGTH: 16
<212> TYPE: PRT
<213> ORGANISM: Homo sapiens

<400> SEQUENCE: 46

Pro Arg Gly Asn Gly Cys Pro Arg Lys Glu Ile Ile Val Trp Lys Lys
1               5                   10                  15


<210> SEQ ID NO 47
<211> LENGTH: 16
<212> TYPE: PRT
<213> ORGANISM: Homo sapiens

<400> SEQUENCE: 47

Leu Pro Arg Gly Asn Gly Cys Pro Arg Lys Glu Ile Ile Val Trp Lys
1               5                   10                  15


<210> SEQ ID NO 48
<211> LENGTH: 16
<212> TYPE: PRT
<213> ORGANISM: Homo sapiens

<400> SEQUENCE: 48

Gln Ile Leu Pro Arg Gly Asn Gly Cys Pro Arg Lys Glu Ile Ile Val
1               5                   10                  15


<210> SEQ ID NO 49
<211> LENGTH: 16
<212> TYPE: PRT
<213> ORGANISM: Homo sapiens

<400> SEQUENCE: 49

Ile Leu Pro Arg Gly Asn Gly Cys Pro Arg Lys Glu Ile Ile Val Trp
```

1 5 10 15

<210> SEQ ID NO 50
<211> LENGTH: 16
<212> TYPE: PRT
<213> ORGANISM: Homo sapiens

<400> SEQUENCE: 50

Arg Ile Gln Ile Leu Pro Arg Gly Asn Gly Cys Pro Arg Lys Glu Ile
1 5 10 15

<210> SEQ ID NO 51
<211> LENGTH: 16
<212> TYPE: PRT
<213> ORGANISM: Homo sapiens

<400> SEQUENCE: 51

Arg Gly Asn Gly Cys Pro Arg Lys Glu Ile Ile Val Trp Lys Lys Asn
1 5 10 15

<210> SEQ ID NO 52
<211> LENGTH: 16
<212> TYPE: PRT
<213> ORGANISM: Homo sapiens

<400> SEQUENCE: 52

Lys Arg Ser Ser Ser Thr Leu Pro Val Pro Val Phe Lys Arg Lys Ile
1 5 10 15

<210> SEQ ID NO 53
<211> LENGTH: 16
<212> TYPE: PRT
<213> ORGANISM: Homo sapiens

<400> SEQUENCE: 53

Ile Gln Ile Leu Pro Arg Gly Asn Gly Cys Pro Arg Lys Glu Ile Ile
1 5 10 15

<210> SEQ ID NO 54
<211> LENGTH: 16
<212> TYPE: PRT
<213> ORGANISM: Homo sapiens

<400> SEQUENCE: 54

Asp Arg Ile Gln Ile Leu Pro Arg Gly Asn Gly Cys Pro Arg Lys Glu
1 5 10 15

<210> SEQ ID NO 55
<211> LENGTH: 16
<212> TYPE: PRT
<213> ORGANISM: Homo sapiens

<400> SEQUENCE: 55

Arg Lys Arg Ser Ser Ser Thr Leu Pro Val Pro Val Phe Lys Arg Lys
1 5 10 15

<210> SEQ ID NO 56
<211> LENGTH: 16
<212> TYPE: PRT
<213> ORGANISM: Homo sapiens

<400> SEQUENCE: 56

Arg Cys Arg Cys Val Gln Glu Ser Ser Val Phe Ile Pro Arg Arg Phe
1 5 10 15

<210> SEQ ID NO 57
<211> LENGTH: 16
<212> TYPE: PRT
<213> ORGANISM: Homo sapiens

<400> SEQUENCE: 57

```
Gly Asn Gly Cys Pro Arg Lys Glu Ile Ile Val Trp Lys Lys Asn Lys
1               5                   10                  15
```

<210> SEQ ID NO 58
<211> LENGTH: 16
<212> TYPE: PRT
<213> ORGANISM: Homo sapiens

<400> SEQUENCE: 58

```
Cys Val Gln Glu Ser Ser Val Phe Ile Pro Arg Arg Phe Ile Asp Arg
1               5                   10                  15
```

<210> SEQ ID NO 59
<211> LENGTH: 16
<212> TYPE: PRT
<213> ORGANISM: Homo sapiens

<400> SEQUENCE: 59

```
Ile Asp Arg Ile Gln Ile Leu Pro Arg Gly Asn Gly Cys Pro Arg Lys
1               5                   10                  15
```

<210> SEQ ID NO 60
<211> LENGTH: 16
<212> TYPE: PRT
<213> ORGANISM: Homo sapiens

<400> SEQUENCE: 60

```
Leu Arg Cys Arg Cys Val Gln Glu Ser Ser Val Phe Ile Pro Arg Arg
1               5                   10                  15
```

<210> SEQ ID NO 61
<211> LENGTH: 16
<212> TYPE: PRT
<213> ORGANISM: Homo sapiens

<400> SEQUENCE: 61

```
Phe Ile Asp Arg Ile Gln Ile Leu Pro Arg Gly Asn Gly Cys Pro Arg
1               5                   10                  15
```

<210> SEQ ID NO 62
<211> LENGTH: 16
<212> TYPE: PRT
<213> ORGANISM: Homo sapiens

<400> SEQUENCE: 62

```
Arg Cys Val Gln Glu Ser Ser Val Phe Ile Pro Arg Arg Phe Ile Asp
1               5                   10                  15
```

<210> SEQ ID NO 63
<211> LENGTH: 16
<212> TYPE: PRT
<213> ORGANISM: Homo sapiens

<400> SEQUENCE: 63

```
Cys Arg Cys Val Gln Glu Ser Ser Val Phe Ile Pro Arg Arg Phe Ile
1               5                   10                  15
```

<210> SEQ ID NO 64
<211> LENGTH: 16
<212> TYPE: PRT

<213> ORGANISM: Homo sapiens

<400> SEQUENCE: 64

```
Gln Glu Ser Ser Val Phe Ile Pro Arg Arg Phe Ile Asp Arg Ile Gln
1               5                   10                  15
```

<210> SEQ ID NO 65
<211> LENGTH: 16
<212> TYPE: PRT
<213> ORGANISM: Homo sapiens

<400> SEQUENCE: 65

```
Arg Phe Ile Asp Arg Ile Gln Ile Leu Pro Arg Gly Asn Gly Cys Pro
1               5                   10                  15
```

<210> SEQ ID NO 66
<211> LENGTH: 16
<212> TYPE: PRT
<213> ORGANISM: Homo sapiens

<400> SEQUENCE: 66

```
Val Gln Glu Ser Ser Val Phe Ile Pro Arg Arg Phe Ile Asp Arg Ile
1               5                   10                  15
```

<210> SEQ ID NO 67
<211> LENGTH: 16
<212> TYPE: PRT
<213> ORGANISM: Homo sapiens

<400> SEQUENCE: 67

```
Glu Ser Ser Val Phe Ile Pro Arg Arg Phe Ile Asp Arg Ile Gln Ile
1               5                   10                  15
```

<210> SEQ ID NO 68
<211> LENGTH: 16
<212> TYPE: PRT
<213> ORGANISM: Homo sapiens

<400> SEQUENCE: 68

```
Ser Leu Arg Cys Arg Cys Val Gln Glu Ser Ser Val Phe Ile Pro Arg
1               5                   10                  15
```

<210> SEQ ID NO 69
<211> LENGTH: 16
<212> TYPE: PRT
<213> ORGANISM: Homo sapiens

<400> SEQUENCE: 69

```
Asn Gly Cys Pro Arg Lys Glu Ile Ile Val Trp Lys Lys Asn Lys Ser
1               5                   10                  15
```

<210> SEQ ID NO 70
<211> LENGTH: 16
<212> TYPE: PRT
<213> ORGANISM: Homo sapiens

<400> SEQUENCE: 70

```
Pro Gln Ala Glu Trp Ile Gln Arg Met Met Glu Val Leu Arg Lys Arg
1               5                   10                  15
```

<210> SEQ ID NO 71
<211> LENGTH: 16
<212> TYPE: PRT
<213> ORGANISM: Homo sapiens

<400> SEQUENCE: 71

```
Arg Arg Phe Ile Asp Arg Ile Gln Ile Leu Pro Arg Gly Asn Gly Cys
1               5                   10                  15


<210> SEQ ID NO 72
<211> LENGTH: 16
<212> TYPE: PRT
<213> ORGANISM: Homo sapiens

<400> SEQUENCE: 72

Leu Arg Lys Arg Ser Ser Ser Thr Leu Pro Val Pro Val Phe Lys Arg
1               5                   10                  15


<210> SEQ ID NO 73
<211> LENGTH: 11
<212> TYPE: PRT
<213> ORGANISM: Homo sapiens

<400> SEQUENCE: 73

Val Gln Glu Ser Ser Val Phe Ile Pro Arg Arg
1               5                   10


<210> SEQ ID NO 74
<211> LENGTH: 26
<212> TYPE: PRT
<213> ORGANISM: Homo sapiens

<400> SEQUENCE: 74

Glu Trp Ile Gln Arg Met Met Glu Val Leu Arg Lys Arg Ser Ser Ser
1               5                   10                  15

Thr Leu Pro Val Pro Val Phe Lys Arg Lys
            20                  25


<210> SEQ ID NO 75
<211> LENGTH: 4
<212> TYPE: PRT
<213> ORGANISM: Homo sapiens

<400> SEQUENCE: 75

Lys Lys Asn Lys
1


<210> SEQ ID NO 76
<211> LENGTH: 6
<212> TYPE: PRT
<213> ORGANISM: Homo sapiens

<400> SEQUENCE: 76

Arg Lys Arg Ser Ser Ser
1               5


<210> SEQ ID NO 77
<211> LENGTH: 6
<212> TYPE: PRT
<213> ORGANISM: Homo sapiens

<400> SEQUENCE: 77

Arg Gly Asn Gly Cys Pro
1               5


<210> SEQ ID NO 78
<211> LENGTH: 21
<212> TYPE: PRT
<213> ORGANISM: Homo sapiens

<400> SEQUENCE: 78
```

```
Val Tyr Tyr Thr Ser Leu Arg Cys Arg Cys Val Gln Glu Ser Ser Val
1               5                   10                  15

Phe Ile Pro Arg Arg
            20


<210> SEQ ID NO 79
<211> LENGTH: 7
<212> TYPE: PRT
<213> ORGANISM: Homo sapiens

<400> SEQUENCE: 79

Asp Arg Ile Gln Ile Leu Pro
1               5


<210> SEQ ID NO 80
<211> LENGTH: 7
<212> TYPE: PRT
<213> ORGANISM: Homo sapiens

<400> SEQUENCE: 80

Arg Lys Glu Ile Ile Val Trp
1               5


<210> SEQ ID NO 81
<211> LENGTH: 9
<212> TYPE: PRT
<213> ORGANISM: Homo sapiens

<400> SEQUENCE: 81

Lys Ser Ile Val Cys Val Asp Pro Gln
1               5


<210> SEQ ID NO 82
<211> LENGTH: 13
<212> TYPE: PRT
<213> ORGANISM: Homo sapiens

<400> SEQUENCE: 82

Thr Ser Leu Val Glu Asn His Leu Cys Pro Ala Thr Glu
1               5                   10


<210> SEQ ID NO 83
<211> LENGTH: 15
<212> TYPE: PRT
<213> ORGANISM: Homo sapiens

<400> SEQUENCE: 83

Glu Gly Ser Val Gly Trp Val Leu Gly Thr Phe Leu Cys Lys Thr
1               5                   10                  15


<210> SEQ ID NO 84
<211> LENGTH: 7
<212> TYPE: PRT
<213> ORGANISM: Homo sapiens

<400> SEQUENCE: 84

Leu Pro Arg Cys Thr Phe Ser
1               5


<210> SEQ ID NO 85
<211> LENGTH: 10
<212> TYPE: PRT
<213> ORGANISM: Homo sapiens

<400> SEQUENCE: 85
```

Leu Ala Arg Leu Lys Ala Val Asp Asn Thr
1 5 10

<210> SEQ ID NO 86
<211> LENGTH: 10
<212> TYPE: PRT
<213> ORGANISM: Homo sapiens

<400> SEQUENCE: 86

Met Ala Ser Phe Lys Ala Val Phe Val Pro
1 5 10

<210> SEQ ID NO 87
<211> LENGTH: 16
<212> TYPE: PRT
<213> ORGANISM: Homo sapiens

<400> SEQUENCE: 87

Ala Ala Gly Pro Glu Ala Gly Glu Asn Gln Lys Gln Pro Glu Lys Asn
1 5 10 15

<210> SEQ ID NO 88
<211> LENGTH: 16
<212> TYPE: PRT
<213> ORGANISM: Homo sapiens

<400> SEQUENCE: 88

Ser Gln Ala Ser Glu Gly Ala Ser Ser Asp Ile His Thr Pro Ala Gln
1 5 10 15

<210> SEQ ID NO 89
<211> LENGTH: 16
<212> TYPE: PRT
<213> ORGANISM: Homo sapiens

<400> SEQUENCE: 89

Ser Thr Leu Gln Ser Thr Gln Arg Pro Thr Leu Pro Val Gly Ser Leu
1 5 10 15

<210> SEQ ID NO 90
<211> LENGTH: 16
<212> TYPE: PRT
<213> ORGANISM: Homo sapiens

<400> SEQUENCE: 90

Ser Trp Ser Val Cys Gly Gly Asn Lys Asp Pro Trp Val Gln Glu Leu
1 5 10 15

<210> SEQ ID NO 91
<211> LENGTH: 16
<212> TYPE: PRT
<213> ORGANISM: Homo sapiens

<400> SEQUENCE: 91

Gly Pro Thr Ala Arg Thr Ser Ala Thr Val Pro Val Leu Cys Leu Leu
1 5 10 15

<210> SEQ ID NO 92
<211> LENGTH: 16
<212> TYPE: PRT
<213> ORGANISM: Homo sapiens

<400> SEQUENCE: 92

Ser Gly Ile Val Ala His Gln Lys His Leu Leu Pro Thr Ser Pro Pro
1 5 10 15

<210> SEQ ID NO 93
<211> LENGTH: 6
<212> TYPE: PRT
<213> ORGANISM: Homo sapiens

<400> SEQUENCE: 93

```
Arg Leu Arg Lys His Leu
1               5
```

<210> SEQ ID NO 94
<211> LENGTH: 7
<212> TYPE: PRT
<213> ORGANISM: Homo sapiens

<400> SEQUENCE: 94

```
Leu Gln Ser Thr Gln Arg Pro
1               5
```

<210> SEQ ID NO 95
<211> LENGTH: 13
<212> TYPE: PRT
<213> ORGANISM: Homo sapiens

<400> SEQUENCE: 95

```
Ser Ser Asp Lys Glu Leu Thr Arg Pro Asn Glu Thr Thr
1               5                   10
```

<210> SEQ ID NO 96
<211> LENGTH: 12
<212> TYPE: PRT
<213> ORGANISM: Homo sapiens

<400> SEQUENCE: 96

```
Ala Gly Glu Asn Gln Lys Gln Pro Glu Lys Asn Ala
1               5                   10
```

<210> SEQ ID NO 97
<211> LENGTH: 6
<212> TYPE: PRT
<213> ORGANISM: Homo sapiens

<400> SEQUENCE: 97

```
Asn Glu Gly Ser Val Thr
1               5
```

<210> SEQ ID NO 98
<211> LENGTH: 9
<212> TYPE: PRT
<213> ORGANISM: Homo sapiens

<400> SEQUENCE: 98

```
Ile Ser Ser Asp Ser Pro Pro Ser Val
1               5
```

<210> SEQ ID NO 99
<211> LENGTH: 8
<212> TYPE: PRT
<213> ORGANISM: Homo sapiens

<400> SEQUENCE: 99

```
Cys Gly Gly Asn Lys Asp Pro Trp
1               5
```

<210> SEQ ID NO 100

<211> LENGTH: 21
<212> TYPE: PRT
<213> ORGANISM: Homo sapiens

<400> SEQUENCE: 100

```
Leu Leu Pro Thr Ser Pro Pro Ile Ser Gln Ala Ser Glu Gly Ala Ser
1               5                   10                  15

Ser Asp Ile His Thr
            20
```

<210> SEQ ID NO 101
<211> LENGTH: 28
<212> TYPE: PRT
<213> ORGANISM: Homo sapiens

<400> SEQUENCE: 101

```
Ser Thr Gln Arg Pro Thr Leu Pro Val Gly Ser Leu Ser Ser Asp Lys
1               5                   10                  15

Glu Leu Thr Arg Pro Asn Glu Thr Thr Ile His Thr
            20                  25
```

<210> SEQ ID NO 102
<211> LENGTH: 27
<212> TYPE: PRT
<213> ORGANISM: Homo sapiens

<400> SEQUENCE: 102

```
Ser Leu Ala Ala Gly Pro Glu Ala Gly Glu Asn Gln Lys Gln Pro Glu
1               5                   10                  15

Lys Asn Ala Gly Pro Thr Ala Arg Thr Ser Ala
            20                  25
```

<210> SEQ ID NO 103
<211> LENGTH: 9
<212> TYPE: PRT
<213> ORGANISM: Homo sapiens

<400> SEQUENCE: 103

```
Thr Gly Ser Cys Tyr Cys Gly Lys Arg
1               5
```

<210> SEQ ID NO 104
<211> LENGTH: 7
<212> TYPE: PRT
<213> ORGANISM: Homo sapiens

<400> SEQUENCE: 104

```
Asp Ser Pro Pro Ser Val Gln
1               5
```

<210> SEQ ID NO 105
<211> LENGTH: 26
<212> TYPE: PRT
<213> ORGANISM: Homo sapiens

<400> SEQUENCE: 105

```
Arg Lys His Leu Arg Ala Tyr His Arg Cys Leu Tyr Tyr Thr Arg Phe
1               5                   10                  15

Gln Leu Leu Ser Trp Ser Val Cys Gly Gly
            20                  25
```

<210> SEQ ID NO 106
<211> LENGTH: 37
<212> TYPE: PRT

<213> ORGANISM: Homo sapiens

<400> SEQUENCE: 106

```
Trp Val Gln Glu Leu Met Ser Cys Leu Asp Leu Lys Glu Cys Gly His
1               5                   10                  15

Ala Tyr Ser Gly Ile Val Ala His Gln Lys His Leu Leu Pro Thr Ser
            20                  25                  30

Pro Pro Ile Ser Gln
        35
```

<210> SEQ ID NO 107
<211> LENGTH: 15
<212> TYPE: PRT
<213> ORGANISM: Homo sapiens

<400> SEQUENCE: 107

```
Ser Asp Ile His Thr Pro Ala Gln Met Leu Leu Ser Thr Leu Gln
1               5                   10                  15
```

<210> SEQ ID NO 108
<211> LENGTH: 9
<212> TYPE: PRT
<213> ORGANISM: Homo sapiens

<400> SEQUENCE: 108

```
Arg Pro Thr Leu Pro Val Gly Ser Leu
1               5
```

<210> SEQ ID NO 109
<211> LENGTH: 9
<212> TYPE: PRT
<213> ORGANISM: Homo sapiens

<400> SEQUENCE: 109

```
Thr Ala Gly His Ser Leu Ala Ala Gly
1               5
```

<210> SEQ ID NO 110
<211> LENGTH: 13
<212> TYPE: PRT
<213> ORGANISM: Homo sapiens

<400> SEQUENCE: 110

```
Gly Lys Arg Ile Ser Ser Asp Ser Pro Pro Ser Val Gln
1               5                   10
```

<210> SEQ ID NO 111
<211> LENGTH: 30
<212> TYPE: PRT
<213> ORGANISM: Homo sapiens

<400> SEQUENCE: 111

```
Lys Asp Pro Trp Val Gln Glu Leu Met Ser Cys Leu Asp Leu Lys Glu
1               5                   10                  15

Cys Gly His Ala Tyr Ser Gly Ile Val Ala His Gln Lys His
            20                  25                  30
```

<210> SEQ ID NO 112
<211> LENGTH: 10
<212> TYPE: PRT
<213> ORGANISM: Homo sapiens

<400> SEQUENCE: 112

```
His Gln Asp Phe Leu Gln Phe Ser Lys Val
```

1 5 10

<210> SEQ ID NO 113
<211> LENGTH: 14
<212> TYPE: PRT
<213> ORGANISM: Homo sapiens

<400> SEQUENCE: 113

Ala Gly Ile His Glu Trp Val Phe Gly Gln Val Met Cys Lys
1 5 10

<210> SEQ ID NO 114
<211> LENGTH: 23
<212> TYPE: PRT
<213> ORGANISM: Homo sapiens

<400> SEQUENCE: 114

Pro Gln Ile Ile Tyr Gly Asn Val Phe Asn Leu Asp Lys Leu Ile Cys
1 5 10 15

Gly Tyr His Asp Glu Ala Ile
20

<210> SEQ ID NO 115
<211> LENGTH: 16
<212> TYPE: PRT
<213> ORGANISM: Homo sapiens

<400> SEQUENCE: 115

Tyr Tyr Ala Met Thr Ser Phe His Tyr Thr Ile Met Val Thr Glu Ala
1 5 10 15

<210> SEQ ID NO 116
<211> LENGTH: 12
<212> TYPE: PRT
<213> ORGANISM: Homo sapiens

<400> SEQUENCE: 116

Leu Ala Tyr His Tyr Pro Ile Gly Trp Ala Val Leu
1 5 10

<210> SEQ ID NO 117
<211> LENGTH: 34
<212> TYPE: PRT
<213> ORGANISM: Homo sapiens

<400> SEQUENCE: 117

Lys Arg His Arg Lys Val Cys Gly Asn Pro Lys Ser Arg Glu Val Gln
1 5 10 15

Arg Ala Met Lys Leu Leu Asp Ala Arg Asn Lys Val Phe Ala Lys Leu
20 25 30

His His

<210> SEQ ID NO 118
<211> LENGTH: 20
<212> TYPE: PRT
<213> ORGANISM: Homo sapiens

<400> SEQUENCE: 118

Phe Glu Asp Cys Cys Leu Ala Tyr His Tyr Pro Ile Gly Trp Ala Val
1 5 10 15

Leu Arg Arg Ala
20

<210> SEQ ID NO 119
<211> LENGTH: 27
<212> TYPE: PRT
<213> ORGANISM: Homo sapiens

<400> SEQUENCE: 119

```
Ile Gln Glu Val Ser Gly Ser Cys Asn Leu Pro Ala Ala Ile Phe Tyr
1               5                   10                  15

Leu Pro Lys Arg His Arg Lys Val Cys Gly Asn
            20                  25
```

<210> SEQ ID NO 120
<211> LENGTH: 8
<212> TYPE: PRT
<213> ORGANISM: Homo sapiens

<400> SEQUENCE: 120

```
Ala Met Lys Leu Leu Asp Ala Arg
1               5
```

<210> SEQ ID NO 121
<211> LENGTH: 9
<212> TYPE: PRT
<213> ORGANISM: Homo sapiens

<400> SEQUENCE: 121

```
Lys Val Phe Ala Lys Leu His His Asn
1               5
```

<210> SEQ ID NO 122
<211> LENGTH: 10
<212> TYPE: PRT
<213> ORGANISM: Homo sapiens

<400> SEQUENCE: 122

```
Gln Ala Gly Pro His Ala Val Lys Lys Leu
1               5                   10
```

<210> SEQ ID NO 123
<211> LENGTH: 14
<212> TYPE: PRT
<213> ORGANISM: Homo sapiens

<400> SEQUENCE: 123

```
Phe Tyr Leu Pro Lys Arg His Arg Lys Val Cys Gly Asn Pro
1               5                   10
```

<210> SEQ ID NO 124
<211> LENGTH: 14
<212> TYPE: PRT
<213> ORGANISM: Homo sapiens

<400> SEQUENCE: 124

```
Tyr Leu Pro Lys Arg His Arg Lys Val Cys Gly Asn Pro Lys
1               5                   10
```

<210> SEQ ID NO 125
<211> LENGTH: 14
<212> TYPE: PRT
<213> ORGANISM: Homo sapiens

<400> SEQUENCE: 125

```
Leu Pro Lys Arg His Arg Lys Val Cys Gly Asn Pro Lys Ser
1               5                   10
```

<210> SEQ ID NO 126
<211> LENGTH: 14
<212> TYPE: PRT
<213> ORGANISM: Homo sapiens

<400> SEQUENCE: 126

Pro Lys Arg His Arg Lys Val Cys Gly Asn Pro Lys Ser Arg
1 5 10

<210> SEQ ID NO 127
<211> LENGTH: 14
<212> TYPE: PRT
<213> ORGANISM: Homo sapiens

<400> SEQUENCE: 127

Cys Gly Asn Pro Lys Ser Arg Glu Val Gln Arg Ala Met Lys
1 5 10

<210> SEQ ID NO 128
<211> LENGTH: 14
<212> TYPE: PRT
<213> ORGANISM: Homo sapiens

<400> SEQUENCE: 128

Gly Asn Pro Lys Ser Arg Glu Val Gln Arg Ala Met Lys Leu
1 5 10

<210> SEQ ID NO 129
<211> LENGTH: 14
<212> TYPE: PRT
<213> ORGANISM: Homo sapiens

<400> SEQUENCE: 129

Lys Phe Ser Asn Pro Ile Ser Ser Ser Lys Arg Asn Val Ser
1 5 10

<210> SEQ ID NO 130
<211> LENGTH: 6
<212> TYPE: PRT
<213> ORGANISM: Homo sapiens

<400> SEQUENCE: 130

Pro Lys Ser Arg Glu Val
1 5

<210> SEQ ID NO 131
<211> LENGTH: 7
<212> TYPE: PRT
<213> ORGANISM: Homo sapiens

<400> SEQUENCE: 131

Leu His His Asn Thr Gln Thr
1 5

<210> SEQ ID NO 132
<211> LENGTH: 6
<212> TYPE: PRT
<213> ORGANISM: Homo sapiens

<400> SEQUENCE: 132

Ser Ser Ser Lys Arg Asn
1 5

<210> SEQ ID NO 133
<211> LENGTH: 9
<212> TYPE: PRT

```
<213> ORGANISM: Homo sapiens

<400> SEQUENCE: 133

Gln Phe Ala Ser His Phe Leu Pro Pro
1               5


<210> SEQ ID NO 134
<211> LENGTH: 9
<212> TYPE: PRT
<213> ORGANISM: Homo sapiens

<400> SEQUENCE: 134

Ala Ala Ala Asp Gln Trp Lys Phe Gln
1               5


<210> SEQ ID NO 135
<211> LENGTH: 10
<212> TYPE: PRT
<213> ORGANISM: Homo sapiens

<400> SEQUENCE: 135

Thr Phe Met Cys Lys Val Val Asn Ser Met
1               5                   10


<210> SEQ ID NO 136
<211> LENGTH: 10
<212> TYPE: PRT
<213> ORGANISM: Homo sapiens

<400> SEQUENCE: 136

Ile Ala Ile Cys Thr Met Val Tyr Pro Ser
1               5                   10


<210> SEQ ID NO 137
<211> LENGTH: 25
<212> TYPE: PRT
<213> ORGANISM: Homo sapiens

<400> SEQUENCE: 137

Val Gln Thr Ile Asp Ala Tyr Ala Met Phe Ile Ser Asn Cys Ala Val
1               5                   10                  15

Ser Thr Asn Ile Asp Ile Cys Phe Gln
            20                  25
```